(12) United States Patent
Yin et al.

(10) Patent No.: US 11,608,334 B2
(45) Date of Patent: Mar. 21, 2023

(54) PYRROLO-AROMATIC HETEROCYCLIC COMPOUND, PREPARATION METHOD THEREFOR, AND MEDICAL USE THEREOF

(71) Applicant: The National Institutes of Pharmaceutical R&D Co., Ltd., Beijing (CN)

(72) Inventors: Huijun Yin, Beijing (CN); Xu Yan, Beijing (CN); Libin Zong, Beijing (CN); Weixue Tian, Beijing (CN); Li Zheng, Beijing (CN); Haoshuai Dou, Beijing (CN); Yan Yang, Beijing (CN)

(73) Assignee: THE NATIONAL INSTITUTES OF PHARMACEUTICAL R&D CO., LTD., Beijing (CN)

( * ) Notice: Subject to any disclaimer, the term of this patent is extended or adjusted under 35 U.S.C. 154(b) by 0 days.

(21) Appl. No.: 16/481,925

(22) PCT Filed: Dec. 26, 2017

(86) PCT No.: PCT/CN2017/118424
§ 371 (c)(1),
(2) Date: Jul. 30, 2019

(87) PCT Pub. No.: WO2018/145525
PCT Pub. Date: Aug. 16, 2018

(65) Prior Publication Data
US 2020/0062749 A1    Feb. 27, 2020

(30) Foreign Application Priority Data
Feb. 8, 2017  (CN) .......................... 201710068798.7

(51) Int. Cl.
| A61P 19/02 | (2006.01) |
| C07D 487/04 | (2006.01) |
| A61P 35/00 | (2006.01) |
| A61P 29/00 | (2006.01) |
| C07D 471/04 | (2006.01) |
| C07D 519/00 | (2006.01) |

(52) U.S. Cl.
CPC ............ *C07D 471/04* (2013.01); *A61P 19/02* (2018.01); *A61P 29/00* (2018.01); *A61P 35/00* (2018.01); *C07D 487/04* (2013.01); *C07D 519/00* (2013.01)

(58) Field of Classification Search
CPC .................................................. C07D 487/04
See application file for complete search history.

(56) References Cited

U.S. PATENT DOCUMENTS

2012/0094999 A1 * 4/2012 Gray ................... A61P 37/06
514/235.8

FOREIGN PATENT DOCUMENTS

| KR | 10-2016-0148262 | * 11/2016 | ........... B29C 45/561 |
| WO | 2006004833 A2 | 1/2006 | |
| WO | 2013008095 A1 | 1/2013 | |
| WO | 2013157021 A1 | 10/2013 | |
| WO | 2014025486 A1 | 2/2014 | |
| WO | WO 2018088780 | * 5/2018 | |

OTHER PUBLICATIONS

Stella (J. Pharmaceutical Sciences, 2010, 99(12), pp. 4755-4765).*
Meanwell et al. (J. Med. Chem., 2011, 54. pp. 2529-2591).*
King, Med. Chem., Principle and Practice (1994), pp. 206-208.*
King (Medicinal Chemistry: Principles and Practice, Chapter 14, pp. 206-225, (1994)).*
International Search Report for PCT/CN2017/118424 dated Mar. 28, 2018, 4 pages.

* cited by examiner

*Primary Examiner* — Susanna Moore
(74) *Attorney, Agent, or Firm* — Rothwell, Figg, Ernst & Manbeck, P.C.

(57) ABSTRACT

The present invention relates to pyrrolo-aromatic heterocyclic compounds, a preparation method therefor and medical use thereof. Particularly, the present invention relates to a compound represented by formula I, a preparation method therefor, a pharmaceutical composition comprising the compound, and use of the compound as a BTK kinase inhibitor. The compound and the pharmaceutical composition comprising same can be used for the treating diseases associated with BTK kinase activity, such as inflammations, autoimmune disorders, and cancers. The definition of each substituent in formula I is the same as that in the description.

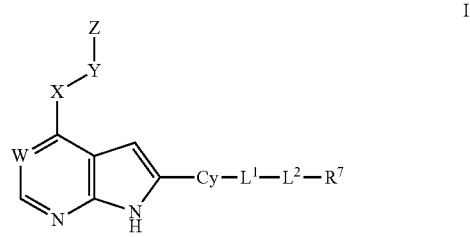

I

14 Claims, No Drawings

PYRROLO-AROMATIC HETEROCYCLIC COMPOUND, PREPARATION METHOD THEREFOR, AND MEDICAL USE THEREOF

CROSS REFERENCE TO RELATED APPLICATION(S)

This application is a 35 U.S.C. § 371 National Stage of International Patent Application No. PCT/CN2017/118424, filed Dec. 26, 2017, which claims priority to and the benefit of Chinese Patent Application No. 201710068798.7 filed on Feb. 8, 2017, respectively, the entire contents of which are incorporated herein by reference.

FIELD OF THE INVENTION

The present invention belongs to the technical field of medicine, and specifically relates to a novel pyrroloheteroaromatic compounds, the preparation process thereof, and the pharmaceutical composition comprising the same, as well as the use thereof for regulating the activity of Bruton's tyrosine kinase (BTK) and for treating and/or preventing the diseases associated with BTK activity.

BACKGROUND OF THE INVENTION

Cellular signaling pathway is an effective way of responding to external stimulus and facilitating specific biological effect. By enabling intracellular signal transduction via multiple pathways, cytokines are implicated in many biological functions, including cell proliferation regulation, hemopoiesis, and immune response. Bruton's tyrosine kinase (BTK) which is a member of tyrosine kinases, play an important role in signal transduction.

BTK family is a class of non-receptor tyrosine kinase. In 1952, Bruton observed X-linked agammaglobulinemia (XLA) patients with absence of mature B cells and failure to innate immune response, and the genetic research detected mutated BTK in X chromosomes of these patients, indicating a central role of BTK in maturation and development of B cells. BTK is regulated not only by B cell antigen receptor (BCR) pathway during immune response, but also by Toll like receptors (TLRs) pathway during inflammatory response.

BTK family members are mainly expressed in hemopoietic tissue and regulate the growth and differentiation of hemopoietic cells. BTK is mainly expressed in bone marrow derived cells and B cells, and is composed of 5 domains: PH domain for mediating membrane translocation, TH domain which consists of PRR and Btk motifs, SH2 and SH3 domains for facilitating the interaction between BTK and other proteins, and the kinase catalytic domain, SH1.

BTK is activated when interaction with phosphatidylinositol 3-kinase (PI3) or G protein-coupled receptors, and plays a significant role in angiogenesis, cell proliferation and apoptosis, and cell movement by the downstream signal cytokines, such as PLCγ2 (phospholipase C-γ2) and PKCI (ser-ine-threonine protein kinase βI). During the process of activation, the PH domain of BTK interacts with PIP3 to complete membrane translocation, followed by transphosphorylation of 2 tyrosine residues, Tyr551 and Tyr223. The Tyr551 residue on activation loop is phosphorylated by Src tyrosine kinase family, leading to the auto-phosphorylation of Tyr223 in SH3 domain, which is necessary for completed activation of BTK. This activation is down-regulated by PKCβ, which can reduce the membrane recruitment and transphophorylation of BTK by phosphorylating Ser180 of BTK, thereby reduce the activity. The PKC inhibitory signal is important to maintain the homeostasis of BTK activity in BCR signalling pathway.

As a key cytokine in BCR and TCR signaling pathway, BTK plays an important role in the pathogenesis of B cell malignancies. Several therapies targeting BTK have displayed efficacy in the treatment of various B cell malignancies. A number of BTK inhibitors have demonstrated efficacy in the clinical trials for chronic lymphpocytic leukemia (CLL), mantle cell lymphoma (MCL), diffuse large B-cell lymphoma (DLBCL), and multiple myeloma (MM). Moreover, the effect of BTK inhibitors on other B cell malignancies attracts the researchers' interests. For example, it is reported that MYD88 mutants and NF-κB signalling pathway are involved in the pathogenesis of splenic marginal zone lymphoma (MZL) and follicular lymphoma whose survival is associated with BCR antigen (and autoantigen). Notably, higher incidence of DLBCL and MZL has been observed in patients with systemic autoimmune diseases, and the activation of BTK pathway is an important pathological event of autoimmune diseases. Moreover, BTK inhibitors have shown potent effect in preclinical models. The protective effect of BTK in apoptosis of breast cancer cell lines has also been reported.

Rheumatic arthritis (RA) is an autoimmune disease, characterized by inflammation and destruction of joints. The disfunction of joint causes pain, disabilities, and even deaths, if the disease is not treated properly. Therefore, the purpose of RA treatment is not only to mitigate development, but also to alleviate symptoms, thereby prevent joint destruction. The worldwide prevalence of RA is about 0.8%, and 3-time higher in females than males. Up to now, RA is still incurable, and the current mainly focus on mitigating pain and preventing joint degeneration. The treatment strategy in clinic includes nonsteroidal antiinflammatory drugs (NSAIDs), steroids, disease-modifying anti-rheumatic drugs (MARDs) and biologics. The clinical use of DMARDs (such as methotrexate, hydroxychloroquine, leflunomide, and sulfasalazine) and DMARDs in combination with biologics could achieve a better efficacy. However, more than 30% patients are still suffering from pain in spite of many available anti-RA drugs. The recent researches indicate that interfering BTK pathway is becoming a new therapeutics of RA.

T cell has always been an attractive target for the treatment of RA because of its presence in synovial cavity and its capability of activating B cells. Although the blocking treatment of T cell co-stimulus has been approved, these T-cell-depleting therapeutics only demonstrate limited benefit in the treatment of RA. On the other hand, the function of B cells and the generation of autoantigens have been proved in the development of RA, resulting in the treatment of disease with B cells as target directly or indirectly. More importantly, the therapeutics reducing B cells significantly improved the clinical symptom of RA, indication a key role of B cells in the pathogenesis of RA. The effectiveness of B-cell targeting (reducing the number of B cells or inhibiting B cell survival) in RA demonstrates the important role of B cells in RA. BTK is implicated in the maturation and activation of B cells via BCR signalling pathway, and B cells with high expression of BTK show enhanced BCR pathway and induce overexpression of autoantigen, which thereby causes autoimmune diseases. Therefore, BTK is an ideal target for the treatment of autoimmune diseases including, but are not limited to RA, multiple sclerosis, lupus, psoriasis, psoriatic arthritis, inflammatory bowel disease, Crohn disease, uveitis, and sarcoidosis. A number of BTK inhibitors have shown excellent efficacy in the treatment of autoimmune diseases in preclinical animal models.

In the past years, BTK inhibitors development progresses faster. The approved drug Ibrutinib is mainly used in the treatment of B cell lymphomas. In addition to the treatment of B-cell lymphoma, CC-292 and ACP-196 in the middle and late stages of clinical development are still developing indications for autoimmune diseases such as RA. However, most of these BTK inhibitors have deficiencies of poor potency and selectivity, and considerable side effects. Therefore, there is consistent need for novel or improved inhibitors of kinase, such as BTK, to treat RA or other diseases associated with BTK.

SUMMARY OF THE INVENTION

The inventors have designed and synthesized a series of compounds containing a pyrroloheteroaromatic scaffold, and screened their activity against BTK kinase. The results show that these compounds have outstanding inhibitory activity against BTK and can be developed as a drug for the treatment of diseases associated with BTK kinase activity.

Thus, an object of the present invention is to provide a compound of formula I, or a mesomer, racemate, enantiomer, diastereomer, or mixture thereof, a prodrug or a pharmaceutically acceptable salt thereof,

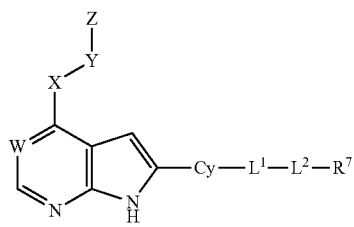

wherein
W is selected from N and $CR^1$;
$R^1$ is selected from the group consisting of H, halogen, cyano and alkyl;
X is selected from the group consisting of —O—, —$NR^2$—, —$CH_2$—, —S—, —SO—, —$SO_2$—, and —CO—;
$R^2$ is selected from the group consisting of H, alkyl and cycloalkyl; wherein said alkyl or cycloalkyl is optionally further substituted with one or more groups selected from the group consisting of halogen, amino, nitro, cyano, oxo, hydroxyl, thiol, carboxyl, ester, alkyl, alkoxyl, alkenyl, alkynyl, cycloalkyl, heterocyclyl, aryl, and heteroaryl;
Y is selected from aryl and heteroaryl, wherein said aryl or heteroaryl is optionally further substituted with one or more groups selected from the group consisting of halogen, amino, nitro, cyano, oxo, hydroxyl, thiol, carboxyl, ester, alkyl, alkoxyl, haloalkyl, haloalkoxyl, alkenyl, alkynyl, cycloalkyl, heterocyclyl, aryl, and heteroaryl;
Z is

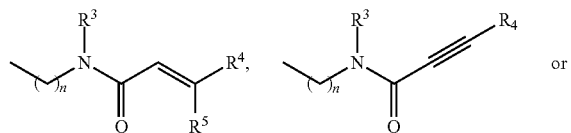

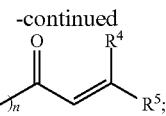

n is an integer from 0 to 4;
$R^3$ is selected from H, alkyl and cycloalkyl; wherein said alkyl or cycloalkyl is optionally further substituted with one or more groups selected from the group consisting of halogen, amino, nitro, cyano, oxo, hydroxyl, thiol, carboxyl, ester, alkyl, alkoxyl, alkenyl, alkynyl, cycloalkyl, heterocyclyl, aryl and heteroaryl;
$R^4$ and $R^5$ are each independently selected from H and alkyl, wherein said alkyl is optionally further substituted with one or more groups selected from the group consisting of heterocyclyl and —$NR^aR^b$, wherein said heterocyclyl is optionally further substituted with halogen or alkyl;
Cy is selected from aryl and heteroaryl, wherein said aryl or heteroaryl is optionally further substituted with one or more groups selected from the group consisting of halogen, amino, nitro, cyano, hydroxyl, thiol, carboxyl, ester, oxo, alkyl, alkoxyl, alkenyl, alkynyl, cycloalkyl, heterocyclyl, aryl, heteroaryl, haloalkyl and haloalkoxy;
$L^1$ and $L^2$ are each independently selected from the group consisting of a single bond, —$(CH_2)_m$—, —O—, —$NR^6$—, —S—, —SO—, —$SO_2$— and —CO—;
m is an integer from 0 to 4;
$R^6$ is selected from H, alkyl and cycloalkyl, wherein said alkyl or cycloalkyl is optionally further substituted with one or more groups selected from the group consisting of halogen, amino, nitro, cyano, oxo, hydroxyl, thiol, carboxyl, ester, alkyl, alkoxyl, alkenyl, alkynyl, cycloalkyl, heterocyclyl, aryl, and heteroaryl;
$R^7$ is selected from alkyl, cycloalkyl and heterocyclyl, wherein said alkyl, cycloalkyl or heterocyclyl is optionally further substituted with one or more $R^8$;
each $R^8$ is independently selected from the group consisting of halogen, amino, nitro, cyano, hydroxyl, thiol, oxo, alkyl, alkoxyl, cycloalkyl, heterocyclyl, aryl, heteroaryl, —C(O)$R^a$, —O(O)C$R^a$, —C(O)O$R^a$, —C(O)$NR^aR^b$, —NHC(O)$R^a$, —S(O)$R^a$, —S(O)$_2R^a$, —S(O)$NR^aR^b$, —$NR^aR^b$, —S(O)$_2NR^aR^b$, —NHS(O)$R^a$, and —NHS(O)$_2R^a$; wherein said alkyl, alkoxyl, cycloalkyl, heterocyclyl, aryl or heteroaryl is optionally further substituted with one or more groups selected from the group consisting of halogen, amino, nitro, cyano, oxo, hydroxyl, thiol, carboxyl, ester, alkyl, alkoxyl, alkenyl, alkynyl, cycloalkyl, heterocyclyl, aryl, and heteroaryl;
$R^a$ and $R^b$ are each independently selected from the group consisting of H, halogen, hydroxyl, alkyl, alkenyl, alkynyl, cycloalkyl, heterocyclyl, aryl, and heteroaryl, wherein said alkyl, alkenyl, alkynyl, cycloalkyl, heterocyclyl, aryl or heteroaryl is optionally further substituted with one or more groups selected from the group consisting of halogen, amino, nitro, cyano, hydroxyl, thiol, carboxyl, ester, oxo, alkyl, alkoxyl, alkenyl, alkynyl, cycloalkyl, heterocyclyl, aryl and heteroaryl; or
$R^a$ and $R^b$, together with the nitrogen atom attached to them, form a N-containing heterocyclic group, wherein said N-containing heterocyclic group is optionally further substituted with one or more groups selected from the group consisting of halogen, amino, nitro, cyano, oxo, hydroxyl, thiol, carboxyl, ester, alkyl, alkoxyl, alkenyl, alkynyl, cycloalkyl, heterocyclyl, aryl and heteroaryl.

In a preferred embodiment, the compound of formula I, a mesomer, racemate, enantiomer, diastereomer, or mixture thereof, a prodrug or a pharmaceutically acceptable salt thereof according to the invention, wherein, X is selected from —O—, —S— and —NR²—, R² is selected from H, alkyl and cycloalkyl; said alkyl is preferably $C_1$-$C_{12}$ alkyl, more preferably $C_1$-$C_6$ alkyl; said cycloalkyl is preferably $C_3$-$C_{12}$ cycloalkyl, more preferably $C_3$-$C_6$ cycloalkyl.

In another preferred embodiment, the compound of formula I, or a mesomer, racemate, enantiomer, diastereomer, or mixture thereof, a prodrug or a pharmaceutically acceptable salt thereof according to the invention, wherein, Y is selected from $C_6$-$C_{10}$ aryl and 5-10 membered heteroaryl, preferably phenyl or pyridyl; wherein said aryl or heteroaryl is optionally further substituted with one or more groups selected from the group consisting of halogen, cyano, alkyl, alkoxyl, haloalkyl, and haloalkoxyl; said alkyl is preferably $C_1$-$C_{12}$ alkyl, more preferably $C_1$-$C_6$ alkyl; said alkoxyl is preferably $C_1$-$C_{12}$ alkoxyl, more preferably $C_1$-$C_6$ alkoxyl.

In another preferred embodiment, the compound of formula I, or a mesomer, racemate, enantiomer, diastereomer, or mixture thereof, a prodrug or a pharmaceutically acceptable salt thereof according to the invention, wherein, Z is

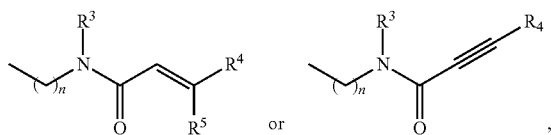

n is 0;

R³ is selected from H, alkyl and cycloalkyl;

R⁴ and R⁵ are each independently selected from H and alkyl, wherein said alkyl is optionally further substituted with one or more groups selected from —NRᵃRᵇ;

Rᵃ and Rᵇ are each independently selected from H, alkyl and cycloalkyl; or

Rᵃ and Rᵇ, together with the nitrogen atom attached to them, form a 5-7 membered N-containing heterocyclic group, wherein said N-containing heterocyclic group is optionally further substituted with one or more groups selected from the group consisting of halogen, oxo, alkyl and alkoxyl;

the alkyl is preferably $C_1$-$C_{12}$ alkyl, more preferably $C_1$-$C_6$ alkyl;

the cycloalky is preferably $C_3$-$C_{12}$ cycloalky, more preferably $C_3$-$C_6$ cycloalky;

the 5-7 membered N-containing heterocyclic group is preferably pyrrolidinyl, tetrahydroimidazolyl, tetrahydropyrazolyl, tetrahydrooxazolyl, tetrahydrothiazolyl, piperidinyl, piperazinyl, or morpholinyl.

In another preferred embodiment, the compound of formula I, or a mesomer, racemate, enantiomer, diastereomer, or mixture thereof, a prodrug or a pharmaceutically acceptable salt thereof according to the invention, wherein, Z is

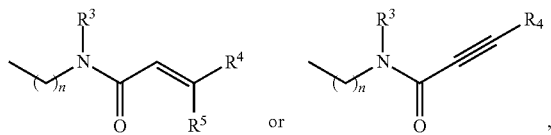

n is 0;

R³ is selected from H, alkyl and cycloalkyl;

R⁴ and R⁵ are each independently selected from H and alkyl, wherein said alkyl is optionally further substituted with one or more groups selected from the group consisting of heterocyclyl, wherein said heterocyclyl is optionally further substituted with halogen or alkyl;

the alkyl is preferably $C_1$-$C_{12}$ alkyl, more preferably $C_1$-$C_6$ alkyl;

the cycloalky is preferably $C_3$-$C_{12}$ cycloalky, more preferably $C_3$-$C_6$ cycloalky;

the heterocyclyl is preferably 3-8 membered heterocyclyl, more preferably tetrahydrofuranyl, tetrahydrothiophenyl, tetrahydrooxazolyl, or tetrahydrothiazolyl.

In another preferred embodiment, the compound of formula I, or a mesomer, racemate, enantiomer, diastereomer, or mixture thereof, a prodrug or a pharmaceutically acceptable salt thereof according to the invention, which is a compound of formula II or a mesomer, racemate, enantiomer, diastereomer, or mixture thereof, a prodrug or a pharmaceutically acceptable salt thereof,

II

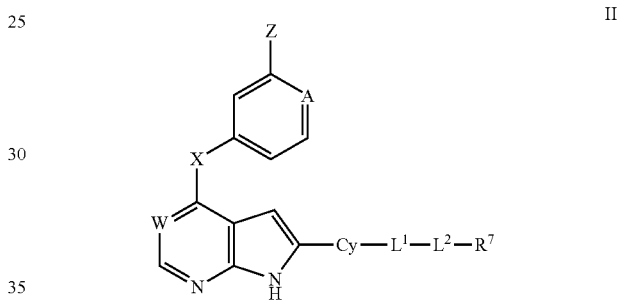

wherein,

W is selected from N and CR¹;

R¹ is selected from the group consisting of H, halogen, cyano and alkyl;

A is selected from N and CRᶜ;

Rᶜ is selected from the group consisting of H, halogen, cyano, alkyl, alkoxyl, haloalkyl, and haloalkoxyl;

X is selected from the group consisting of —O—, —S—, and —NR²—;

R² is selected from the group consisting of H, alkyl and cycloalkyl;

Z is

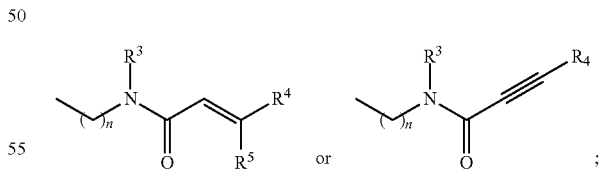

n is 0;

R³ is selected from the group consisting of H, alkyl and cycloalkyl;

R⁴ and R⁵ are each independently selected from H and alkyl, wherein said alkyl is optionally further substituted with one or more groups selected from —NRᵃRᵇ;

Rᵃ and Rᵇ are each independently selected from the group consisting of H, alkyl and cycloalkyl; or Rᵃ and Rᵇ, together with the nitrogen atom attached to them, form a 5 to 7 membered N-containing heterocyclic group;

the alkyl is preferably $C_1$-$C_{12}$ alkyl, more preferably $C_1$-$C_6$ alkyl;

the alkoxyl is preferably $C_1$-$C_{12}$ alkoxyl, more preferably $C_1$-$C_6$ alkoxyl;

the cycloalky is preferably $C_3$-$C_{12}$ cycloalky, more preferably $C_3$-$C_6$ cycloalky;

the 5-7 membered N-containing heterocyclic group is preferably pyrrolidinyl, tetrahydroimidazolyl, tetrahydropyrazolyl, tetrahydrooxazolyl, tetrahydrothiazolyl, piperidinyl, piperazinyl, or morpholinyl;

Cy, $L^1$, $L^2$, $R^7$ are as defined in formula I.

In another preferred embodiment, the compound of formula I, or a mesomer, racemate, enantiomer, diastereomer, or mixture thereof, a prodrug or a pharmaceutically acceptable salt thereof according to the invention, which is a compound of formula III or a mesomer, racemate, enantiomer, diastereomer, or mixture thereof, a prodrug or a pharmaceutically acceptable salt thereof,

III

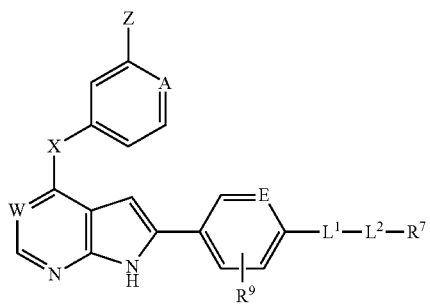

wherein,

W is selected from N and $CR^1$;

$R^1$ is selected from the group consisting of H, halogen, cyano and alkyl;

A is selected from N and $CR^c$;

$R^c$ is selected from the group consisting of H, halogen, cyano, alkyl, alkoxyl, haloalkyl, and haloalkoxyl;

X is selected from the group consisting of —O—, —S—, and —$NR^2$—;

$R^2$ is selected from the group consisting of H, alkyl and cycloalkyl;

Z is

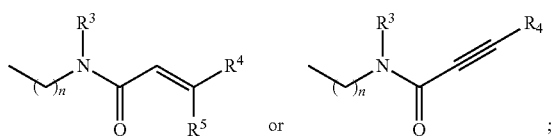

n is 0;

$R^3$ is selected from the group consisting of H, alkyl and cycloalkyl;

$R^4$ and $R^5$ are each independently selected from H and alkyl, wherein said alkyl is optionally further substituted with one or more groups selected from —$NR^aR^b$;

$R^a$ and $R^b$ are each independently selected from the group consisting of H, alkyl and cycloalkyl; or $R^a$ and $R^b$, together with the nitrogen atom attached to them, form a 5-7 membered N-containing heterocyclic group;

E is selected from N and $CR^d$;

$R^d$ is selected from the group consisting of H, halogen, cyano, alkyl, alkoxyl, haloalkyl, and haloalkoxyl;

$R^9$ is selected from the the group consisting of H, halogen, alkyl, alkoxyl, haloalkyl and haloalkoxyl;

$L^1$ and $L^2$ are each independently selected from one or more groups selected from the group consisting of a single bond, —$(CH_2)_m$—, —O—, —$NR^6$—, —S—, —SO—, —$SO_2$—, and —CO—; preferably -$L^1$-$L^2$- is selected from the group consisting of a single bond, —$(CH_2)_m$—, —O—, —$NR^6$—, —S—, —SO—, —$SO_2$—, —CO—, —NH—CO—, —NH—$SO_2$—, —$CH_2$—O—, —$CH_2$—S—, —$CH_2$—CO—, —$CH_2$—$SO_2$—, —$NR^6$—$(CH_2)_m$—$NR^6$, —O—$(CH_2)_m$—O—, —$CH_2$—$NR^6$— and —CO—$NR^6$—;

m is an integer from 1 to 4;

$R^6$ is selected from the group consisting of H, alkyl and cycloalkyl;

$R^7$ is selected from the group consisting of alkyl, cycloalkyl and heterocyclyl, wherein said alkyl, cycloalkyl or heterocyclyl is optionally further substituted with one or more $R^8$;

each $R^8$ is independently selected from the group consisting of halogen, cyano, oxo, alkyl, alkoxyl, —C(O)$R^a$, —C(O)OR$^a$, —S(O)$R^a$, and —S(O)$_2R^a$, wherein said alkyl or alkoxyl is optionally further substituted with halogen;

$R^a$ is selected from H and alkyl;

the alkyl is preferably $C_1$-$C_{12}$ alkyl, more preferably $C_1$-$C_6$ alkyl;

the alkoxyl is preferably $C_1$-$C_{12}$ alkoxyl, more preferably $C_1$-$C_6$ alkoxyl;

the cycloalky is preferably $C_3$-$C_{12}$ cycloalky, more preferably $C_3$-$C_6$ cycloalky;

the heterocyclyl is preferably 5-8 membered heterocyclyl, more preferably pyrrolidinyl, tetrahydroimidazolyl, tetrahydropyrazolyl, tetrahydrooxazolyl, tetrahydrothiazolyl, piperidinyl, piperazinyl, morpholinyl, thiomorpholinyl, tetrahydrofuranyl, tetrahydrothiophenyl,

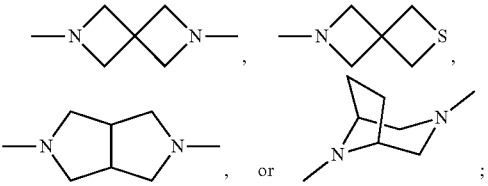

W, X, A, Z are as defined in formula II.

In another preferred embodiment, the compound of formula I, or a mesomer, racemate, enantiomer, diastereomer, or mixture thereof, a prodrug or a pharmaceutically acceptable salt thereof according to the invention, which is a compound of formula IV or a mesomer, racemate, enantiomer, diastereomer, or mixture thereof, a prodrug or a pharmaceutically acceptable salt thereof,

IV

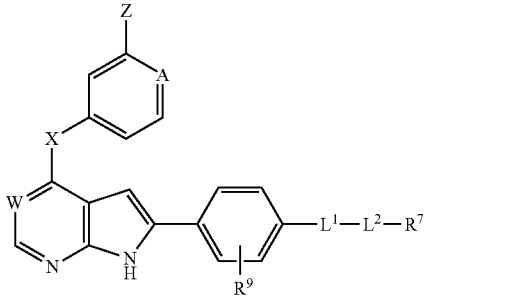

wherein,

W is selected from N and CR$^1$;

R$^1$ is selected from the group consisting of H, halogen, cyano and alkyl;

X is selected from the group consisting of —O—, —NR$^2$— and —S—;

R$^2$ is selected from the group consisting of H, alkyl and cycloalkyl;

A is selected from N and CR$^c$;

R$^c$ is selected from the group consisting of H, halogen, cyano, alkyl, alkoxyl, haloalkyl;

Z is selected from the group consisting of

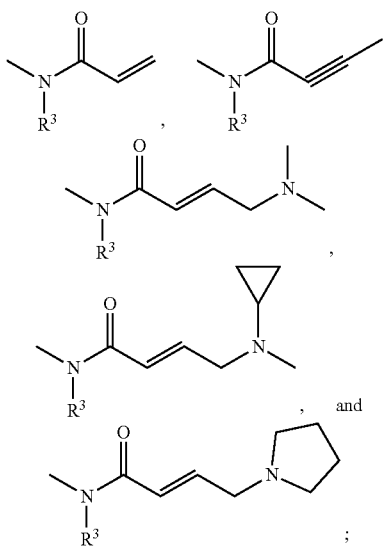

R$^3$ is selected from the group consisting of H, alkyl and cycloalkyl;

R$^9$ is selected from the group consisting of H, halogen, alkyl, alkoxyl, haloalkyl, and haloalkoxyl;

L$^1$ and L$^2$ are each independently selected from one or more groups selected from the group consisting of a single bond, —(CH$_2$)$_m$—, —O—, —NR$^6$—, —S—, —SO—, —SO$_2$—, and —CO—;

m is an integer from 1 to 4;

R$^6$ is selected from the group consisting of H, alkyl and cycloalkyl;

R$^7$ is selected from the group consisting of alkyl, cycloalkyl and heterocyclyl, wherein said alkyl, cycloalkyl or heterocyclyl is optionally further substituted with one or more R$^8$;

each R$^8$ is independently selected from the group consisting of halogen, oxo, alkyl, and —COOH, wherein said alkyl is optionally further substituted with halogen;

wherein, -L$^1$-L$^2$- is preferably selected from the group consisting of a single bond, —(CH$_2$)$_m$—, —O—, —NR$^6$—, —S—, —SO—, —SO$_2$—, —CO—, —NH—CO—, —NH—SO$_2$—, —CH$_2$—O—, —CH$_2$—S—, —CH$_2$—CO—, —CH$_2$—SO$_2$—, —NR$^6$—(CH$_2$)$_m$—NR$^6$, —O—(CH$_2$)$_m$—O—, —CH$_2$—NR$^6$—, and —CO—NR$^6$—;

the heterocyclyl is preferably 5-8 membered heterocyclyl, more preferably pyrrolidinyl, tetrahydroimidazolyl, tetrahydropyrazolyl, tetrahydrooxazolyl, tetrahydrothiazolyl, piperidinyl, piperazinyl, morpholinyl, thiomorpholinyl, tetrahydrofuranyl, tetrahydrothiophenyl,

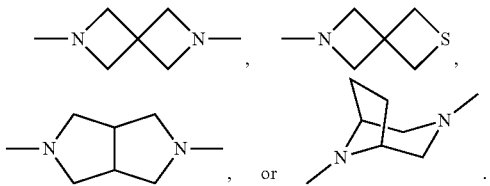

Typical compounds of the invention include, but are not limited to:

N-(3-((5-chloro-2-(4-(4-methylpiperazin-1yl)phenyl)-1H-pyrrolo[2,3-b]pyridin-4-yl)oxy)phenyl)acrylamide;

N-(3-((5-fluoro-2-(4-(4-methylpiperazin-1yl)phenyl)-1H-pyrrolo[2,3-b]pyridin-4-yl)oxy)phenyl)acrylamide;

N-(3-((5-cyano-2-(4-(4-methylpiperazin-1yl)phenyl)-1H-pyrrolo[2,3-b]pyridin-4-yl)oxy)phenyl)acrylamide;

N-(3-((5-methyl-2-(4-(4-methylpiperazin-1yl)phenyl)-1H-pyrrolo[2,3-b]pyridin-4-yl)oxy)phenyl)acrylamide;

N-(3-((6-(4-(4-methylpiperazin-1-yl)phenyl)-7H-pyrrolo[2,3-b]pyrimidin-4-yl)amino)phenyl)acrylamide;

N-(3-((6-(4-(4-methylpiperazin-1-yl)phenyl)-H-pyrrolo)phenyl) but-2-ynylamide;

N-(2-fluoro-5-((6-(4-(4-methylpiperazin-1-yl)phenyl)-7H-pyrrolo[2,3-d]pyrimidin-4-yl)oxy)phenyl)but-2-ynylamide;

4-(dimethylamino)-N-(3-((6-(4-(4-methylpiperazin-1-yl)phenyl)-7H-pyrrolo[2,3-d]pyrimidin-4-yl)oxy)phenyl)but-2-enamide;

4-(dimethylamino)-N-(2-fluoro-5-((6-(4-(4-methylpiperazin-1-yl)phenyl)-7H-pyrrolo[2,3-d]pyrimidin-4-yl)oxy)phenyl)but-2-enamide;

4-(cyclopropyl(methyl)amino-N-(3-((6-(4-(4-methylpiperazin-1-yl)phenyl)-7H-pyrrolo[2,3-d]pyrimidin-4-yl)oxy)phenyl)but-2-enamide;

N-(3-((6-(4-(4-methylpiperazin-1-yl)phenyl)-7H-pyrrolo[2,3-d]pyrimidin-4-yl)oxy)phenyl)-4-(pyrrolidin-1-yl)but-2-enamide;

N-(3-((6-(4-(4-methylpiperazin-1-yl)phenyl)-7H-pyrrolo[2,3-d]pyrimidin-4-yl)oxy)phenyl) acrylamide;

N-(3-((6-(4-(4-methylpiperazin-1-yl)phenyl)-7H-pyrrolo[2,3-d]pyrimidin-4-yl)thio)phenyl) acrylamide;

N-(3-(methyl(6-(4-(4-methylpiperazin-1-yl)phenyl)-7H-pyrrolo[2,3-d]pyrimidin-4-yl)amino)phenyl) acrylamide;

N-methyl-N-(3-((6-(4-(4-methylpiperazin-1-yl)phenyl)-7H-pyrrolo[2,3-d]pyrimidin-4-yl)oxy)phenyl)acrylamide;

N-methyl-N-(3-((6-(4-morpholinylphenyl)-7H-pyrrolo[2,3-d]pyrimidin-4-yl)oxy)phenyl)acrylamide;

N-cyclopropyl-N-(3-((6-(4-(4-methylpiperazin-1-yl)phenyl)-7H-pyrrolo[2,3-d]pyrimidin-4-yl)oxy)phenyl)acrylamide;

N-(2-fluoro-5-((6-(4-(4-methylpiperazin-1-yl)phenyl)-7H-pyrrolo[2,3-d]pyrimidin-4-yl)oxy) phenyl)acrylamide;

N-(2-fluoro-5-((6-(4-morpholinylphenyl)-7H-pyrrolo[2,3-d]pyrimidin-4-yl)oxy)phenyl)acrylamide;

N-(4-((6-(4-morpholinylphenyl)-7H-pyrrolo[2,3-d]pyrimidin-4-yl)oxy)pyridin-2-yl)acrylamide;

N-(2-methyl-5-((6-(4-morpholinylphenyl)-7H-pyrrolo[2,3-d]pyrimidin-4-yl)oxy)phenyl)acrylamide;

N-(2-methoxy-5-((6-(4-(4-methylpiperazin-1-yl)phenyl)-7H-pyrrolo[2,3-d]pyrimidin-4-yl)oxy)phenyl)acrylamide;

N-(2-cyano-5-((6-(4-(4-methylpiperazin-1-yl)phenyl)-7H-pyrrolo[2,3-d]pyrimidin-4-yl)oxy)phenyl)acrylamide;

N-(3-((6-(6-(4-methylpiperazin-1-yl)pyridin-3-yl)-7H-pyrrolo[2,3-d]pyrimidin-4-yl)oxy)phenyl)acrylamide;

N-(3-((6-(3-fluoro-4-(4-methylpiperazin-1-yl)phenyl)-7H-pyrrolo[2,3-d]pyrimidin-4-yl)oxy) phenyl)acrylamide;
N-(3-((6-(3-methoxy-4-(4-methylpiperazin-1-yl)phenyl)-7H-pyrrolo[2,3-d]pyrimidin-4-yl)oxy)phenyl)acrylamide;
N-(3-((6-(3-methyl-4-(4-methylpiperazin-1-yl)phenyl)-7H-pyrrolo[2,3-d]pyrimidin-4-yl)oxy)phenyl)acrylamide;
N-(3-((6-(3-(difluoromethoxy)-4-(4-methylpiperazin-1-yl)phenyl)-7H-pyrrolo[2,3-d]pyrimidine-4-yl)oxy)phenyl)acrylamide;
N-(3-((6-(4-(dimethylamino)phenyl)-7H-pyrrolo[2,3-d]pyrimidin-4-yl)oxy)phenyl)acrylamide;
N-(3-((6-(4-((dimethylamino)methyl)phenyl)-7H-pyrrolo[2,3-d]pyrimidin-4-yl)oxy)phenyl)acrylamide;
N-(3-((6-(4-(2-methoxyethoxy)phenyl)-7H-pyrrolo[2,3-d]pyrimidin-4-yl)oxy)phenyl)acrylamide;
N-(3-((6-(4-morpholinylphenyl)-7H-pyrrolo[2,3-d]pyrimidin-4-yl)amino)phenyl)acrylamide;
N-(3-((6-(4-morpholinylphenyl)-7H-pyrrolo[2,3-d]pyrimidin-4-yl)oxy)phenyl)acrylamide;
N-(3-((6-(4-(piperazin-1-yl)phenyl)-7H-pyrrolo[2,3-d]pyrimidin-4-yl)oxy)phenyl)acrylamide;
N-(3-((6-(4-(1,1-dioxothiomorpholinyl)phenyl)-7H-pyrrolo[2,3-d]pyrimidine-4-yl)oxy)phenyl) acrylamide;
N-(3-((6-(4-(4-(2,2,2-trifluoroethyl)piperazin-1-yl)phenyl)-7H-pyrrolo[2,3-d]pyrimidin-4-yl)oxy)phenyl)acrylamide;
N-(3-((6-(4-(6-methyl-2,6-diazaspiro[3.3]heptan-2-yl)phenyl)-7H-pyrrolo[2,3-d]pyrimidin-4-yl)oxy)phenyl)acrylamide;
N-(3-((6-(4-(2-thio-6-azaspiro[3.3]heptan-6-yl)phenyl)-7H-pyrrolo[2,3-d]pyrimidin-4-yl)oxy)phenyl)acrylamide;
N-(3-((6-(4-(4-acetylpiperazin-1-yl)phenyl)-7H-pyrrolo[2,3-d]pyrimidin-4-yl)oxy)phenyl)acrylamide;
N-(3-((6-(4-(2,4-dimethylpiperazin-1-yl)phenyl)-7H-pyrrolo[2,3-d]pyrimidin-4-yl)oxy)phenyl)acrylamide;
1-(4-(4-(3-acrylamidophenoxy)-7H-pyrrolo[2,3-d]pyrimidin-6-yl)phenyl)-4-methylpiperazine-2-carboxylic acid;
N-(3-((6-(4-(4,4-difluoropiperidin-1-yl)phenyl)-7H-pyrrolo[2,3-d]pyrimidin-4-yl)oxy)phenyl) acrylamide;
N-(3-((6-(4-(5-methylhexahydropyrrolo[3,4-c]pyrrol-2(1H)-yl)phenyl)-7H-pyrrolo[2,3-d]pyrimidin-4-yl)oxy)phenyl)acrylamide;
N-(3-((6-(4-((1,1-dioxothiomorpholinyl)methyl)phenyl)-7H-pyrrolo[2,3-d]pyrimidin-4-yl)oxy)phenyl)acrylamide;
N-(3-((6-(4-((1,1-dioxothiomorpholinyl)methyl)phenyl)-7H-pyrrolo[2,3-d]pyrimidin-4-yl)amino)phenyl) acrylamide;
N-(3-((6-(4-(morpholinomethyl)phenyl)-7H-pyrrolo[2,3-d]pyrimidin-4-yl)oxy)phenyl)acrylamide;
N-(3-((6-(4-((4,4-difluoropiperidin-1-yl)methyl)phenyl)-7H-pyrrolo[2,3-d]pyrimidin-4-yl)oxy)phenyl) acryl amide;
N-(3-((6-(4-(piperidin-1-ylmethyl)phenyl)-7H-pyrrolo[2,3-d]pyrimidin-4-yl)oxy)phenyl)acrylamide;
N-(3-((6-(4-(pyrrolidin-1-ylmethyl)phenyl)-7H-pyrrolo[2,3-d]pyrimidin-4-yl)oxy)phenyl)acrylamide;
N-(3-((6-(4-((6-methyl-2,6-diazaspiro[3.3]heptan-2-yl)methyl)phenyl)-7H-pyrrolo[2,3-d]pyrimidin-4-yl)oxy)phenyl)acrylamide;
N-(3-((6-(4-((5-methylhexahydropyrrolo[3,4-c]pyrrol-2(1H)-yl)methyl)phenyl)-7H-pyrrolo[2,3-d]pyrimidin-4-yl)oxy)phenyl)acrylamide;
N-(3-((6-(4-(3-methyl-3,8-diazabicyclo[3.2.1]octane-8yl)methyl)phenyl)-7H-pyrrolo[2,3-d]pyrimidin-4-yl)oxy)phenyl)acrylamide;
N-(3-((6-(4-((1-methylpiperidin-4-yl)amino)phenyl)-7H-pyrrolo[2,3-d]pyrimidin-4-yl)oxy)phenyl)acrylamide;
N-(3-((6-(4-(morpholin-4-formyl)phenyl)-7H-pyrrolo[2,3-d]pyrimidin-4-yl)oxy)phenyl) acrylamide;
N-(3-((6-(4-((1-methylpiperidin-4-yl)oxy)phenyl)-7H-pyrrol[2,3-d]pyrimidin-4-yl)oxy)phenyl)acrylamide;
N-(3-((6-(4-(methyl(1-methylpiperidin-4-yl)amino)phenyl)-7H-pyrrolo[2,3-d]pyrimidin-4-yl)oxy)phenyl)acrylamide;
N-(3-((6-(4-(4-methylpiperazin-1-yl)sulfonyl)phenyl)-7H-pyrrolo[2,3-d]pyrimidin-4-yl)oxy)phenyl)acrylamide;
N-(3-((6-(4-((1-methylpiperidin-4-yl)oxy)methyl)phenyl)-7H-pyrrolo[2,3-d]pyrimidin-4-oxy)phenyl)acrylamide;
N-(3-((6-(4-(((1-methylpiperidin-4-yl)amino)methyl)phenyl))-7H-pyrrolo[2,3-d]pyrimidin-4-yl)oxy)phenyl)acrylamide;
N-(3-((6-(4-((methyl(1-methylpiperidin-4-yl)amino)methyl))phenyl)-7H-pyrrolo[2,3-d]pyrimidin-4-yl)oxy) phenyl)acrylamide;
N-(4-(4-(3-acrylamidophenoxy)-7H-pyrrolo[2,3-d]pyrimidin-6-yl)phenyl)-1-methylpiperidin-4-ylcarbamate;
N-(3-((6-(4-(4-(ethylsulfonyl)piperazin-1-yl)phenyl)-7H-pyrrolo[2,3-d]pyrimidin-4-yl)oxy)phenyl)acrylamide;
N-(3-((6-(4-((4,4-difluoropiperidin-1-yl)methyl)phenyl)-7H-pyrrolo[2,3-d]pyrimidin-4-yl)oxy)phenyl)but-2-ynylamide;
N-(3-((6-(4-piperidin-1-ylmethyl)phenyl)-7H-pyrrolo[2,3-d]pyrimidin-4-yl)oxy)phenyl) but-2-ynylamide;
or a mesomer, racemate, enantiomer, diastereomer, or mixture thereof, a prodrug or a pharmaceutically acceptable salt thereof.

Another aspect of the invention is to provide a method for the preparation of the compound of formula I, or or a mesomer, racemate, enantiomer, diastereomer, or mixture thereof, a prodrug or a pharmaceutically acceptable salt thereof according to the invention, which comprises the steps of:

1) when W is N,

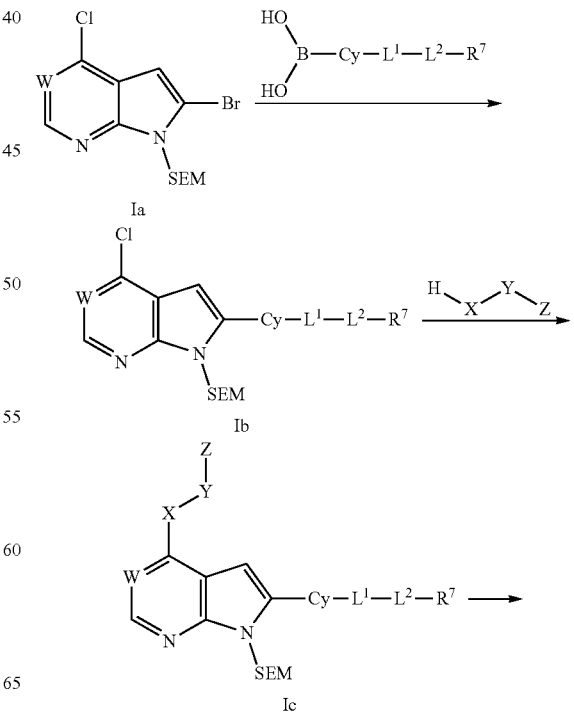

-continued

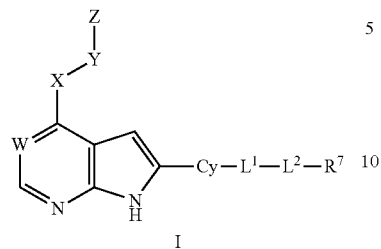

step a) compound Ia is reacted with the corresponding boronic acid in the presence of catalyst under basic and high-temperature condition to obtain compound Ib; wherein the basic reagent is preferably potassium carbonate or sodium carbonate, the catalyst is preferably Pd(dppf)Cl$_2$ or Pd(PPh$_3$)$_4$, and the temperature is preferably selected from 80° C.-100° C.;

step b) compound Ib is reacted with H—X—Y—Z under basic and high-temperature condition to obtain compound Ic; wherein the basic reagent is preferably potassium carbonate, and the temperature is preferably selected from 80° C.-120° C.;

step c) compound Ic is subjected to acid and then aqueous ammonia treatment to obtain the compound of formula I; wherein the acid is preferably trifluoroacetic acid;

2) when W is CR$^1$,

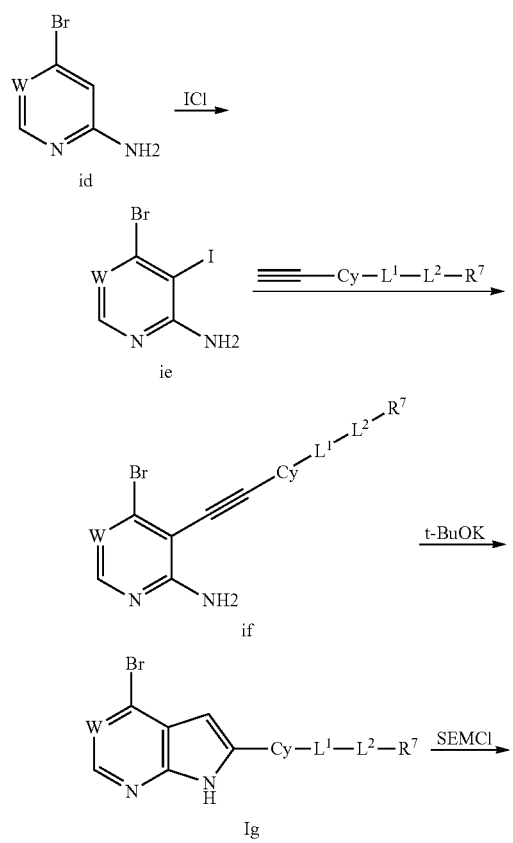

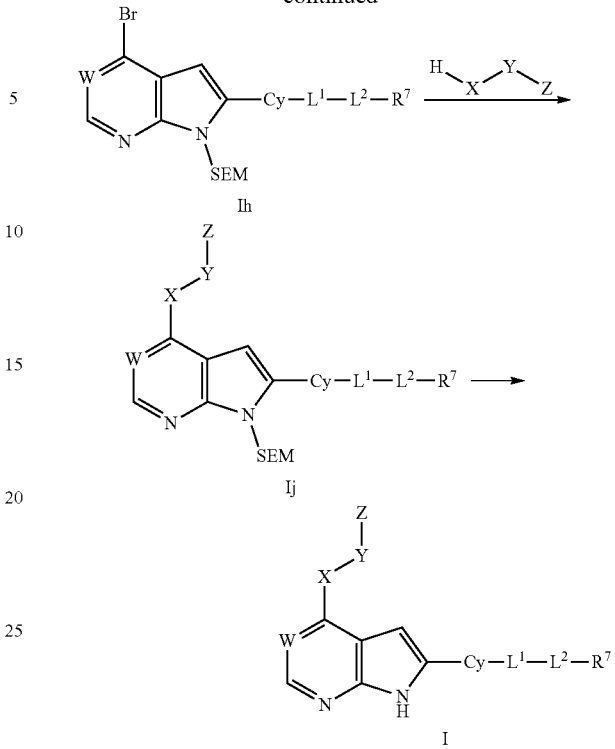

Step d) compound Id is reacted with ICl under high-temperature condition to obtain compound Ie, wherein the temperature is preferably 40° C.;

Step e) compound Ie is subjected to Sonogashina coupling reaction with the corresponding alkyne compounds in the presence of catalyst under basic condition to obtain compound If; wherein the basic reagent is preferably trimethylamine, the catalyst is preferably selected from Pd(Ph$_3$P)$_2$Cl$_2$ and CuI;

Step f) compound If is subjected to cyclization reaction under high-temperature and basic condition to obtain compound Ig, wherein the basic reagent is preferably potassium t-butoxide, and the temperature is preferably 70° C.;

Step g) compound Ig is reacted with SEMCl under basic condition to obtain compound Ih; wherein the basic reagent is preferably NaH;

Step h) compound Ih is reacted with H—X—Y—Z under high-temperature and basic condition to obtain compound Ij; wherein the basic reagent is preferably potassium carbonate, the temperature is preferably selected from 80-120° C.;

Step i) compound Ij is subjected to acid and then aqueous ammonia treatment to obtain the compound of formula I; wherein the acid is preferably trifluoroacetic acid;

wherein, W, X, Y, Z, Cy, L$^1$, L$^2$, R$^1$ and R$^7$ are as defined in formula I.

Another aspect of the present invention relates to a pharmaceutical composition comprising an effective amount of the compound of formula I or a mesomer, racemate, enantiomer, diastereomer, or mixture thereof, a prodrug or a pharmaceutically acceptable salt thereof, and a pharmaceutically acceptable carrier, diluent or excipient. The present invention also relates to a process for the preparation of the above composition, which comprises admixing the compound of formula I or a mesomer, racemate, enantiomer, diastereomer, or mixture thereof, a prodrug or a pharmaceutically acceptable salt thereof with the pharmaceutically acceptable carrier, diluent or excipient.

The present invention further relates to use of the compound of formula I or a mesomer, racemate, enantiomer, diastereomer, or mixture thereof, a prodrug or a pharmaceutically acceptable salt, or a pharmaceutical composition comprising the same in the preparation of BTK kinase inhibitors.

The present invention further relates to use of the compound of formula I or a mesomer, racemate, enantiomer, diastereomer, or mixture thereof, a prodrug or a pharmaceutically acceptable salt thereof, or a pharmaceutical composition comprising the same in preparation of medicaments for the prevention and/or treatment of disease associated with BTK kinase activity. The disease associated with BTK activity may be selected from inflammation, autoimmune disease, and cancer, wherein the inflammation is for example, arthritis, particularly rheumatoid arthritis, psoriatic arthritis, inflammatory bowel disease, or Uveitis; the autoimmune disease is for example, multiple sclerosis, lupus, psoriasis, or sarcoidosis; the cancer is for example breast cancer, cervical cancer, colon cancer, lung cancer, stomach cancer, rectal cancer, pancreatic cancer, brain cancer, skin cancer, oral cancer, prostate cancer, bone cancer, kidney cancer, ovarian cancer, bladder cancer, liver cancer, fallopian tube tumor, ovarian tumor, peritoneal tumor, melanoma, solid tumor, glioma, glioblastoma, hepatocellular carcinoma, mastoid renal tumor, head and neck tumor, leukemia, lymphoma, myeloma or non-small cell lung cancer.

The present invention further relates to a compound of formula I or a mesomer, racemate, enantiomer, diastereomer, or mixture thereof, a prodrug or a pharmaceutically acceptable salt, or a pharmaceutical composition comprising the same, for use as a BTK kinase inhibitor.

The present invention further relates to a compound of formula I or a mesomer, racemate, enantiomer, diastereomer, or mixture thereof, a prodrug or a pharmaceutically acceptable salt, or a pharmaceutical composition comprising the same, for use as a medicament for the prevention and/or treatment of disease associated with BTK activity. The disease associated with BTK activity may be selected from inflammation, autoimmune disease, and cancer, wherein the inflammation is for example, arthritis, particularly rheumatoid arthritis, psoriatic arthritis, inflammatory bowel disease, or Uveitis; the autoimmune disease is for example, multiple sclerosis, lupus, psoriasis, or sarcoidosis; the cancer is for example breast cancer, cervical cancer, colon cancer, lung cancer, stomach cancer, rectal cancer, pancreatic cancer, brain cancer, skin cancer, oral cancer, prostate cancer, bone cancer, kidney cancer, ovarian cancer, bladder cancer, liver cancer, fallopian tube tumor, ovarian tumor, peritoneal tumor, melanoma, solid tumor, glioma, glioblastoma, hepatocellular carcinoma, mastoid renal tumor, head and neck tumor, leukemia, lymphoma, myeloma or non-small cell lung cancer.

The present invention further relates to a method for inhibiting BTK kinase including administering a therapeutically effective amount of the compound of formula I or a mesomer, racemate, enantiomer, diastereomer, or mixture thereof, a prodrug or a pharmaceutically acceptable salt, or a pharmaceutical composition comprising the same to a patient in need of it.

The present invention further relates to a method for preventing and/or treating disease associated with BTK activity, including administering a therapeutically effective amount of the compound of formula I or a mesomer, racemate, enantiomer, diastereomer, or mixture thereof, a prodrug or a pharmaceutically acceptable salt, or a pharmaceutical composition comprising the same to a patient in need of it. The disease associated with BTK activity may be selected from inflammation, autoimmune disease, and cancer, wherein the inflammation is for example, arthritis, particularly rheumatoid arthritis, psoriatic arthritis, inflammatory bowel disease, or Uveitis; the autoimmune disease is for example, multiple sclerosis, lupus, psoriasis, or sarcoidosis; the cancer is for example, breast cancer, cervical cancer, colon cancer, lung cancer, stomach cancer, rectal cancer, pancreatic cancer, brain cancer, skin cancer, oral cancer, prostate cancer, bone cancer, kidney cancer, ovarian cancer, bladder cancer, liver cancer, fallopian tube tumor, ovarian tumor, peritoneal tumor, melanoma, solid tumor, glioma, glioblastoma, hepatocellular carcinoma, mastoid renal tumor, head and neck tumor, leukemia, lymphoma, myeloma or non-small cell lung cancer.

The compound of formula I of the present invention may be formed in a pharmaceutically acceptable acid addition salt with an acid according to the conventional methods in the art. The acid includes an inorganic acid or an organic acid, and particularly preferably hydrochloric acid, hydrobromic acid, sulfuric acid, phosphoric acid, methanesulfonic acid, ethanesulfonic acid, p-toluenesulfonic acid, benzenesulfonic acid, naphthalene disulfonic acid, acetic acid, propionic acid, lactic acid, trifluoroacetic acid, maleic acid, citric acid, fumaric acid, oxalic acid, tartaric acid, benzoic acid, and the like.

Furthermore, the present invention also relates the prodrugs of the compounds of formula I. The prodrugs of the present invention are derivatives of the compounds of formula I, which may have weak or even no activity per se, but may be converted to the corresponding biologically active form under physiological conditions (for example by metabolism, solvolysis or other ways) upon administration.

The pharmaceutical composition comprising active ingredients may be in a form suitable for oral administration, such as tablets, dragees, lozenges, aqueous or oily suspensions, dispersible powders or granules, emulsions, hard or soft capsules, or syrups or elixir. The oral composition can be prepared according to any method known in the art for preparing pharmaceutical compositions, and such composition may contain one or more ingredients selected from the group consisting of sweeteners, flavoring agents, coloring agents, and preservatives, to provide a pleasing and tasty pharmaceutical preparation. Tablets contain the active ingredient and non-toxic pharmaceutically acceptable excipients suitable for the preparation of a tablet. Such excipients may be inert excipients such as calcium carbonate, sodium carbonate, lactose, calcium phosphate or sodium phosphate; granulating agents and disintegrating agents such as microcrystalline cellulose, croscarmellose sodium, corn Starch or alginic acid; a binder such as starch, gelatin, polyvinylpyrrolidone or gum arabic; and a lubricant such as magnesium stearate, stearic acid or talc. These tablets may be uncoated or may be coated with common means which can mask the taste of the drug or delay the disintegration and absorption in the gastrointestinal tract, thereby providing a sustained release effect over a longer period of time. For example, water-soluble taste masking materials such as hydroxypropylmethylcellulose or hydroxypropylcellulose, or extended release materials such as ethylcellulose, acetate butyrate cellulose may be applied.

It is also possible to provide an oral preparation by a hard gelatin capsule in which the active ingredient is mixed with an inert solid diluent such as calcium carbonate, calcium phosphate or kaolin, or a soft gelatin capsule in which the active ingredient is mixed with a water-soluble carrier such as polyethylene glycol or an oil solvent such as peanut oil, liquid paraffin or olive oil.

The aqueous suspension contains the active substance and excipients suitable for the preparation of aqueous suspension. Such excipients are suspending agents such as sodium carboxymethylcellulose, methylcellulose, hydroxypropylmethylcellulose, sodium alginate, polyvinylpyrrolidone and acacia; dispersing or wetting agents which may be a naturally occurring phospholipid such as lecithin, or a condensation product of an alkylene oxide with a fatty acid such as polyoxyethylene stearate, or a condensation product of an ethylene oxide with a long chain fatty alcohol, such as heptadecylethyleneoxy cetanol, or a condensation product of an ethylene oxide with a part ester derived from a fatty acid and a hexitol, such as polyethylene oxide sorbitol monooleate, or a condensation product of an ethylene oxide with a partial ester derived from fatty acids and hexitols, such as polyethylene oxide sorbitan monooleate. The aqueous suspensions may also contain one or more preservatives such as ethylparaben or n-propylparaben, one or more coloring agents, one or more flavoring agents, and one or more sweetening agents, such as sucrose, saccharin or aspartame.

The oil suspension can be formulated by suspending the active ingredient in a vegetable oil such as peanut oil, olive oil, sesame oil or coconut oil, or a mineral oil such as liquid paraffin. The oil suspension may contain a thickening agent, such as beeswax, hard paraffin or cetyl alcohol. The above sweeteners and flavoring agents may be added to provide a palatable preparation. The composition can be kept by addition of an anti-oxidant such as butylated hydroxyanisole or alpha-tocopherol.

The active ingredient and dispersing or wetting agents, suspending agents or one or more preservatives can be provided by addition of water to the dispersible powders and granules suitable for the preparation of aqueous suspension. Suitable dispersing or wetting agents and suspending agents can be used to illustrate the above examples. Other excipients such as sweetening, flavoring, and coloring agents may also be added. The composition can be kept by addition of an anti-oxidant such as ascorbic acid.

The pharmaceutical composition of the invention may also be in the form of an oil-in-water emulsion. The oil phase may be a vegetable oil such as olive oil or peanut oil, or a mineral oil such as liquid paraffin or a mixture thereof. Suitable emulsifiers may be naturally occurring phospholipids, such as soy lecithin and esters or partial esters derived from fatty acids and hexitol anhydrides such as sorbitan monooleate, and condensation products of the partial esters and ethylene oxide, such as polyethylene oxide sorbitol monooleate. The emulsions may also contain sweeteners, flavoring agents, preservatives, and antioxidants. Syrups and elixirs may be formulated with sweetening agents such as glycerol, propylene glycol, sorbitol or sucrose. Such preparations may also contain a demulcent, a preservative, a colorant, and an antioxidant.

The pharmaceutical composition may be in the form of a sterile injectable aqueous solution. Among the acceptable vehicles or solvents that may be employed are water, Ringer's solution, and isotonic sodium chloride solution. The sterile injectable preparation may be a sterile injectable oil-in-water microemulsion in which the active ingredient is dissolved in the oil phase. For example, the active ingredient is dissolved in a mixture of soybean oil and lecithin. The oil solution is then added to a mixture of water and glycerin to form a microemulsion. The injection solution or microemulsion can be injected into the bloodstream of a patient by a local injection. Alternatively, the solution or microemulsion is preferably administered in a manner that maintains a constant circulating concentration of the present compound. To maintain this constant concentration, a continuous intravenous delivery device can be used. An example of such a device is the Deltec CADD-PLUS™ 5400 intravenous pump.

The pharmaceutical composition may be in the form of a sterile injectable aqueous or oil suspension for intramuscular and subcutaneous administration. The suspension may be formulated with those suitable dispersing or wetting agents and suspending agents indicated above according to known techniques. The sterile injectable preparation may also be a sterile injectable solution or suspension in a non-toxic parenterally acceptable diluent or solvent, such as a solution prepared in 1,3-butanediol. In addition, a sterile fixed oil may conveniently be employed as a solvent or suspension medium. For this purpose, any blended fixed oil including synthetic mono- or diglycerides can be used. In addition, fatty acids such as oleic acid can also used to prepare an injection.

The present compound may be administered in the form of a suppository for rectal administration. These pharmaceutical compositions can be prepared by mixing the drug with a suitable non-irritating excipient which is solid at ordinary temperatures but liquid in the rectum and thus dissolves in the rectum to release the drug. Such materials include cocoa butter, glycerin gelatin, hydrogenated vegetable oil, and a mixture of polyethylene glycols and fatty acid esters of polyethylene glycol with various molecular weights.

As is well known to those skilled in the art, the dosage of a drug depends on a variety of factors including, but not limited to, the activity of the particular compound used, the age, weight, condition, conduct, and diet of the patients, time of administration, way of administration, excretion rat, drug combination, and the like. Moreover, the optimal way of treatment, such as treatment mode, the daily dosage of the compound, or the type of the pharmaceutically acceptable salt, may be verified on the basis of the conventional therapeutic regimen.

The present invention may contain a composition comprising a compound with pyrroloheteroaromatic scaffold of formula I, or a pharmaceutically acceptable salt, hydrate or solvate thereof as an active ingredient, and a pharmaceutically acceptable carrier or excipient, which is formulated into a clinically acceptable preparation. The derivatives of the present invention can be used in combination with other active ingredients as long as they do not cause other adverse effects such as allergic reactions and the like. The present compound may be used as a single active ingredient or in combination with other agents for the treatment of disease associated with BTK activity. Combination therapy may be achieved by administering the individual therapeutic components simultaneously, separately or sequentially.

The present invention has been proved to have significant activity on regulating BTK kinase via a BTK activity assay, and thus the present compound can be used for the treatment and/or prevention of disease associated with BTK activity, such as inflammation, autoimmune disorder, cancer or other diseases, especially, for the treatment and/or prevention of rheumatoid arthritis, psoriasis, and/or the diseases involving cartilage degradation and bone and joint deterioration.

DETAILED DESCRIPTION OF THE INVENTION

Unless otherwise indicated, the terms used in the specification and claims have the following meanings.

The term "alkyl" refers to a saturated linear or branched aliphatic hydrocarbon containing one to twenty carbon atoms ($C_1$-$C_{20}$), preferably containing one to twelve carbon atoms, more preferably containing one to six carbon atoms. Examples of alkyl include, but are not limited to, methyl, ethyl, n-propyl, isopropyl, n-butyl, isobutyl, tert-butyl, sec-butyl, n-pentyl, 1,1-dimethylpropyl, 1,2-dimethylpropyl, 2,2-dimethylpropyl, 1-ethylpropyl, 2-methylbutyl, 3-methylbutyl, n-hexyl, 1-ethyl-2-methylpropyl, 1,1,2-trimethylpropyl, 1,1-dimethylbutyl, 1,2-dimethylbutyl, 2,2-dimethylbutyl, 1,3-dimethylbutyl, 2-ethylbutyl, 2-methylpentyl, 3-methylpentyl, 4-methylpentyl, 2,3-dimethylbutyl, n-heptyl, 2-methylhexyl, 3-methylhexyl, 4-methylhexyl, 5-methylhexyl, 2,3-dimethylpentyl, 2,4-dimethylpentyl, 2,2-dimethylpentyl, 3,3-dimethylpentyl, 2-ethylpentyl, 3-ethylpentyl, n-octyl, 2,3-dimethylhexyl, 2,4-dimethylhexyl, 2,5-dimethylhexyl, 2,2-dimethylhexyl, 3,3-dimethylhexyl, 4,4-dimethylhexyl, 2-ethylhexyl, 3-ethylhexyl, 4-ethylhexyl, 2-methyl-2-ethylpentyl, 2-methyl-3-ethylpentyl, n-decyl, 2-methyl-2-ethylhexyl, 2-methyl-3-ethylhexyl, 2,2-diethylpentyl, n-decyl, 3,3-diethylhexyl, 2,2-diethylhexyl, and various branched isomers thereof. More preferred alkyl is are lower alkyl groups with one to six carbon atoms ($C_1$-$C_6$) including, but not limited to, methyl, ethyl, n-propyl, isopropyl, n-butyl, isobutyl, tert-butyl, sec-butyl, n-pentyl, 1,1-dimethylpropyl, 1,2-dimethylpropyl, 2,2-dimethylpropyl, 1-ethylpropyl, 2-methylbutyl, 3-methylbutyl, n-hexyl, 1-ethyl-2-methylpropyl, 1,1,2-trimethylpropyl, 1,1-dimethylbutyl, 1,2-dimethylbutyl, 2,2-dimethylbutyl, 1,3-dimethylbutyl, 2-ethylbutyl, 2-methylpentyl, 3-methylpentyl, 4-methylpentyl, 2,3-dimethylbutyl, and the like. The alkyl group may be substituted or unsubstituted, and when substituted, the substituent may be substituted at any available point. The substituent is preferably selected from one or more groups independently selected from the group consisting of alkyl, alkenyl, alkynyl, alkoxyl, alkylthio, alkylamino, halogen, thiol, hydroxy, nitro, cyano, cycloalkyl, heterocycloalkyl, aryl, heteroaryl, cycloalkoxyl, heterocycloalkoxyl, cycloalkylthio, heterocycloalkylthio, oxo, carboxyl and a carboxylate group.

The term "alkenyl" refers to alkyl as defined above consisting of at least two carbon atoms and at least one carbon-carbon double bond, such as vinyl, 1-propenyl, 2-propenyl, 1-, 2- or 3-butenyl, and the like. The alkenyl group may be substituted or unsubstituted, and when substituted, the substituent is preferably one or more groups independently selected from the group consisting of alkyl, alkenyl, alkynyl, alkoxyl, alkylthio, alkylamino, halogen, thiol, hydroxy, nitro, cyano, cycloalkyl, heterocycloalkyl, aryl, heteroaryl, cycloalkoxyl, heterocycloalkoxyl, cycloalkylthio, and heterocycle alkylthio group.

The term "alkynyl" refers to alkyl as defined above consisting of at least two carbon atoms and at least one carbon-carbon triple bond, such as ethynyl, propynyl, butynyl and the like. The alkynyl group may be substituted or unsubstituted, and when substituted, the substituent is preferably one or more groups independently selected from the group consisting of alkyl, alkenyl, alkynyl, alkoxyl, alkylthio, alkylamino, halogen, thiol, hydroxy, nitro, cyano, cycloalkyl, heterocycloalkyl, aryl, heteroaryl, cycloalkoxyl, heterocycloalkoxyl, cycloalkylthio, heterocyclealkylthio group.

The term "cycloalkyl" refers to a saturated or partially unsaturated monocyclic or polycyclic hydrocarbon groups. The cycloalkyl ring includes 3-20 carbon atoms, preferably 3-12 carbon atoms, more preferably 3-6 carbon atoms. Examples of monocycloalkyl groups include, but are not limited to, cyclopropyl, cyclobutyl, cyclopentyl, cyclopentenyl, cyclohexyl, cyclohexenyl, cyclohexadienyl, cycloheptyl, cycloheptantrienyl, cyclooctyl, and the like. Polycyclic cycloalkyl groups include spiro, fused, and bridged cycloalkyl groups.

The term "spirocyclic alkyl" refers to a polycyclic group that shares one carbon atom (referred to as spiro atom) between 5 to 20 membered single ring, which may contain one or more double bonds, but none of the rings have a fully conjugated π electronic system. It is preferably 6 to 14 membered, more preferably 7 to 10 membered. The spirocyclic alkyl group is classified into monospirocyclic alkyl, bispirocyclic alkyl and polyspirocyclic alkyl depending on the number of common spiro atoms among the rings, preferably monospirocyclic alkyl and bispirocyclic alkyl; more preferably, 4 membered/4 membered, 4 membered/5 membered, 4 membered/6 membered, 5 membered/5 membered or 5 membered/6-membered monospirocycloalkyl group. Examples of spirocyclic alkyl include, but are not limited to,

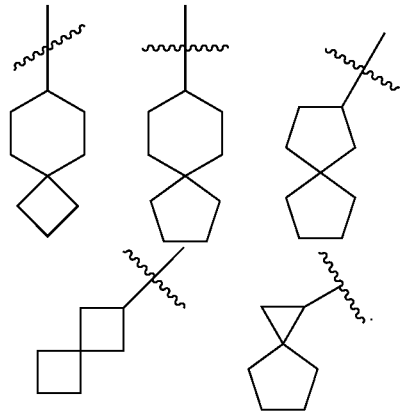

The term "fused cycloalkyl" refers to 5 to 20 membered all-carbon polycyclic group wherein each ring in the system shares an adjacent pair of carbon atoms with another rings in the system, wherein one or more of the rings may contain one or more double bonds, but none of the rings have a fully conjugated π-electron system. It is preferably 6 to 14 membered, more preferably 7 to 10 membered. Depending on the number of constituent rings, it may be classified into bicyclic, tricyclic, tetracyclic or polycyclic fused cycloalkyl group, preferably a bicyclic or tricyclic cycloalkyl, more preferably a 5-membered/5-membered or 5-membered/6-membered bicycloalkyl group. Examples of fused cycloalkyl include, but are not limited to,

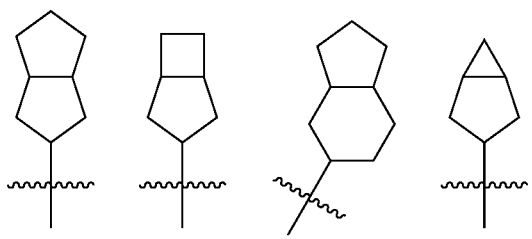

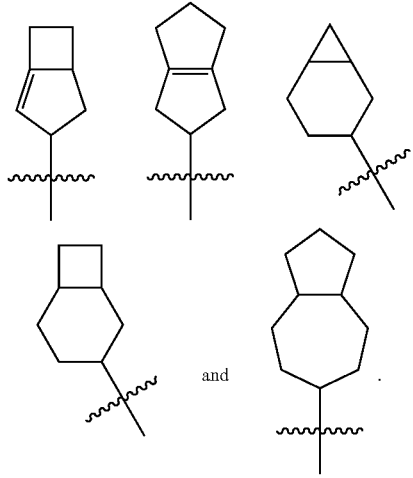

The term "bridged cycloalkyl" refers to 5 to 20 membered all-carbon polycyclic group, wherein any two rings share two carbon atoms which are not directly bonded, which may contain one or more double bonds, but none of the rings have a fully conjugated i-electron system. It is preferably 6 to 14 membered, more preferably 7 to 10 membered. Depending on the number of constituent rings, it may be classified into a bicyclic, tricyclic, tetracyclic or polycyclic bridged cycloalkyl group, preferably a bicyclic ring, a tricyclic ring or a tetracyclic ring, and more preferably a bicyclic ring or a tricyclic ring. Examples of bridged cycloalkyl include, but are not limited to,

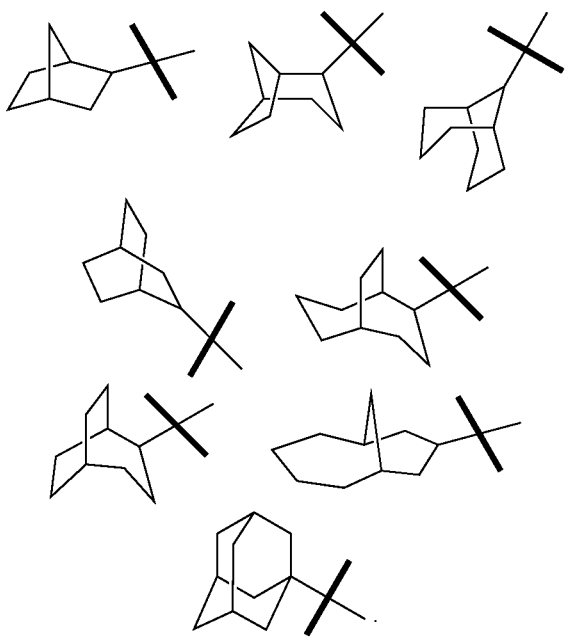

The cycloalkyl ring may be fused to an aryl, heteroaryl or heterocycloalkyl ring, wherein the ring to which the parent structure is attached is a cycloalkyl group. Non-limiting examples include indanyl, tetrahydronaphthyl, benzocycloheptyl and the like. The cycloalkyl group may be optionally substituted or unsubstituted, and when substituted, the substituent is preferably one or more groups independently selected from the group consisting of alkyl, alkenyl, alkynyl, alkoxyl, alkanethio, alkylamino, halogen, thiol, hydroxy, nitro, cyano, cycloalkyl, heterocycloalkyl, aryl, heteroaryl, cycloalkoxyl, heterocycloalkoxyl, cycloalkylthio, heterocycloalkylthio, oxo, carboxyl or carboxylate group.

The term "heterocyclyl" refers to a saturated or partially unsaturated monocyclic or polycyclic hydrocarbon groups containing from 3 to 20 ring atoms, wherein one or more ring atoms are selected from nitrogen, oxygen and $S(O)_m$ (m is an integer between 0 to 2), but excluding the ring moiety of —O—O—, —O—S— or —S—S—, and the remaining ring atoms are carbon. It preferably has 3 to 12 ring atoms with 1 to 4 heteroatoms, more preferably 3 to 8 ring atoms with 1 to 3 heteroatoms, most preferably 5 to 7 ring atoms with 1 to 2 or 1 to 3 heteroatoms. Non-limiting examples of monocyclic heterocyclic groups include pyrrolidinyl, imidazolidinyl, tetrahydrofuranyl, tetrahydrothiophenyl, dihydroimidazolyl, dihydrofuranyl, dihydropyrazolyl, dihydropyrrolyl, piperidinyl, piperazinyl, morpholinyl, thiomorpholinyl, homopiperazinyl, pyranyl and the like, preferably 1,2,5-oxadiazolyl, pyranyl or morpholinyl. Polycyclic heterocyclic groups include spiro, fused, and bridged heterocyclic groups.

The term "spiroheterocyclyl" refers to a polycyclic heterocyclic group that shares one atom (called a spiro atom) between 5 to 20 membered single ring, wherein one or more ring atoms are selected from nitrogen, oxygen or $S(O)_m$ (m is an integer of 0 to 2), and the remaining ring atoms are carbon. It may contain one or more double bonds, but none of the rings have a fully conjugated π-electron system. It is preferably 6 to 14 membered, more preferably 7 to 10 membered. The spiroheterocyclyl group may be classified into a monospiroheterocyclic group, a dispiroheterocyclic group or a polyspirocyclic group depending on the number of spiro atoms between the rings, preferably a monospiroheterocyclic group and a dispiroheterocyclic group. more preferably, 4 membered/4 membered, 4 membered/5 membered, 4 membered/6 membered, 5 membered/5 membered or 5 membered/6-membered monospiroheterocyclic group. Non-limiting examples of spiroheterocyclyl groups include:

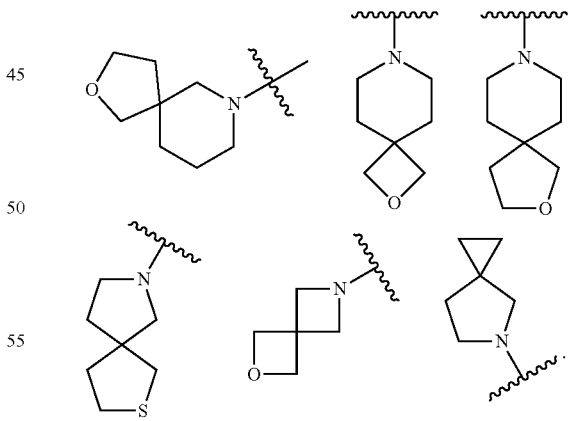

The term "fused heterocyclyl" refers to 5 to 20 membered polycyclic heterocyclic groups wherein each ring in the system shares an adjacent pair of atoms with another ring, and one or more rings may contain one or more double bond, but none of the rings have a fully conjugated xi-electron system, wherein one or more ring atoms are heteroatoms selected from nitrogen, oxygen and $S(O)_m$ (where m is an integer from 0 to 2), and the remaining ring atoms are carbon. It is preferably 6 to 14 membered, more preferably 7 to 10 membered. It may be classified into a bicyclic, tricyclic, tetracyclic or polycyclic fused heterocyclic group depending on the number of constituent rings, preferably a bicyclic or tricyclic ring, more preferably a 5-membered/5-membered or 5-membered/6-membered bicyclic fused heterocyclic group. Non-limiting examples of fused heterocyclic groups include:

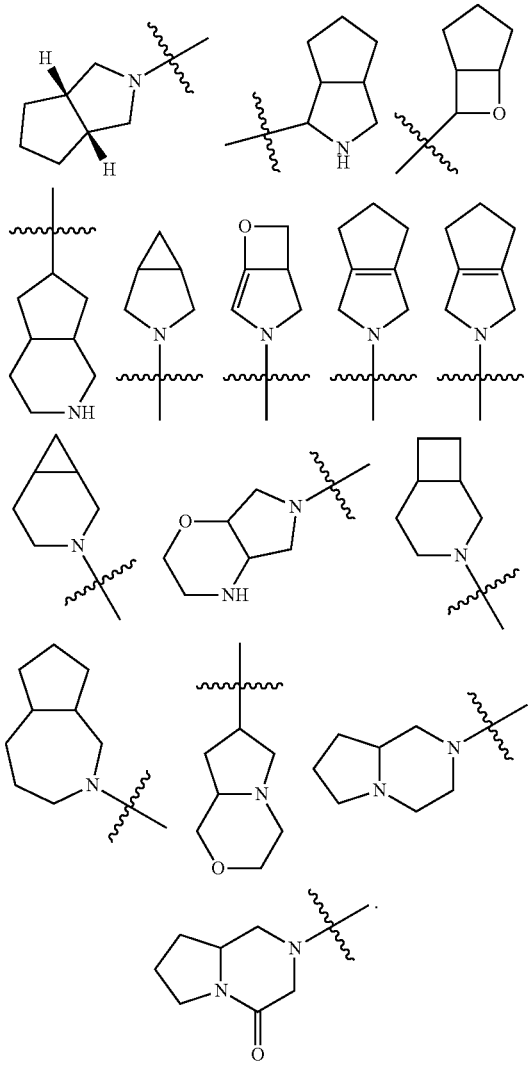

The term "bridge heterocyclyl" refers to a 5 to 14 membered polycyclic heterocyclic group in which any two rings share two atoms which are not directly bonded, which may contain one or more double bonds, but none of the rings have a total i-electron system, wherein one or more ring atoms are heteroatoms selected from nitrogen, oxygen and S(O)$_m$ (m is an integer from 0 to 2), and the remaining ring atoms are carbon. It is preferably 6 to 14 membered, more preferably 7 to 10 membered. Depending on the number of constituent rings, it may be classified into a bicyclic, tricyclic, tetracyclic or polycyclic bridged heterocyclic group, preferably a bicyclic ring, a tricyclic ring or a tetracyclic ring, and more preferably a bicyclic ring or a tricyclic ring. Non-limiting examples of bridge heterocyclic groups include:

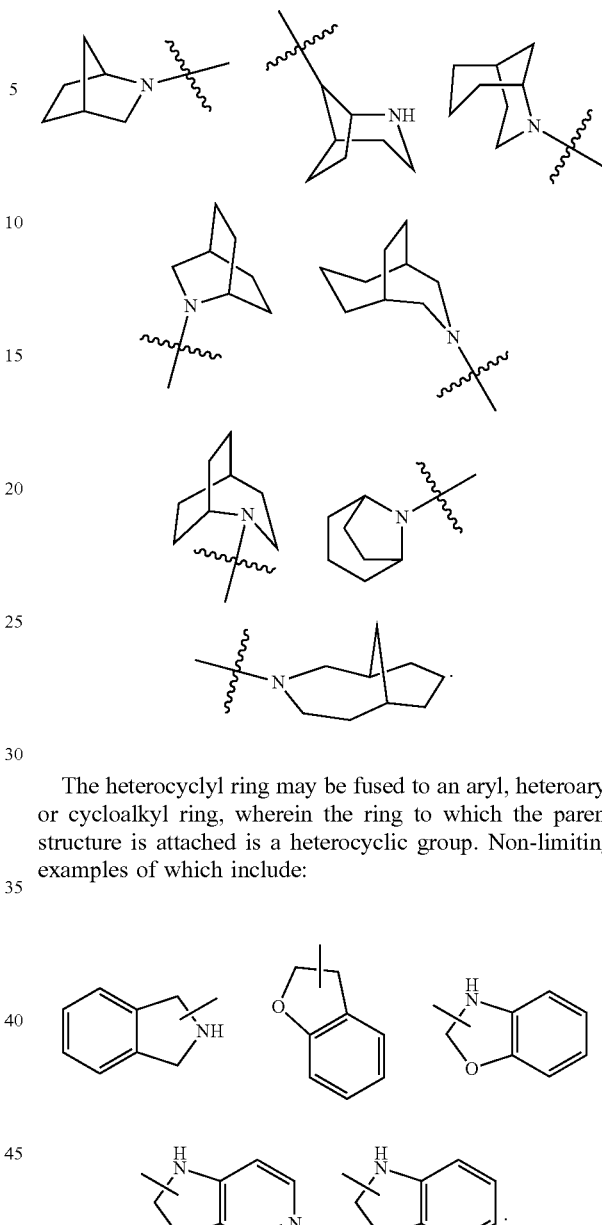

The heterocyclyl ring may be fused to an aryl, heteroaryl or cycloalkyl ring, wherein the ring to which the parent structure is attached is a heterocyclic group. Non-limiting examples of which include:

The heterocyclic group may be optionally substituted or unsubstituted, and when substituted, the substituent is preferably one or more groups independently selected from the group consisting of alkyl, alkenyl, alkynyl, alkoxyl, alkylthiol, alkylamino, halogen, thiol, hydroxy, nitro, cyano, cycloalkyl, heterocycloalkyl, aryl, heteroaryl, cycloalkoxyl, heterocycloalkoxyl, cycloalkylthio, heterocycloalkylthio, oxo, carboxyl or carboxylate group.

The term "aryl" refers to a 6 to 14 membered all-carbon monocyclic or fused polycyclic ring (the rings share an adjacent pair of atoms) having a conjugated i-electron system, preferably 6 to 10 membered, such as phenyl or naphthyl; more preferably phenyl. The aryl ring may be fused to a heteroaryl, heterocyclyl or cycloalkyl ring, wherein the ring to which the parent structure is attached is an aryl ring. Non-limiting examples include:

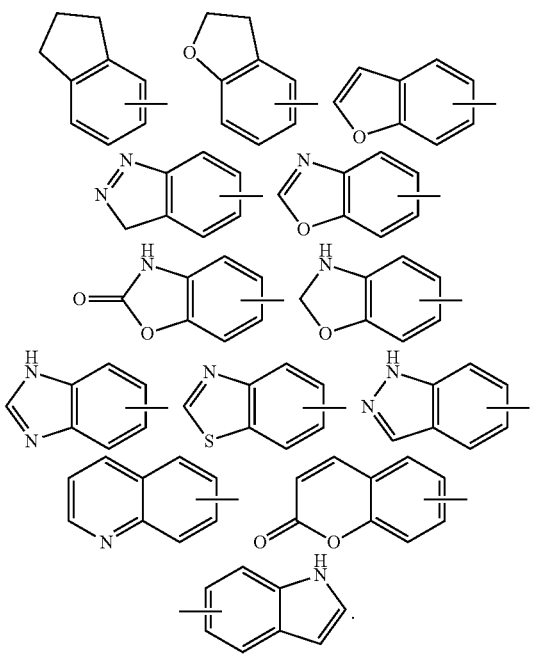

The aryl group may be substituted or unsubstituted, and when substituted, the substituent is preferably one or more groups independently selected from the group consisting of alkyl, alkenyl, alkynyl, alkoxyl, alkylthio, alkylamino, halogen, thiol, hydroxy, nitro, cyano, cycloalkyl, heterocycloalkyl, aryl, heteroaryl, cycloalkoxyl, heterocycloalkoxyl, cycloalkylthio, heterocycloalkylthio, carboxyl or carboxylate group.

The term "heteroaryl" refers to a heteroaromatic system containing 5 to 14 ring atoms and 1 to 4 heteroatoms selected from the group consisting of oxygen, sulfur and nitrogen. The heteroaryl group is preferably 5 to 10 membered with 1 to 3 heteroatoms; more preferably 5 or 6 membered with 1 to 2 heteroatoms. A heteroaryl is preferably imidazolyl, furyl, thienyl, thiazolyl, pyrazolyl, oxazolyl, pyrrolyl, tetrazolyl, pyridyl, pyrimidinyl, thiadiazole, pyrazinyl and the like; more preferably imidazolyl, thiazolyl, pyrazolyl or pyrimidinyl, thiazolyl; most preferably pyrazolyl or thiazolyl. The heteroaryl ring may be fused to an aryl, heterocyclic or cycloalkyl ring, wherein the ring to which the parent structure is attached is a heteroaryl ring. Non-limiting examples include:

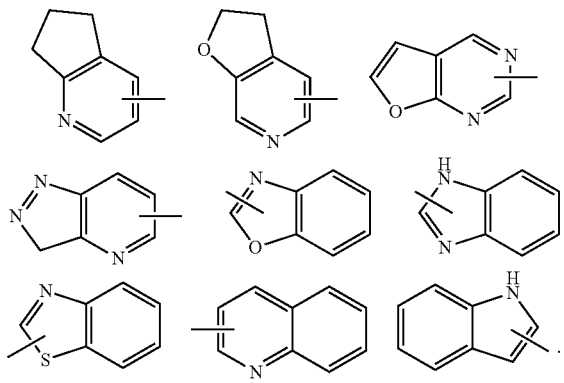

The heteroaryl group may be optionally substituted or unsubstituted, and when substituted, the substituent is preferably one or more groups independently selected from the group consisting of alkyl, alkenyl, alkynyl, alkoxyl, alkylthiol, alkylamino, halogen, thiol, hydroxy, nitro, cyano, cycloalkyl, heterocycloalkyl, aryl, heteroaryl, cycloalkoxyl, heterocycloalkoxyl, cycloalkylthio, heterocycloalkylthio, carboxyl or carboxylate group.

The term "alkoxyl" refers to —O-(alkyl) and —O-(unsubstituted cycloalkyl), wherein alkyl is as defined above. Non-limiting examples of alkoxyl groups include methoxy, ethoxy, propoxy, butoxy, cyclopropoxy, cyclobutoxy, cyclopentyloxy, or cyclohexyloxy. The alkoxyl group may be optionally substituted or unsubstituted, and when substituted, the substituent is preferably one or more groups independently selected from the group consisting of alkyl, alkenyl, alkynyl, alkoxyl, alkylthiol, alkylamino, halogen, thiol, hydroxy, nitro, cyano, cycloalkyl, heterocycloalkyl, aryl, heteroaryl, cycloalkoxyl, heterocycloalkoxy, cycloalkylthio, heterocycloalkylthio, carboxyl or carboxylate.

The term "haloalkyl" refers to an alkyl group substituted by one or more halogens, wherein alkyl is as defined above.

The term "haloalkoxy" refers to an alkoxy group substituted by one or more halogens, wherein alkoxy is as defined above.

The term "hydroxyalkyl" refers to an alkyl group substituted with a hydroxy group, wherein alkyl is as defined above.

The term "hydroxy" refers to —OH.

The term "halogen" refers to fluorine, chlorine, bromine or iodine.

The term "amino" refers to —NH$_2$.

The term "cyano" refers to —CN.

The term "nitro" refers to —NO$_2$.

The term "oxo" refers to =O.

The term "carboxy" refers to —C(O)OH.

The term "thiol" refers to —SH.

The term "ester group" refers to —C(O)O(alkyl) or —C(O)O(cycloalkyl), wherein alkyl and cycloalkyl are as defined above.

The term "acyl" refers to a compound containing a —C(O)R group, wherein R is alkyl, cycloalkyl, heterocyclyl, aryl, or heteroaryl.

The term "sulfonic acid group" refers to —S(O)$_2$OH.

The term "sulfonate group" refers to —S(O)$_2$O(alkyl) or —S(O)$_2$O(cycloalkyl), wherein alkyl and cycloalkyl are as defined above.

"Optional" or "optionally" means that the subsequently described event or environment may, but need not, occur, including where the event or environment occurs or does not occur. For example, "heterocyclic group optionally substituted with an alkyl group" means that an alkyl group may be, but not necessarily present, and the description includes the case where the heterocyclic group is substituted with an alkyl group and the case where the heterocyclic group is not substituted with an alkyl group.

"Substituted" refers to one or more hydrogen atoms in the group, preferably up to 5, more preferably 1 to 3 hydrogen atoms is replaced by a corresponding number of substituents. It goes without saying that the substituents are only in their possible chemical positions. Those skilled in the art will be able to determine (by experiment or theory) substitutions that may or may not be possible without undue effort. For example, an amino group or a hydroxyl group having a free hydrogen may be unstable when combined with a carbon atom having an unsaturated (e.g., olefinic) bond.

"Pharmaceutical composition" means a mixture comprising one or more of the compounds described herein, or a physiologically/pharmaceutically acceptable salt or a prodrug thereof, and other chemical components, as well as other components such as physiological/pharmaceutically acceptable carriers and excipients. The purpose of the pharmaceutical composition is to promote the administration to the organism, which facilitates the absorption of the active ingredient and thereby exerts biological activity.

"Pharmaceutically acceptable salt" refers to a salt of the present compound which is safe and effective for use in a mammal and which possesses the desired biological activity.

Methods for Synthesizing the Compound of the Present Invention

In order to achieve the object of the present invention, the present invention applies the following schemes.

The preparation method of the compound of formula I or salts thereof is as follows.

1) When W is N, the compound of formula I can be obtained via Suzuki reaction, coupling and deprotection reaction with compound Ia as raw material, according to the method shown in scheme 1.

Synthesis of Scheme 1:

Compound Ia is reacted with the corresponding boronic acid or boronic acid pinacol esters in the presence of catalyst under high-temperature and basic conditions to obtain compound Ib, wherein the basic reagent is preferably potassium carbonate or sodium carbonate, and the catalyst is preferably Pd(dppf)Cl$_2$ or Pd(PPh$_3$)$_4$, and the temperature is preferably 80-100° C.; then, the compound Ib is reacted with H—X—Y—Z under high-temperature and basic conditions to obtain compound Ic, wherein the basic reagent is preferably potassium carbonate, and the temperature is preferably 80-120° C.; finally the compound Ic is treated with acid, followed by aqueous ammonia to obtain a compound of formula I, wherein the acid is preferably trifluoroacetic acid.

2) When W is CR$^1$, the compound of formula I can be prepared via iodination reaction, Sonogashina coupling reaction, cyclization reaction, SEM protection, coupling and deprotection reaction with compound Id as raw material according to the method shown in scheme 2.

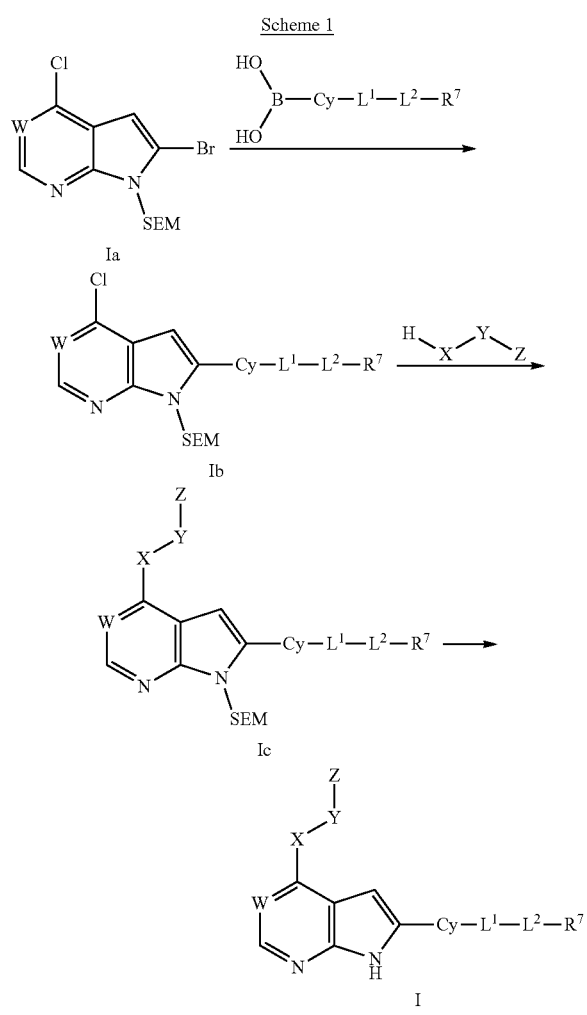

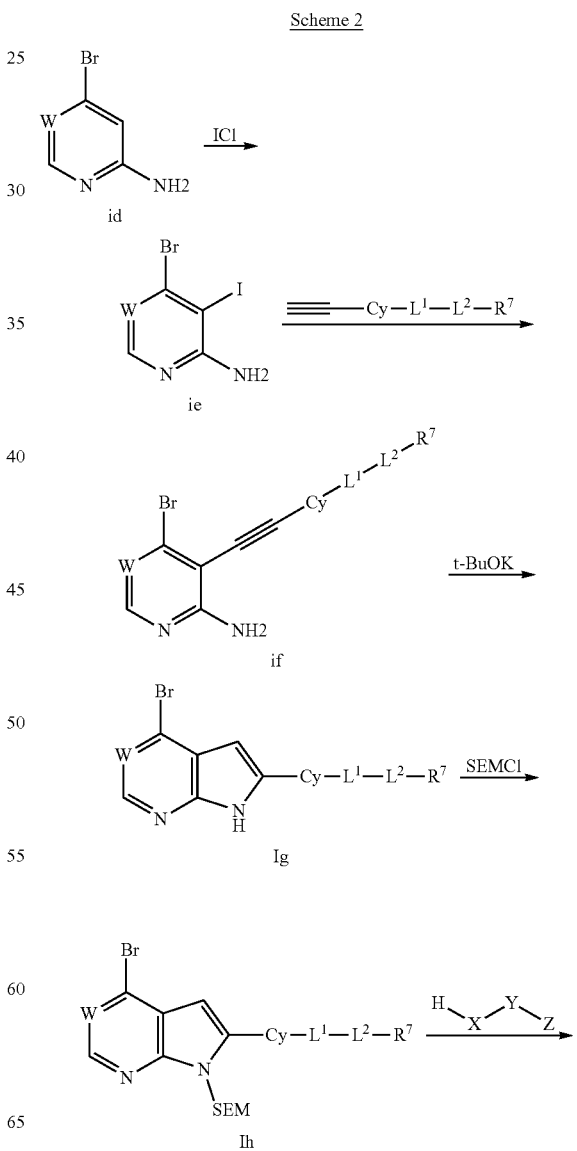

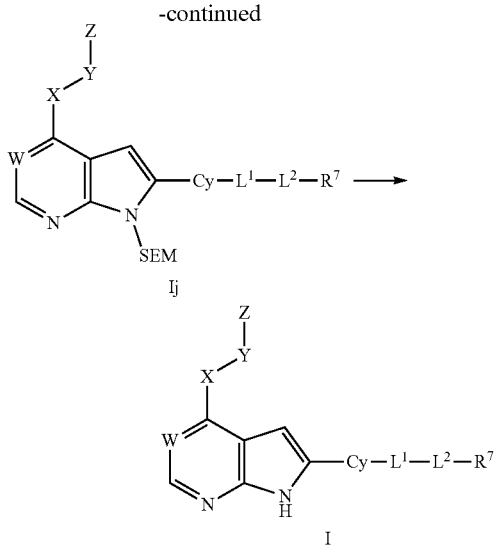

Synthesis of Scheme 2:

Compound Id is reacted with ICl under high-temperature conditions to obtain the iodo product Ie, wherein the temperature is preferably 40° C.; then, compound Ie is subjected to Sonogashina coupling reaction with the corresponding alkyne compound in the presense of a basic reagent and a catalyst to obtain compound If, wherein the basic reagent is preferably triethylamine, and the catalyst is preferably Pd(Ph$_3$P)$_2$Cl$_2$ and CuI; then, compound If is subjected to a cyclization reaction at high temperature and under basic conditions to obtain compound Ig, wherein the basic reagent is preferably potassium t-butoxide, and the temperature is preferably 70° C.; then, compound Ig is reacted with SEMCl under basic conditions to obtain compound Ih, wherein the basic reagent is preferably NaH; then, compound Ih is reacted with H—X—Y—Z under high temperature and basic conditions to obtain compound Ij, wherein the basic reagent is preferably potassium carbonate, and the temperature is preferably 80-120° C.; finally, compound Ij is treated with acid, followed by aqueous ammonia to obtain compound of formula I, wherein the acid is preferably trifluoroacetic acid.

EXAMPLES

The invention is further illustrated with reference to the following examples. It should be understood that these examples are not intend to to limit the scope of the invention.

The structure of the compound are determined by nuclear magnetic resonance (NMR) or/and mass spectrometry (MS). The NMR shift is given in units of 10-6 (ppm). The NMR is determined by using a Brukerdps300 type nuclear magnetic instrument. The solvent is deuterated dimethyl sulfoxide (DMSO-d$_6$), deuterated chloroform (CDCl$_3$), deuterated methanol (CD$_3$OD), and the internal standard is tetramethylsilane (TMS).

MS is determined using a 1100 Series LC/MSD Trap (ESI) mass spectrometer (manufacturer: Agilent, Inc.).

Preparative HPLC is carried out using lc3000 high performance liquid chromatography and lc6000 high performance liquid chromatography (manufacturer: Innovation Tongheng).

HPLC is carried out using a Shimadzu LC-20AD high pressure liquid chromatograph (Agilent TC-C18 250×4.6 mm 5 μm column) and a Shimadzu LC-2010 AHT high pressure liquid chromatograph (Phenomenex C18 250×4.6 mm 5 um column).

The average kinase inhibition rate and IC$_{50}$ value are determined using a multifunctional Cytation 3 plate reader (Bioteck, USA).

The thin layer chromatography (TLC) applies Qingdao Ocean Chemical GF254 silica gel plate, and the specification is 0.15 mm to 0.2 mm for analysis and 0.4 mm to 0.5 mm for separation and purification.

Column chromatography generally applies Qingdao Ocean Silicone 100-200 mesh and 200-300 mesh silica gel as carrier.

The known starting materials of the present invention may be synthesized by or according to methods known in the art, or may be purchased from WHall, Beijing Coupling, Sigma, Belling, Yi Shiming, Shanghai Shuya, Enoch, Energy Chemical and other companies.

Unless otherwise specified in the examples, the reactions all can be carried out under argon atmosphere or nitrogen atmosphere.

Argon atmosphere or nitrogen atmosphere means that the reaction flask is connected to an argon or nitrogen balloon having a volume of about 1 L.

The microwave reaction applies a CEM Discover SP type microwave reactor.

Unless otherwise specified in the examples, the solution means an aqueous solution.

Unless otherwise specified in the examples, the room temperature is 20° C. to 30° C.

The progress of the reaction in the examples is monitored by thin layer chromatography (TLC). The developing system includes: A: dichloromethane and methanol system, B: n-hexane and ethyl acetate system, C: petroleum ether and ethyl acetate system, D: acetone. The volume ratio of the solvent is adjusted depending on the polarity of the compound.

The eluent system of column chromatography and the developing system of TLC for the purification of the compound include: A: dichloromethane and methanol system, B: n-hexane and ethyl acetate system, C: petroleum ether and ethyl acetate system. The volume ratio of the solvent is adjusted depending on the polarity of the compound, and a small amount of an alkaline or acidic reagent such as triethylamine or acetic acid may be added for adjustment.

Example 1: Preparation of N-(3-((5-chloro-2-(4-(4-methylpiperazin-1yl)phenyl)-H-pyrrolo[2,3-b]pyridin-4-yl)oxy)phenyl) acrylamide

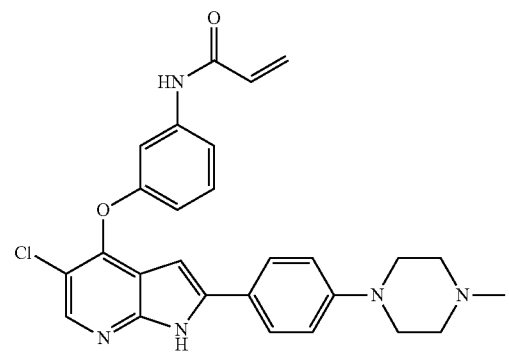

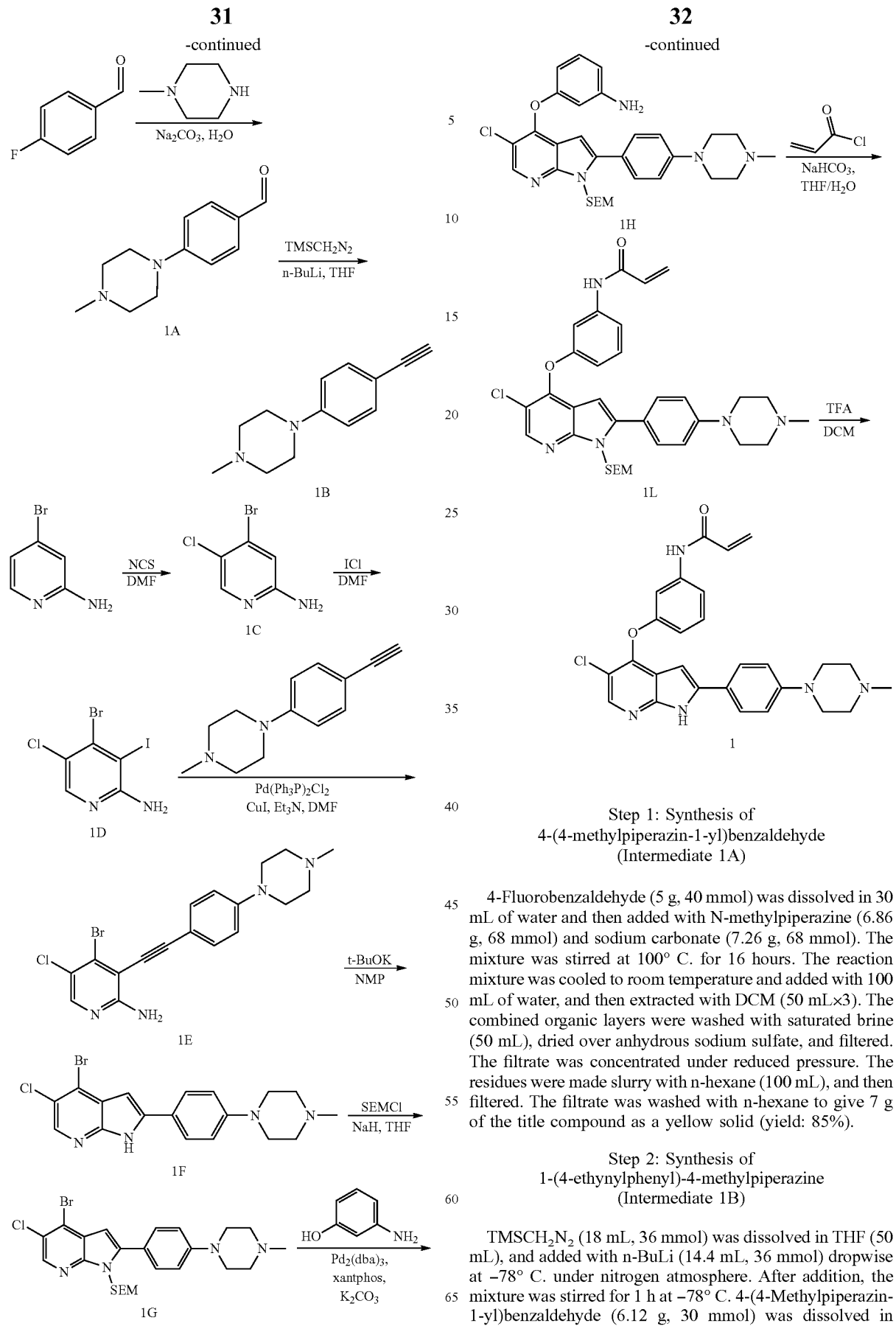

Step 1: Synthesis of
4-(4-methylpiperazin-1-yl)benzaldehyde
(Intermediate 1A)

4-Fluorobenzaldehyde (5 g, 40 mmol) was dissolved in 30 mL of water and then added with N-methylpiperazine (6.86 g, 68 mmol) and sodium carbonate (7.26 g, 68 mmol). The mixture was stirred at 100° C. for 16 hours. The reaction mixture was cooled to room temperature and added with 100 mL of water, and then extracted with DCM (50 mL×3). The combined organic layers were washed with saturated brine (50 mL), dried over anhydrous sodium sulfate, and filtered. The filtrate was concentrated under reduced pressure. The residues were made slurry with n-hexane (100 mL), and then filtered. The filtrate was washed with n-hexane to give 7 g of the title compound as a yellow solid (yield: 85%).

Step 2: Synthesis of
1-(4-ethynylphenyl)-4-methylpiperazine
(Intermediate 1B)

TMSCH$_2$N$_2$ (18 mL, 36 mmol) was dissolved in THF (50 mL), and added with n-BuLi (14.4 mL, 36 mmol) dropwise at −78° C. under nitrogen atmosphere. After addition, the mixture was stirred for 1 h at −78° C. 4-(4-Methylpiperazin-1-yl)benzaldehyde (6.12 g, 30 mmol) was dissolved in anhydrous THF (20 mL), and then added to the reaction mixture dropwise. Stirring was continued for another 1 h after addition. The reaction mixture was warmed to room temperature and stirred for another 1 h. The reaction mixture was quenched with a saturated aqueous solution of ammonium chloride (50 mL), and extracted with EtOAc (100 mL×2). The combined organic layers were washed with saturated brine (100 mL×2), dried over anhydrous sodium sulfate, and filtered. The filtrate was concentrated under reduced pressure. The residues were purified by column chromatography (eluent: DCM:MeOH, 50:1 to 10:1) to give 5 g of the title compound as a yellow solid (yield: 83%).

Step 3: Synthesis of 4-bromo-5-chloropyridin-2-amine (Intermediate 1C)

4-Bromopyridin-2-amine (17.3 g, 100 mmol) was dissolved in DMF (200 mL) and cooled at −20° C. NCS (14.7 g, 110 mmol) was added in portions at −20° C. The reaction mixture was stirred at rt. for 24 h, and then diluted with WATER (200 mL), extracted with EtOAc (100 mL×3). The combined organic layers were washed with saturated brine (100 mL×2), dried over anhydrous $Na_2SO_4$, and filtered. The filtrate was concentrated. The residues were purified by column chromatography (eluent: PE:EtOAc, 5:1 to 1:1) to give 15 g of the title compound as a yellow solid (yield: 72%).

Step 4: Synthesis of 4-bromo-5-chloro-3-iodopyridin-2-amine (Intermediate 1D)

4-Bromo-5-chloropyridin-2-amine (15 g, 72 mmol) was dissolved in DMF (200 mL) and heated to 40° C. Then ICl (12.2 g, 75 mmol) was added and stirred for 4 hours at 40° C. ICl (13 g, 80 mmol) was supplemented and then stirred for another 4 hours, and then a third ICl (13 g, 80 mmol) was added and stirred overnight at 40° C. After completion of the reaction, the reaction mixture was cooled to rt., diluted with water (200 mL), and extracted with DCM (200 mL×3). The combined organic layers were washed with an aqueous solution of sodium thiosulfate (100 mL×3) and saturated brine (100 mL×2), dried over anhydrous $Na_2SO_4$, and then filtered. The filtrate was concentrated. The residues were purified by column chromatography (eluent: PE:EtOAc, 5:1 to 1:1) to give 12 g of the title compound as claybank solid (yield: 50%).

Step 5: Synthesis of 4-bromo-5-chloro-3-((4-(4-methylpiperazin-1-yl)phenyl)ethynyl)pyridin-2-amine (Intermediate 1E)

4-Bromo-5-chloro-3-iodopyridin-2-amine (5 g, 15 mmol) was dissolved in DMF (50 mL) and added with 1-(4-ethynylphenyl)-4-methylpiperazine (3 g, 15 mmol), $Pd(Ph_3P)_2Cl_2$ (1.05 g, 1.5 mmol), CuI (570 mg, 3 mmol) and TEA (50 mL). The solution was degassed by $N_2$ for three times. The reaction mixture was stirred at rt. for 24 h under nitrogen atmosphere. After completion of the reaction, the reaction mixture was diluted with water (200 mL), and extracted with DCM (100 mL×3). The combined organic layers were washed with saturated brine (100 mL×2), dried over anhydrous Na2SO4, and filtered. The filtrate was concentrated under reduced pressure. The residues were purified by column chromatography (eluent: DCM:MeOH, 50:1 to 10:1) to give 3 g of the title compound as claybank solid (yield: 50%).

Step 6: Synthesis of 4-bromo-5-chloro-2-(4-(4-methylpiperazin-1-yl)phenyl)-1H-pyrrolo[2,3-b]pyridine (Intermediate 1F)

4-Bromo-5-chloro-3-((4-(4-methylpiperazin-1-yl)phenyl)ethynyl)pyridin-2-amine (3 g, 7.4 mmol) was dissolved in NMP (50 mL) and added with t-BuOK (1.0 g, 8.9 mmol) in portions. The mixture was stirred at 70° C. for 5 h. After completion of the reaction, the reaction mixture was quenched with a saturated aqueous solution of ammonium chloride (20 mL), and extracted with EtOAc (100 mL×3). The combined organic layers were washed with brine, dried over anhydrous $Na_2SO_4$, and filtered. The filtrate was concentrated under reduced pressure. The residues were purified by column chromatography (eluent: DCM:MeOH, 50:1 to 10:1) to give 1.5 g of the title compound as claybank solid (50% yield).

Step 7: Synthesis of 4-bromo-5-chloro-2-(4-(4-methylpiperazin-1-yl)phenyl)-1-((2-(trimethylsilyl)ethoxy)methyl)-1H-pyrrolo[2,3-b]pyridine (intermediate 1G)

4-Bromo-5-chloro-2-(4-(4-methylpiperazin-1-yl)phenyl)-1H-pyrrolo[2,3-b]pyridine (1.5 g, 3.7 mmol) was dissolved in anhydrous THF (50 mL) and added with NaH (0.22 g, 5.5 mmol) at 0° C. The reaction solution was stirred at 0° C. for 1 h, and then added with SEMCl (0.74 g, 4.4 mmol). The mixture was stirred at rt. for 2 h and then quenched with a saturated aqueous solution of ammonium chloride (20 mL), and extracted with EtOAc (50 mL×3). The combined organic layers were washed with saturated brine, dried over anhydrous $Na_2SO_4$, and filtered. The filtrate was concentrated under reduced pressure. The residues were purified by column chromatography (eluent: PE:EtOAc, 5:1 to 1:1) to give 1.2 g of the title compound as yellow oil (yield: 60%).

Step 8: Synthesis of 3-((5-chloro-2-(4-(4-methylpiperazin-1-yl)phenyl)-1-((2-(trimethylsilyl)ethoxy)methyl)-1H-pyrrolo[2,3-b]pyridin-4-yl)oxy)phenylamine (Intermediate 1H)

4-Bromo-5-chloro-2-(4-(4-methylpiperazin-1-yl)phenyl)-1-((2-(trimethylsilyl)ethoxy)methyl)-1H-pyrrolo[2,3-b]pyridine (0.8 g, 1.5 mmol) was dissolved in toluene (100 mL) and added with 3-aminophenol (0.2 g, 1.8 mmol), $Pd_2(dba)_3$ (0.137 g, 0.15 mmol), Xantphos (0.173 g, 0.3 mmol), K2CO3 (0.41 g, 3 mmol). The solution was degassed by N2 for three times. The reaction mixture was stirred under reflux for 3 h under nitrogen atmosphere. After completion of the reaction, the reaction mixture was concentrated under reduced pressure. The residues were purified by column chromatography (eluent: DCM:MeOH, 50:1 to 10:1) to give 0.6 g of the title compound as yellow solid (yield: 72%).

Step 9: Synthesis of N-(3-((5-chloro-2-(4-(4-methylpiperazin-1-yl)phenyl)-1-((2-(trimethylsilyl))ethoxy)methyl)-1H-pyrrolo[2,3-b]pyridin-4-yl)oxy)phenyl)acrylamide (Intermediate 1L)

3-((5-Chloro-2-(4-(4-methylpiperazin-1-yl)phenyl)-1-((2-(trimethylsilyl)ethoxy)methyl)-1H-pyrrolo[2,3-b]pyridin-4-yl)oxy)phenylamine (0.6 g, 1 mmol) was dissolved in THF/H₂O (30 mL/50 mL) at 0° C. and added with NaHCO₃ (180 mg, 2 mmol) and acryloyl chloride (100 mg, 1 mmol). The reaction mixture was stirred at 0° C. for 1 h. After completion of the reaction, the reaction mixture was extracted with EtOAc (50 mL×3). The combined organic layers were washed with saturated brine, dried over anhydrous Na₂SO₄, and filtered. The filtrate was concentrated under reduced pressure. The residues were purified by column chromatography (eluent: DCM:MeOH, 50:1 to 10:1) to give 0.5 g of the title compound as yellow solid (yield: 77%).

Step 10: Synthesis of N-(3-((5-chloro-2-(4-(4-methylpiperazin-1yl)phenyl)-1H-pyrrolo[2,3-b]pyridin-4-yl)oxy)phenyl)acrylamide (compound 1)

N-(3-((5-chloro-2-(4-(4-methylpiperazin-1-yl)phenyl)-1-((2-(trimethylsilyl)ethoxy)methyl)-1H-pyrrolo[2,3-b]pyridin-4-yl)oxy)phenyl)acrylamide (0.5 g, 0.8 mmol) was dissolved in DCM (15 mL) and added with TFA (15 mL). The reaction mixture was stirred at rt. for 24 h. After completion of the reaction, the reaction mixture was concentrated. The residues were purified by preparative HPLC to give 30 mg of the title compound as pale yellow solid (yield: 7.9%).

MS: m/z=488.3[M+H]⁺.

¹H NMR (300 MHz, DMSO): δ 12.39 (s, 1H), 10.20 (s, 1H), 9.73 (s, 1H), 8.27 (s, 1H), 7.72-7.74 (m, 2H), 7.46 (m, 1H), 7.37 (m, 2H), 7.02 (m, 3H), 6.79 (m, 1H), 6.35 (m, 1H), 6.19 (m, 2H), 5.72 (m, 1H), 3.95 (m, 2H), 3.50 (m, 2H), 3.13 (m, 2H), 3.01 (m, 2H), 2.85 (s, 3H).

Example 2: Preparation of N-(3-((5-fluoro-2-(4-(4-methylpiperazin-1yl)phenyl)-1H-pyrrolo[2,3-b]pyridin-4-yl)oxy)phenyl) acrylamide

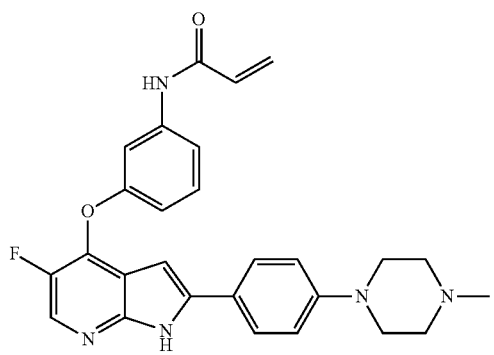 [SMILES: C=CC(=O)Nc1cccc(Oc2c(F)cnc3[nH]c(-c4ccc(N5CCN(C)CC5)cc4)cc23)c1]

The preparation method was the same as that of Example 1, except that 4-bromo-5-chloropyridin-2-amine (Intermediate IC) was replaced by 4-bromo-5-fluoropyridin-2-amine to obtain the title compound.

MS: m/z=471.3[M+H]⁺.

¹H NMR (300 MHz, DMSO): δ 12.51 (s, 1H), 10.33 (s, 1H), 8.29 (s, 1H), 7.69-7.78 (m, 2H), 7.40 (m, 1H), 7.33 (m, 1H), 6.94-7.03 (m, 3H), 6.80 (m, 1H), 6.41 (m, 1H), 6.24 (m, 2H), 5.70 (m, 1H), 3.72 (m, 4H), 3.14 (m, 2H), 2.99 (m, 2H), 2.87 (s, 3H).

Example 3: Preparation of N-(3-((5-cyano-2-(4-(4-methylpiperazin-1yl)phenyl)-1H-pyrrolo[2,3-b]pyridin-4-yl)oxy)phenyl)acrylamide

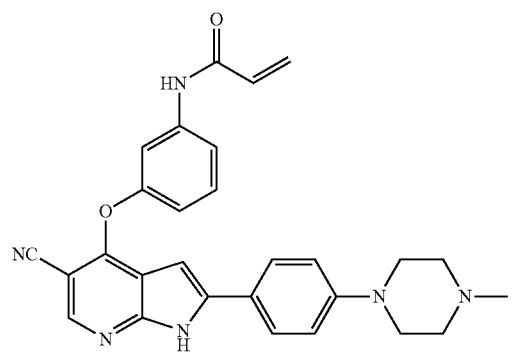 [SMILES: C=CC(=O)Nc1cccc(Oc2c(C#N)cnc3[nH]c(-c4ccc(N5CCN(C)CC5)cc4)cc23)c1]

The preparation method was the same as that of Example 1, except that 4-bromo-5-chloropyridin-2-amine (Intermediate IC) was replaced by 6-amino-4-bromo nicotinonitrile to obtain the title compound.

MS: m/z=479.4[M+H]⁺.

¹H NMR (300 MHz, DMSO): δ 12.55 (s, 1H), 10.33 (s, 1H), 8.41 (s, 1H), 7.80 (m, 2H), 7.50 (m, 1H), 7.39 (m, 2H), 7.10 (m, 3H), 6.85 (m, 1H), 6.39 (m, 1H), 6.21 (m, 2H), 5.75 (m, 1H), 3.78 (m, 4H), 3.13 (m, 4H), 2.85 (s, 3H).

Example 4: Preparation of N-(3-((5-methyl-2-(4-(4-methylpiperazin-1yl)phenyl)-1H-pyrrolo[2,3-b]pyridin-4-yl)oxy)phenyl)acrylamide

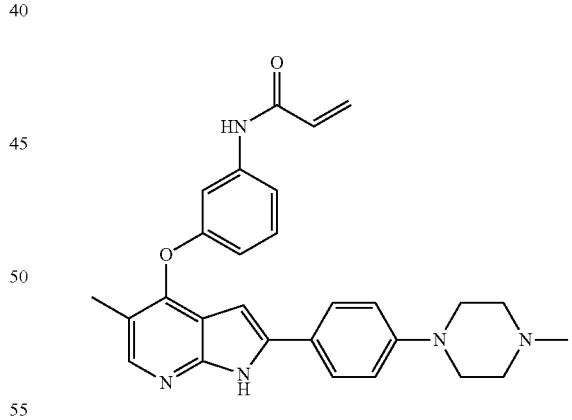

The preparation method was the same as that in Example 1 except that 4-bromo-5-chloropyridin-2-amine (Intermediate IC) was replaced by 4-amino-5-methylpyridine-2-amine to obtain the title compound.

MS: m/z=479.4[M+H]⁺.

¹H NMR (300 MHz, DMSO): δ 12.69 (s, 1H), 10.51 (s, 1H), 8.10 (s, 1H), 7.66-7.74 (m, 2H), 7.40 (m, 1H), 7.35 (m, 2H), 6.97 (m, 3H), 6.76 (m, 1H), 6.33 (m, 1H), 6.20 (m, 2H), 5.70 (m, 1H), 3.93-3.99 (m, 2H), 3.46-3.53 (m, 2H), 3.13 (m, 2H), 2.99 (m, 2H), 2.90 (s, 3H).

Example 5: Preparation of N-(3-((6-(4-(4-methylpiperazin-1-yl)phenyl)-7H-pyrrolo[2,3-d]pyrimidin-4-yl)amino)phenyl)acrylamide

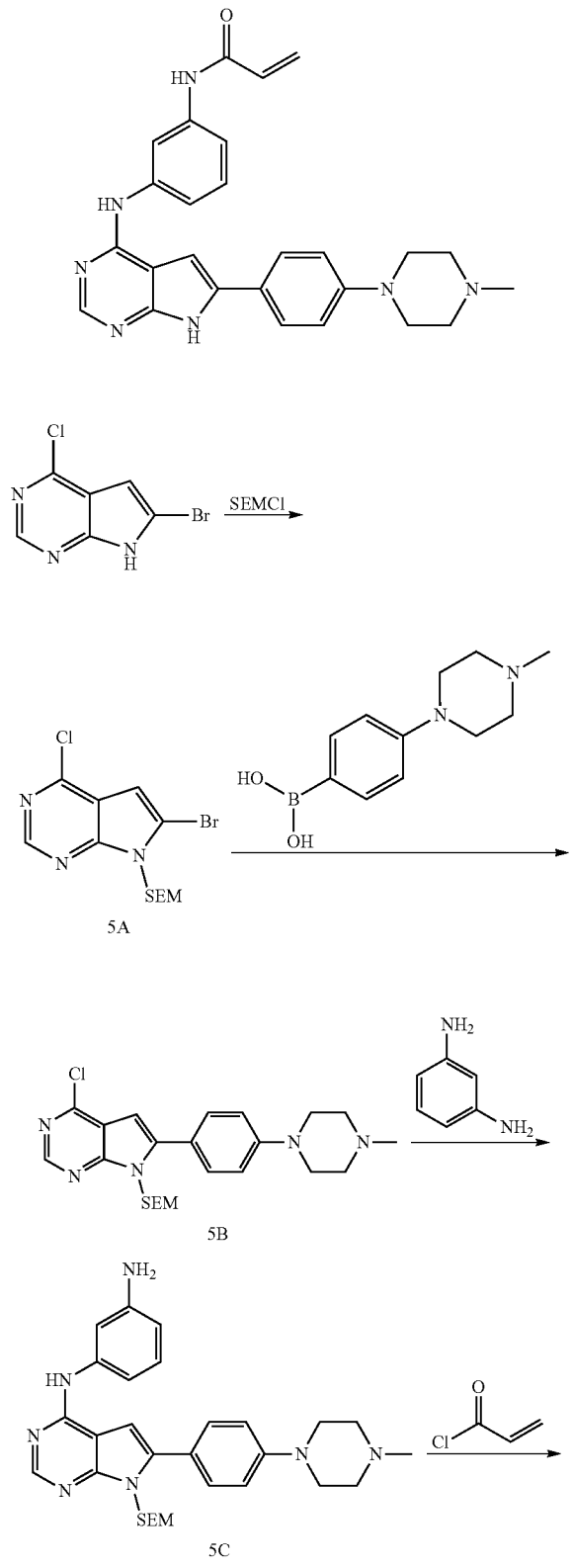

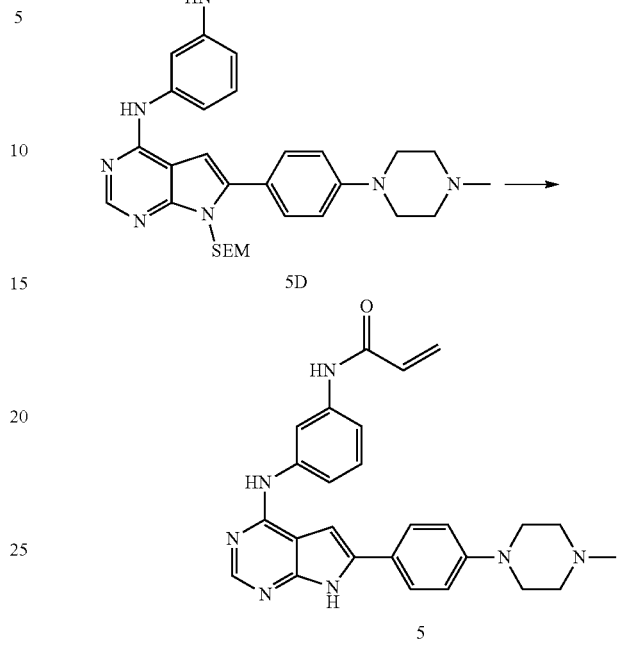

Step 1: Synthesis of 6-bromo-4-chloro-7-((2-(trimethylsilyl)ethoxy)methyl)-7H-pyrrolo[2,3-d]pyrimidine (Intermediate 5A)

6-Bromo-4-chloro-7H-pyrrolo[2,3-d]pyrimidine (purchased from WHmall) (1.1 g, 4.72 mmol) was dissolved in 40 mL of THF and cooled to 0-5° C. The solution was added with NaH (283 mg, 7.08 mmol) and stirred for 1 h. SEMCl (1.2 g, 7.08 mmol) was added dropwise and stirred for 3 h. The reaction mixture was quenched with a saturated aqueous solution of ammonium chloride (40 mL), and extracted with DCM (40 mL). The organic layer was washed with saturated brine (40 mL), dried over anhydrous $Na_2SO_4$, and filtered. The filtrate was concentrated under reduced pressure. The residues were purified by column chromatography (eluent: PE:EtOAc, 20:1 to 5:1) to give 900 mg of the title compound as white solid (yield: 52.6%).

Step 2: Synthesis of 4-chloro-6-(4-(4-methylpiperazin-1-yl)phenyl)-7-((2-(trimethylsilyl)ethoxy)methyl)-7H-pyrrole[2,3-d]pyrimidine (Intermediate 5B)

6-Bromo-4-chloro-7-((2-(trimethylsilyl)ethoxy)methyl)-7H-pyrrolo[2,3-d]pyrimidine (900 mg, 2.48 mmol) was added into a 100 mL of flask, and then added with (4-(4-methylpiperazin-1-yl)phenyl)boronic acid (491 mg, 2.23 mmol), dioxane (50 mL), sodium carbonate (632 mg, 5.96 mmol), water 5 mL and Pd (dppf) $Cl_2$ (100 mg, 0.14 mmol). The reaction mixture was stirred at 80° C. for 3 h under argon atmosphere. The reaction mixture was cooled to rt. and then concentrated under reduced pressure. The residues were purified by column chromatography (eluent: EtOAc) to give 600 mg of the title compound as brown oil (yield: 52.8%).

Step 3: Synthesis of N-(6-(4-(4-Methylpiperazin-1-yl)phenyl)-7-((2-(trimethylsilyl)ethoxy)methyl)-7H-pyrrolo[2,3-d]pyrimidin-4-yl)benzene-1,3-diamine (intermediate 5C)

4-Chloro-6-(4-(4-methylpiperazin-1-yl)phenyl)-7-((2-(trimethylsilyl)ethoxy)methyl)-7H-pyrrole[2,3-d]pyrimidine (600 mg, 1.31 mmol), m-phenylenediamine (284 mg, 2.62 mmol), TsOH (226 mg, 1.31 mmol), n-BuOH (25 mL) were added to the reaction flask under nitrogen atmosphere. The reaction mixture was stirred at 100° C. for 2 h. The reaction mixture was concentrated under reduced pressure and the residues were purified by column chromatography (eluent: DCM:MeOH, 20:1) to give 450 mg of the title compound (yield: 52.8%).

Step 4: Synthesis of N-(3-((6-(4-(4-methylpiperazin-1-yl)phenyl)-7-((2-(trimethylsilyl)ethoxy)methyl)-7H)pyrrolo[2,3-d]pyrimidinpiperidin-4-yl)amino)phenyl)acrylamide (Intermediate 5D)

N-(6-(4-(4-Methylpiperazin-1-yl)phenyl)-7-((2-(trimethylsilyl)ethoxy)methyl)-7H-pyrrolo[2,3-d]pyrimidin-4-yl)benzene-1,3-diamine (450 mg, 0.76 mmol) was dissolved in DCM (30 mL) and added with $Et_3N$ (156 mg, 1.52 mmol). The mixture was cooled to 0-5° C. and then added with a solution of 75 mg (0.83 mmol) of acryloyl chloride in DCM (10 mL) dropwise. The mixture was stirred for 1 h at 0-5° C. After completion of the reaction, the reaction mixture was quenched with 40 mL of water and the organic layer was washed with 50 mL of saturated brine, dried over anhydrous sodium sulfate, and filtered. The filtrate was concentrated under reduced pressure to give 520 mg of crude compound which was used directly in the next step without purification.

Step 5: Synthesis of N-(3-((6-(4-(4-methylpiperazin-1-yl)phenyl)-7H-pyrrolo[2,3-d]pyrimidin-4-yl)amino)phenyl) acrylamide (Compound 5)

N-(3-((6-(4-(4-methylpiperazin-1-yl)phenyl)-7-((2-(trimethylsilyl)ethoxy)methyl)-7H)pyrrolo[2,3-d]pyrimidinpiperidin-4-yl)amino)phenyl)acrylamide (520 mg 0.89 mmol) was added to a 50 mL reaction flask, and added with DCM (5 mL) and trifluoroacetic acid (5 mL). The reaction solution was stirred at room temperature overnight and concentrated under reduced pressure to dryness. The residues were added with methanol (20 mL) and aqueous ammonia (3 mL), and stirred at room temperature for 3 h. After completion of the reaction, the reaction mixture was added 10 mL of saturated brine and extracted with DCM (20 mL). The organic layer was concentrated under reduced pressure. The residues were purified by column chromatography (eluent: DCM:MeOH, 10:1) to give 120 mg of the title compound as pale yellow solid (yield: 29.7%, purity: 95.4%).

MS: m/z=454.6[M+H]$^+$.

$^1$H NMR (300 MHz, MeOD): δ 8.18 (s, 1H), 8.08 (d, 1H), 7.73 (d, 2H), 7.53 (m, 2H), 7.28 (m, 1H), 7.13 (d, 2H), 6.93 (s, 1H), 6.41 (m, 2H), 5.80 (m, 1H), 3.75 (m, 4H), 3.18 (m, 4H), 2.98 (m, 3H).

Example 6: Preparation of N-(3-((6-(4-(4-methylpiperazin-1-yl)phenyl)-7H-pyrrolo[2,3-d]pyrimidin-4-yl)oxy)phenyl) but-2-ynylamide

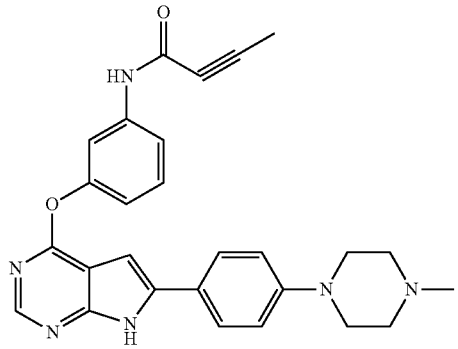

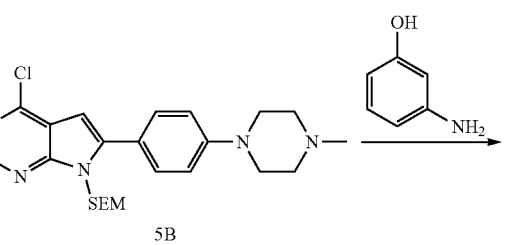

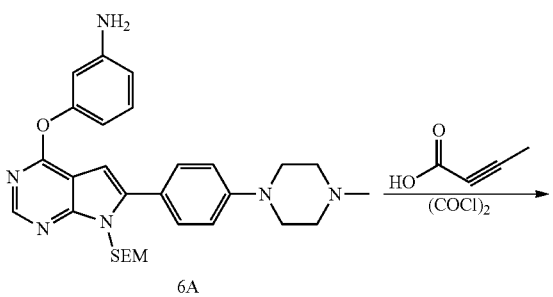

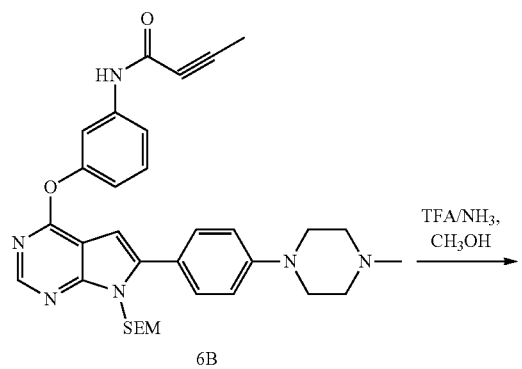

41

-continued

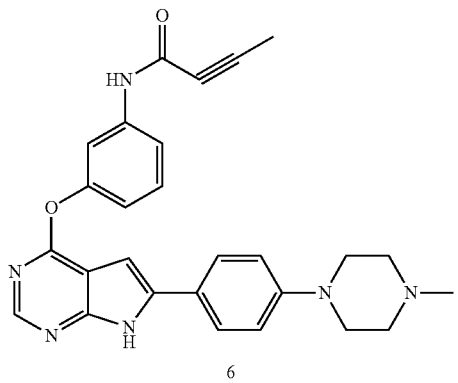

6

Step 1: Synthesis of 3-((6-(4-(4-methylpiperazin-1-yl)phenyl)-7-((2-(trimethylsilyl)ethoxy)methyl)-7H-pyrrolo[2,3-d]pyrimidin-4-yl)oxy)aniline (Intermediate 6A)

4-Chloro-6-(4-(4-methylpiperazin-1-yl)phenyl)-7-((2-(trimethylsilyl)ethoxy)methyl)-7H-pyrrole[2,3-d]pyrimidine (1.5 g, 3.28 mmol) was added into a 50 mL flask and then added with m-aminophenol (0.54 g, 4.9 mmol), potassium carbonate (0.90 g, 6.55 mmol), and DMF (15 mL). The reaction solution was warmed to 100° C. and stirred overnight. After completion of the reaction, the reaction mixture was concentrated under reduced pressure. The residues were purified by column chromatography (eluent: DCM:MeOH, 30:1) to give 1.20 g of the title compound as pale yellow oil (yield of 69.1%, purity of 96.4%).

Step 2: Synthesis of N-(3-((6-(4-(4-methylpiperazin-1-yl)phenyl)-7-((2-(trimethylsilyl)ethoxy)methyl)-7H)pyrrolo[2,3-d]pyrimidin-4-yl)oxy)phenyl)but-2-ynylamide (Intermediate 6B)

Preparation of but-2-ynoic acid chloride

2-Butynoic acid (2.0 g, 23.8 mmol) was added to a 50 mL of flask and added with THF (20 mL). The mixture was stirred under room temperature and added with oxalyl chloride (1.2 mL) dropwise. Then, three drops of DMF was added. The reaction mixture was stirred at rt. for 1 h. The reaction mixture was concentrated under reduced pressure to dryness.

3-((6-(4-(4-Methylpiperazin-1-yl)phenyl)-7-((2-(trimethylsilyl)ethoxy)methyl)-7H-pyrrolo[2,3-d]pyrimidin-4-yl)oxy)aniline (1.2 g, 2.26 mmol) was added to a 50 mL reaction flask and added with sodium bicarbonate (0.29 g, 3.40 mmol), THF (20 mL), and water (4 mL). The mixture was stirred under ice bath. The but-2-ynoic acid chloride prepared above was dissolved in 10 mL of THF and added to the flask dropwise. The reaction mixture was stirred at rt. for 1 h. After completion of the reaction, the reaction mixture was quenched with a saturated aqueous solution of ammonium chloride (50 mL), and extracted with DCM (50 mL). The organic layer was dried over anhydrous $Na_2SO_4$, and filtered. The filtrate was concentrated under reduced pressure. The residues were purified by column chromatography (eluent: DCM:MeOH, 50:1 to 10:1) to give 500 mg of the title compound as pale yellow solid (yield of 37.1%, purity of 97.4%).

Step 3: Synthesis of N-(3-((6-(4-(4-methylpiperazin-1-yl)phenyl)-7H-pyrrolo[2,3-d]pyrimidin-4-yl)oxy)phenyl) but-2-ynylamide (Compound 6)

N-(3-((6-(4-(4-methylpiperazin-1-yl)phenyl)-7-((2-(trimethylsilyl)ethoxy)methyl)-7H) pyrrolo[2,3-d]pyrimidin-4-yl)oxy)phenyl)but-2-ynylamide (500 mg, 0.8 mmol) was added to a 50 mL of flask and added with DCM (5 mL) and TFA (5 mL). The reaction mixture was stirred at rt. overnight. The reaction mixture was concentrated under reduced pressure. The residues were added with methanol (3 mL) and aqueous ammonia (3 mL) and stirred at rt. for 1 h. After the completion of the reaction, the mixture was filtered and the filter cake was washed with water (5 mL) and dried to give 180 mg the title compound as a pale yellow solid (yield: 46.0%, purity: 95.3%).

MS: m/z=467.9 [M+H]$^+$.

$^1$H NMR (300 MHz, DMSO): δ 12.53 (s, 1H), 10.77 (s, 1H), 8.26 (m, 1H), 7.80 (m, 2H), 7.56 (m, 1H), 7.42 (m, 2H), 7.01 (m, 3H), 6.83 (m, 1H), 3.33 (m, 4H), 3.24 (m, 4H), 2.26 (s, 3H), 2.05 (s, 3H).

Example 7: Preparation of N-(2-fluoro-5-((6-(4-(4-methylpiperazin-1-yl)phenyl)-7H-pyrrolo[2,3-d]pyrimidin-4-yl)oxy)phenyl)but-2-ynylamide

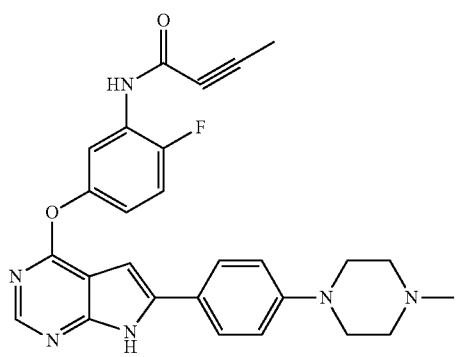 [SMILES: CC#CC(=O)Nc1cc(Oc2ncnc3[nH]c(-c4ccc(N5CCN(C)CC5)cc4)cc23)ccc1F]

The preparation method was the same as that of Example 6, except that 3-aminophenol was replaced by 3-amino-4-fluorophenol to obtain the title compound.

MS: m/z=485.3 [M+H]$^+$.

$^1$H NMR (300 MHz, DMSO): δ 12.48 (s, 1H), 10.69 (s, 1H), 8.28 (m, 1H), 7.83 (m, 2H), 7.53 (m, 3H), 7.08 (m, 3H), 6.85 (m, 1H), 3.38 (m, 4H), 3.25 (m, 4H), 2.26 (s, 3H), 2.05 (s, 3H).

Example 8: Preparation of 4-(dimethylamino)-N-(3-((6-(4-(4-methylpiperazin-1-yl)phenyl)-7H-pyrrolo[2,3-d]pyrimidine-4-yl)oxy)phenyl)but-2-enamide

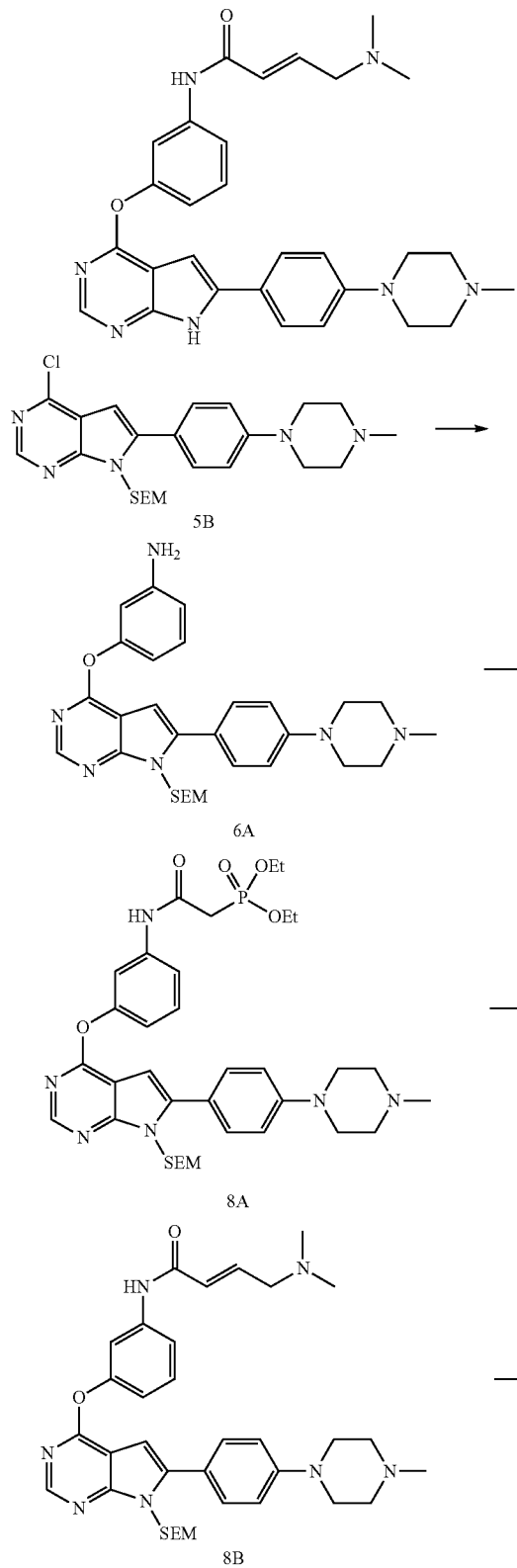

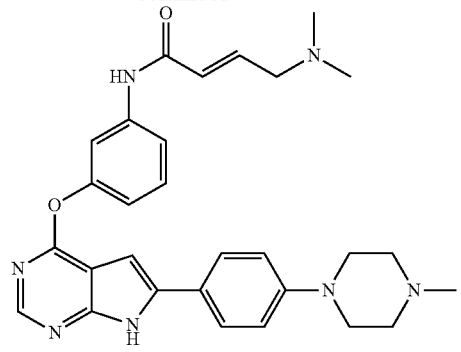 [SMILES: CN(C)C/C=C/C(=O)Nc1cc(Oc2ncnc3[nH]c(-c4ccc(N5CCN(C)CC5)cc4)cc23)ccc1F]

Step 1: Synthesis of 3-((6-(4-(4-methylpiperazin-1-yl)phenyl)-7-((2-(trimethylsilyl)ethoxy)methyl)-7H-pyrrolo[2,3-d]pyrimidin-4-yl)oxy)aniline (Intermediate 6A)

4-Chloro-6-(4-(4-methylpiperazin-1-yl)phenyl)-7-((2-(trimethylsilyl)ethoxy)methyl)-7H-pyrrolo[2,3-d]pyrimidine (3.00 g, 6.55 mmol) was added to a 50 mL of flask and added with m-aminophenol (1.08 g, 9.8 mmol), potassium carbonate (1.80 g, 13.10 mmol) and DMF (30 mL). The mixture was stirred at 100° C. overnight. After completion of the reaction, the reaction mixture was concentrated under reduced pressure to dryness. The residues were purified by column chromatography (eluent: DCM:MeOH, 30:1) to give 2.3 g of the title compound as pale yellow oil (yield of 66.2%, purity of 95.7%).

Step 2: Synthesis of Diethyl (2-((3-(6-(4-(4-methylpiperazin-1-yl)phenyl)-7-((2-(trimethylsilyl)ethoxy)methyl)-7H-pyrrolo[2,3-d]pyrimidin-4-yl)oxy)phenyl)amino)-2-oxoethyl)phosphonate (Intermediate 8A)

N,N'-carbonyldiimidazole (0.93 g, 5.86 mmol) and THF (20 mL) were added to a 50 mL of flask and stirred at room temperature for 10 min. Diethylphosphoric acid (1.50 g, 7.66 mmol) was added to THF (10 mL) and added to the flask dropwise. Then, 3-((6-(4-(4-methylpiperazin-1-yl)phenyl)-7-((2-(trimethylsilyl)ethoxy)methyl)-7H-pyrrolo[2,3-d]pyrimidin-4-yl)oxy)aniline was added in THF (10 mL) and added to the reaction flask dropwise. The mixture was stirred at rt. overnight. After completion of the reaction, the reaction mixture was added with EtOAc (50 mL) and washed with water (50 mL). The organic layer was washed with saturated brine (80 mL) two times, dried over anhydrous sodium sulfate, and filtered. The filtrate was concentrated under reduced pressure to give 1.50 g of the title compound as brown solid (yield of 80.2%, purity of 95.0%).

Step 3: Synthesis of 4-(dimethylamino)-N-(3-((6-(4-(4-methylpiperazin-1-yl)phenyl)-7-((2-(trimethylsilyl)ethoxy)methyl)-1H-pyrrolo[2,3-d]pyrimidin-4-yl)oxy)phenyl)but-2-enamide (Intermediate 8B)

Preparation of (Dimethylamino)Acetaldehyde Solution

Concentrated hydrochloric acid (5 mL) and water (2 mL) were added to a 50 mL of flask and then heated to 40° C.

N,N-dimethylaminoacetaldehyde diethyl acetal was added to the reaction flask and the mixture was stirred at 40° C. overnight.

Diethyl (2-((3-(6-(4-(4-methylpiperazin-1-yl)phenyl)-7-((2-(trimethylsilyl)ethoxy)methyl)-7H-pyrrolo[2,3-d]pyrimidin-4-yl)oxy)phenyl)amino)-2-oxoethyl)phosphonate (1.0 g, 1.4 mmol) and DMF (10 mL) were added to a 50 mL of flask and added with NaH (0.5 g, 20.83 mmol) under ice bath. After stirring for 30 min, (dimethylamino)acetaldehyde solution was added dropwise, followed by stirring under ice bath. for 1 h. After completion of the reaction, the reaction mixture was diluted with water (50 mL), and extracted with EtOAc (20 mL). The aqueous layer was alkalified to pH 9-10 with NaOH aqueous solution. The mixture was extracted with EtOAc (20 mL) and the combined organic layer was concentrated under reduced pressure to dryness. The residues were purified by column chromatography (eluent: DCM:MeOH, 10:1) to give 0.30 g of the title compound as yellow solid (yield of 33.1%, purity of 98.7%).

Step 4: Synthesis of 4-(dimethylamino)-N-(3-((6-(4-(4-methylpiperazin-1-yl)phenyl)-7H-pyrrolo[2,3-d]pyrimidin-4-yl)oxy)phenyl)but-2-enamide (Compound 8)

4-(dimethylamino)-N-(3-((6-(4-(4-methylpiperazin-1-yl)phenyl)-7-((2-(trimethylsilyl)ethoxy)methyl)-1H-pyrrolo[2,3-d]pyrimidin-4-yl)oxy)phenyl)but-2-enamide (300 mg, 0.47 mmol) was added to a 25 mL of flask and added with DCM (3 mL) and TFA (3 mL). The reaction mixture was stirred at rt. overnight. The reaction mixture was concentrated under reduced pressure. The residues were added with methanol (3 mL) and aqueous ammonia (3 mL), and stirred at room temperature for 1 h. After completion of the reaction, the reaction mixture was filtered and the filter cake was washed 5 mL of water and dried to give 110 mg of the title compound as pale yellow solid (yield of 46.0%, purity of 95.3%).

MS: m/z=512.3[M+H]$^+$.

$^1$H NMR (300 MHz, DMSO): δ 12.53 (s, 1H), 10.68 (s, 1H), 8.24 (m, 1H), 7.76 (m, 2H), 7.54 (m, 1H), 7.40 (m, 2H), 7.00 (m, 3H), 6.80 (m, 1H), 6.74 (m, 1H), 6.06 (m, 1H), 3.10 (m, 4H), 3.01 (m, 2H), 2.58 (m, 4H), 2.34 (m, 3H), 2.18 (s, 6H).

Example 9: Preparation of 4-(dimethylamino)-N-(2-fluoro-5-((6-(4-(4-methylpiperazin-1-yl)phenyl)-7H-pyrrolo[2,3-d]pyrimidin-4-yl)oxy)phenyl)but-2-enamide The preparation method was the same as that of Example 8, except that 3-aminophenol was replaced by 3-amino-4-fluorophenol to obtain the title compound.

MS: m/z=530.1[M+H]$^+$.

$^1$H NMR (300 MHz, DMSO): δ 12.48 (s, 1H), 10.56 (s, 1H), 8.28 (m, 1H), 7.80 (m, 2H), 7.43 (m, 2H), 7.00 (m, 3H), 6.83 (m, 1H), 6.78 (m, 1H), 6.12 (m, 1H), 3.10 (m, 4H), 3.01 (m, 2H), 2.58 (m, 4H), 2.34 (m, 3H), 2.18 (s, 6H).

Example 10: Preparation of 4-(cyclopropyl(methyl)amino)-N-(3-((6-(4-(4-methylpiperazin-1-yl)phenyl)-7H-pyrrolo[2,3-d]pyrimidin-4-yl)oxy)phenyl)but-2-enamide

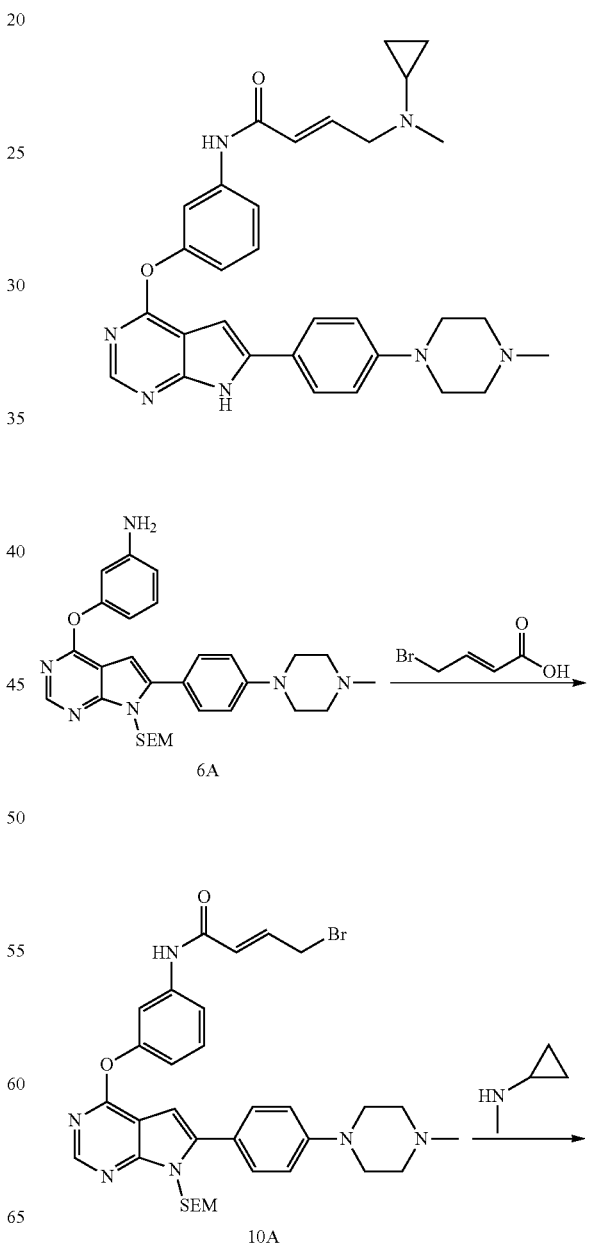

47
-continued

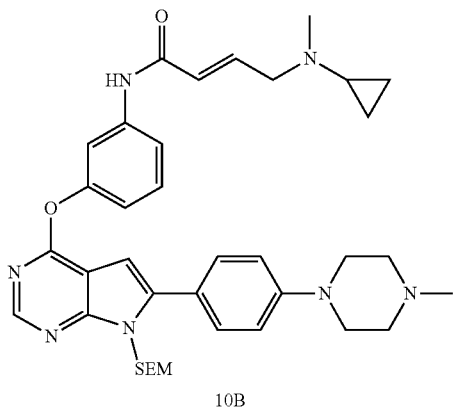

10B

Step 1: Synthesis of 4-bromo-N-(3-((6-(4-(4-methylpiperazin-1-yl)phenyl)-7-(2-(trimethylsilyl)ethoxy))-7H-pyrrolo[2,3-d]pyrimidin-4-yl)oxy)phenyl)but-2-enamide (Intermediate 10A)

4-Bromobut-2-enoic acid (164 mg, 1 mmol) was added to a three-necked flask equipped with a calcium chloride drying tube under argon atmosphere and added with anhydrous DCM (3 mL). The mixture was stirred until dissolved. Oxalyl chloride (139 mg, 1.1 mmol) and a drop of anhydrous DMF were added to the reaction flask. The reaction mixture was stirred for 4-5 h, and then concentrated to dryness.

3-((6-(4-(4-Methylpiperazin-1-yl)phenyl)-7-((2-(trimethylsilyl)ethoxy)methyl)-7H-pyrrolo[2,3-d]pyrimidin-4-yl)oxy)aniline (265 mg, 0.5 mmol) and THF (10 mL) were added to a flask successively and stirred at room temperature for 15 min. The mixture was added with at 0° C. was added NaHCO₃ (127 mg, 1.5 mmol) and distilled water (1 mL). The concentrated solution obtained above was dissolved in THF (1 mL) and then added to reaction flask at 0° C. The mixture was stirred at rt. for 20 h. The reaction mixture was added with DCM (50 mL) and washed with water (40 mL×3). The organic layer was separated and dried over anhydrous sodium sulfate overnight, and filtered. The filtrate was concentrated under reduced pressure. The residues were purified by column chromatography (eluent: DCM:MeOH, 12:1) to give 82 mg of the title compound as light grey solid (yield of 24.3%).

48

Step 2: Synthesis of 4-(cyclopropyl(methyl)amino)-N-(3-((6-(4-(4-methylpiperazin-1-yl) phenyl)-7-((2-(trimethylsilyl)ethoxy)methyl)-7H-pyrrolo[2,3-d]pyrimidin-4-yl)oxy)phenyl)but-2-enamide (Intermediate 10B)

4-Bromo-N-(3-((6-(4-(4-methylpiperazin-1-yl)phenyl)-7-(2-(trimethylsilyl)ethoxy))-7H-pyrrolo[2,3-d]pyrimidin-4-yl)oxy)phenyl)but-2-enamide (82 mg, 0.12 mmol) was dissolved in DMF (5 mL) and then added with N-methylcyclopropylamine (99 mg, 1.38 mmol) and potassium iodide (3.3 mg, 0.02 mmol) successively under ice bath. The reaction mixture was stirred at room temperature for 15 h. The reaction mixture was added with DCM (50 mL) and washed with water (40 mL×3). The organic layer was separated and dried over anhydrous sodium sulfate overnight, and filtered. The filtrate was concentrated under reduced pressure under reduced pressure to dryness. The residues were purified by column chromatography (eluent: DCM:MeOH, 6:1) to give 50 mg of the title compound as pale yellow solid (yield of 61.0%).

Step 3: Synthesis of 4-(cyclopropyl(methyl)amino)-N-(3-((6-(4-(4-methylpiperazin-1-yl)phenyl)-7H-pyrrolo[2,3-d]pyrimidin-4-yl)phenyl)but-2-enamide (Compound 10)

4-(Cyclopropyl(methyl)amino)-N-(3-((6-(4-(4-methylpiperazin-1-yl)phenyl)-7-((2-(trimethylsilyl)ethoxy)methyl)-7H-pyrrolo[2,3-d]pyrimidin-4-yl)oxy)phenyl)but-2-enamide 50 mg, 0.074 mmol was added to a 25 mL of flask and added with DCM (3 mL) and TFA (1 mL). The reaction mixture was stirred at rt. overnight. The reaction mixture was concentrated under reduced pressure. The residues were added with methanol (1 mL) and aqueous ammonia water (1 mL), and the mixture was stirred at room temperature for 1 h. After completion of the reaction, the reaction mixture was filtered and the filter cake was washed water and dried to give 31 mg of the title compound as pale yellow solid (yield of 54.3%, purity of 95.9%).

MS: m/z=538.5 [M+H]⁺.

¹H NMR (300 MHz, DMSO): δ 12.51 (s, 1H), 10.33 (s, 1H), 8.27 (m, 1H), 7.80 (m, 2H), 7.55 (m, 3H), 6.97 (m, 3H), 6.80 (m, 2H), 6.40 (m, 1H), 3.51 (m, 4H), 3.29 (m, 2H), 3.22 (m, 4H), 2.84 (m, 4H), 2.44 (s, 3H), 2.38 (m, 3H), 1.99 (m, 1H), 0.76 (m, 4H).

Example 11: Preparation of N-(3-((6-(4-(4-methylpiperazin-1-yl)phenyl)-7H-pyrrolo[2,3-d]pyrimidin-4-yl)oxy)phenyl)-4-(pyrrolidin-1-yl)but-2-enamide

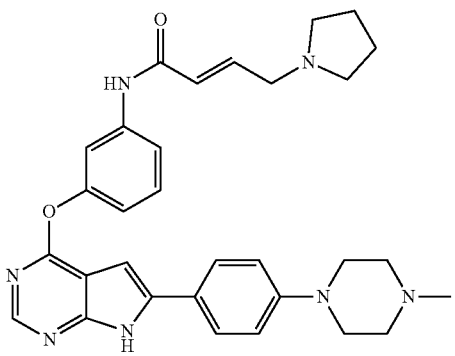 [SMILES: CN1CCN(c2ccc(-c3cc4c(Oc5cccc(NC(=O)/C=C/CN6CCCC6)c5)ncnc4[nH]3)cc2)CC1]

The preparation method was the same as that of Example 10, except that N-methylcycloprolylamine was replaced by tetrahydropyrrole to obtain the title compound.

MS: m/z=538.5 [M+H]$^+$.

$^1$H NMR (300 MHz, DMSO): δ 12.58 (s, 1H), 10.41 (s, 1H), 8.27 (m, 1H), 7.83 (m, 2H), 7.58 (m, 3H), 7.00 (m, 3H), 6.82 (m, 2H), 6.38 (m, 1H), 3.51 (m, 4H), 3.22 (m, 4H), 3.06 (m, 2H), 2.84 (m, 4H), 2.44 (s, 3H), 1.80 (m, 4H).

Example 12: Preparation of N-(3-((6-(4-(4-methylpiperazin-1-yl)phenyl)-7H-pyrrolo[2,3-d]pyrimidin-4-yl)oxy)phenyl) acrylamide

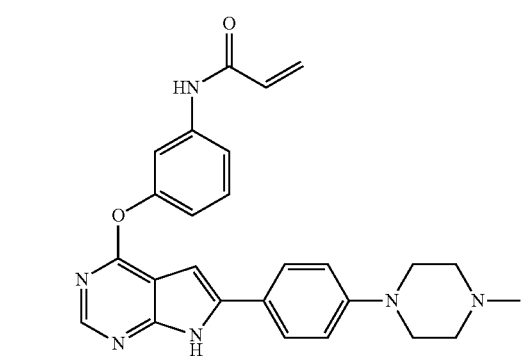 [SMILES: C=CC(=O)Nc1cccc(Sc2ncnc3[nH]c(-c4ccc(N5CCN(C)CC5)cc4)cc23)c1]

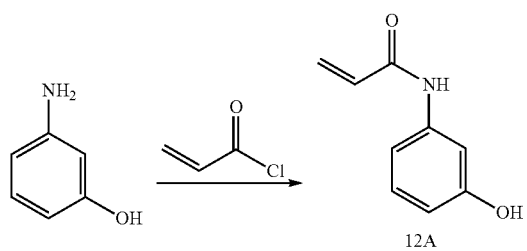

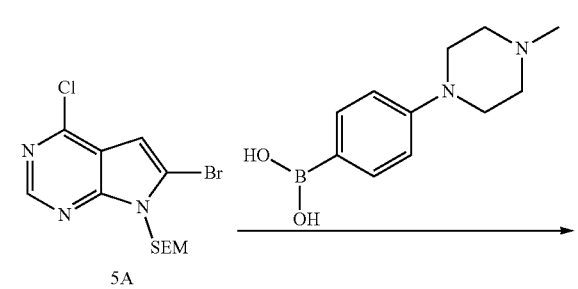

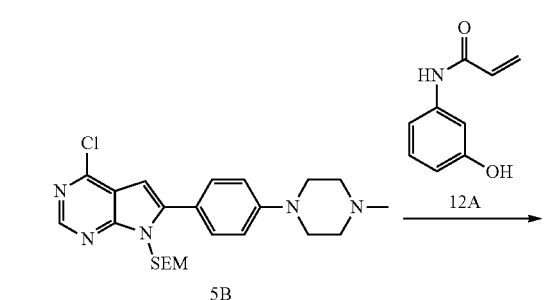

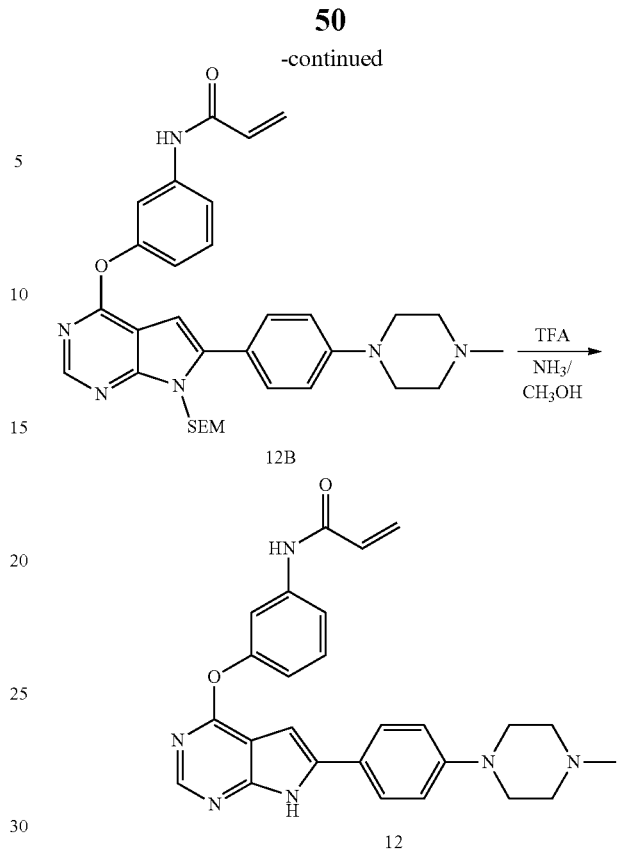

Step 1: Synthesis of N-(3-hydroxyphenyl)acrylamide (Intermediate 12A)

m-Aminophenol (10.0 g, 90 mmol), THF (200 mL), sodium bicarbonate (11.4 g, 135 mmol) and 30 mL of distilled water were added ton a flask successively, and then cooled to 0-10° C. under ice bath. A solution of acryloyl chloride (8.2 g, 90 mmol) in 50 mL of THF was added to the flask dropwish. After addition, the reaction mixture was warmed to room temperature and stirred overnight. After completion of the reaction, the reaction mixture was added with 100 mL of DCM and extracted with 100 mL of saturated ammonium chloride solution. The organic layers were washed with saturated ammonium chloride solution twice (100 mL each time), dried over anhydrous Na$_2$SO$_4$, and filtered. The filtrate was concentrated under reduced pressure under reduced pressure. The residues were purified by column chromatography (eluent: DCM:MeOH, 10:1) to give 12 g of the title compound as white solid (yield of 81.7%).

Step 2: Synthesis of 4-chloro-6-(4-(4-methylpiperazin-1-yl)phenyl)-7-((2-(trimethylsilyl)ethoxy)methyl)-7H-pyrrolo[2,3-d]pyrimidine (Intermediate 5B)

6-Bromo-4-chloro-7-((2-(trimethylsilyl)ethoxy)methyl)-7H-pyrrolo[2,3-d]pyrimidine (900 mg, 2.48 mmol) was added to a 100 mL of flask, and added with (4-(4-methylpiperazin-1-yl)phenyl)boronic acid (491 mg, 2.23 mmol), dioxane (50 mL), sodium carbonate (632 mg, 5.96 mmol), water (5 mL), Pd (dppf) Cl$_2$ (100 mg, 0.14 mmol). The reaction mixture was stirred at 80° C. for 4 h under argon atmosphere. The reaction mixture was cooled to rt. and concentrated under reduced pressure to dryness. The residues were purified by column chromatography (eluent: EtOAc) to give 600 mg of the title compound as brown oil (yield of 52.8%).

Step 3: Synthesis of N-(3-((6-(4-(4-methylpiperazin-1-yl)phenyl)-7-((2-(trimethylsilyl)ethoxy)methyl)-7H-pyrrolo[2,3-d]pyrimidin-4-yl)oxy)phenyl)acrylamide (Intermediate 12B)

4-Chloro-6-(4-(4-methylpiperazin-1-yl)phenyl)-7-((2-(trimethylsilyl)ethoxy)methyl)-7H-pyrrolo[2,3-d]pyrimidine (1.0 g, 2.2 mmol), N-(3-hydroxyphenyl)acrylamide (0.64 g, 3.9 mmol), sodium carbonate (0.8 g, 5.8 mmol), and DMF (10 mL) were added to a single neck flask. The reaction mixture was stirred at 100° C. for 4 h. The reaction solution was cooled to rt. and concentrated under reduced pressure to dryness. The residues were purified by column chromatography (eluent: DCM:MeOH, 30:1) to give 1.0 g of the title compound as yellow solid (yield of 78%).

Step 4: Synthesis of N-(3-((6-(4-(4-methylpiperazin-1-yl)phenyl)-7H-pyrrolo[2,3-d]pyrimidin-4-yl)oxy)phenyl) acrylamide (Compound 12)

N-(3-((6-(4-(4-methylpiperazin-1-yl)phenyl)-7-((2-(trimethylsilyl)ethoxy)methyl)-7H-pyrrolo[2,3-d]pyrimidin-4-yl)oxy)phenyl)acrylamide (1.0 g, 1.7 mmol) was added to a 50 mL of flask and added with DCM (5 mL) and TFA (5 mL). The reaction mixture was stirred at rt. overnight. The reaction mixture was concentrated under reduced pressure to dryness. The residues were added with methanol (20 mL) and ammonia water (3 mL) and then stirred at room temperature for 3 h. After completion of the reaction, the reaction mixture was added with saturated brine (10 mL), and extracted with DCM (20 mL). The organic layers were concentrated under reduced pressure to dryness. The residues were purified by column chromatography (eluent: DCM:MeOH, 10:1) to give 160 mg of the title compound as pale yellow solid (yield of 20.7%, purity of 95.6%).

MS: m/z=455.3[M+H]$^+$.

$^1$H NMR (300 MHz, DMSO): δ 12.53 (s, 1H), 10.30 (s, 1H), 8.27 (m, 1H), 7.80 (m, 2H), 7.68 (m, 1H), 7.44 (m, 2H), 7.00 (m, 3H), 6.82 (m, 1H), 6.40 (m, 1H), 6.28 (m, 1H), 5.77 (m, 1H), 3.66 (m, 4H), 3.16 (m, 4H), 2.44 (s, 3H).

Example 13: Preparation of N-(3-((6-(4-(4-methylpiperazin-1-yl)phenyl)-7H-pyrrolo[2,3-d]pyrimidin-4-yl)thio)phenyl) acrylamide The preparation method was the same as that of Example 5, except that m-phenylenediamine was replaced by m-aminothiophenol to give the title compound.

MS: m/z=471.3 [M+H]$^+$.

$^1$H NMR (300 MHz, DMSO): δ 12.69 (s, 1H), 10.54 (s, 1H), 8.31 (s, 1H), 7.91 (m, 1H), 7.73 (m, 3H), 7.48 (m, 2H), 7.06 (m, 3H), 6.88 (m, 1H), 6.45 (m, 1H), 6.29 (m, 1H), 5.83 (m, 1H), 3.76 (m, 4H), 3.10 (m, 4H), 2.79 (s, 3H).

Example 14: Preparation of N-(3-(methyl(6-(4-(4-methylpiperazin-1-yl)phenyl)-7H-pyrrolo[2,3-d]pyrimidin-4-yl)amino)phenyl) acrylamide

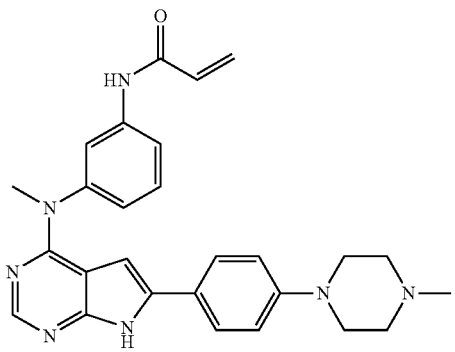 [SMILES: C=CC(=O)Nc1cccc(N(C)c2ncnc3[nH]c(-c4ccc(N5CCN(C)CC5)cc4)cc23)c1]

The preparation method was the same as that of Example 5, except that m-phenylenediamine was replaced by N-methyl-m-phenylenediamine to give the title compound.

MS: m/z=468.5 [M+H]$^+$.

$^1$H NMR (300 MHz, DSMO): δ 12.58 (s, 1H), 10.31 (s, 1H), 8.23 (s, 1H), 7.89 (m, 1H), 7.73 (m, 2H), 7.42 (m, 2H), 7.25 (m, 1H), 7.14 (m, 2H), 6.85 (m, 1H), 6.45 (m, 1H), 6.29 (m, 1H), 5.90 (m, 1H), 3.81 (m, 4H), 3.10 (m, 2H), 3.05 (m, 2H), 2.74 (s, 3H), 2.53 (s, 3H).

Example 15: Preparation of N-methyl-N-(3-((6-(4-(4-methylpiperazin-1-yl)phenyl)-7H-pyrrolo[2,3-d]pyrimidin-4-yl)oxy)phenyl)acrylamide

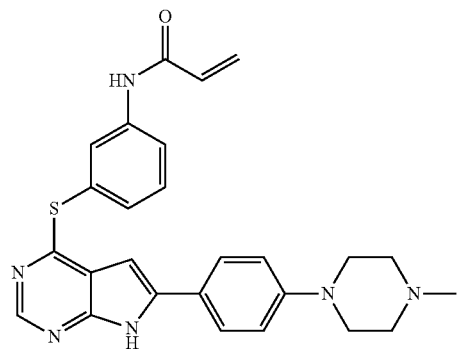

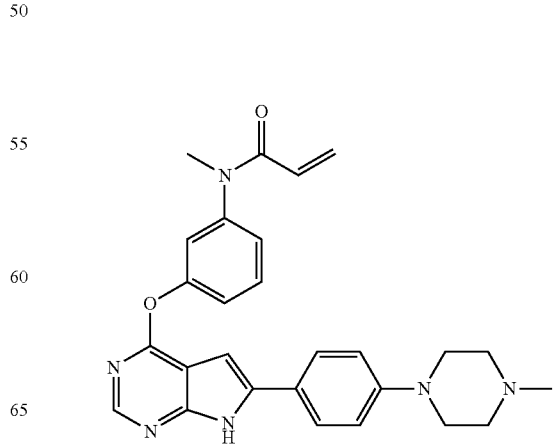

-continued

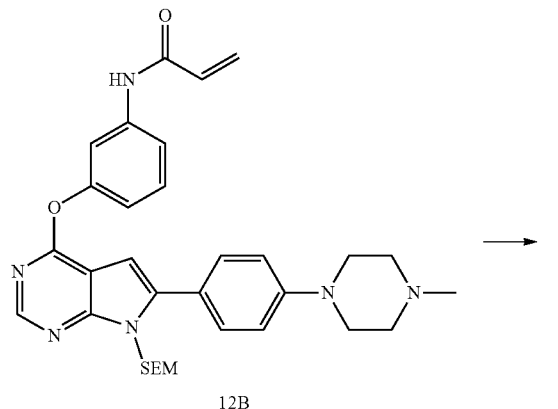

12B

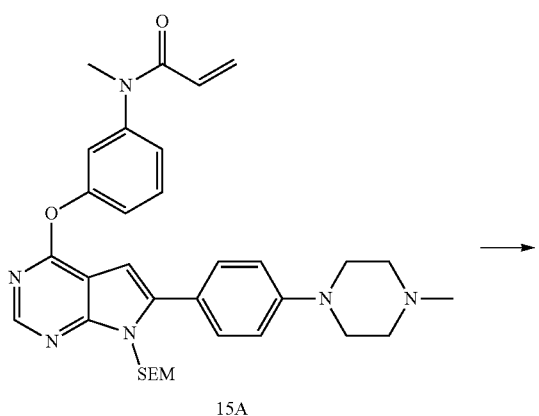

15A

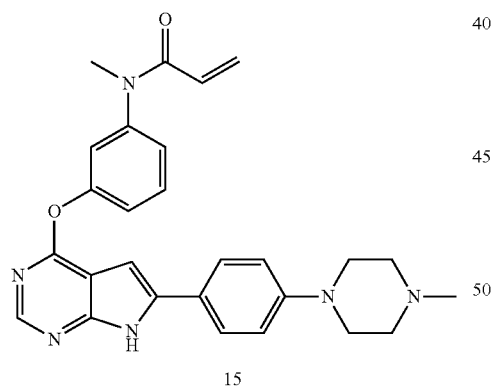

15

Step 1: Synthesis of N-methyl-N-(3-((6-(4-(4-methylpiperazin-1-yl)phenyl)-7-((2-(trimethylsilyl)ethoxy))methyl)-7H-pyrrolo[2,3-d]pyrimidin-4-yl)oxy)phenyl)acrylamide (Intermediate 15A)

N-(3-((6-(4-(4-Methylpiperazin-1-yl)phenyl)-7-((2-(trimethylsilyl)ethoxy)methyl)-7H-pyrrolo[2,3-d]pyrimidin-4-yl)oxy)phenyl)acrylamide (0.71 g, 1.22 mmol) and DMF (10 mL) were added to a 50 mL of single neck flask, and then added with NaH (0.04 g, 1.59 mmol) under ice bath and stirred for 30 min. Methyl iodide (0.17 g, 1.22 mmol) was added to DMF (5 mL) and added dropwise to the flask. After addition, the mixture was stirred at rt. for 4 h. After completion of the reaction, the reaction mixture was added with 30 mL of water and extracted with 30 mL of ethyl acetate. The organic layer was washed with saturated NaCl aqueous solution (30 mL) and water (30 mL) respectively, dried over anhydrous $Na_2SO_4$, and filtered. The filtrate was concentrated under reduced pressure under reduced pressure. The residues were purified by column chromatography (eluent: PE:EtOAc, 2:1) to give 260 mg of the title compound as pale yellow solid (yield of 35.8%, purity of 95.0%).

Step 2: Synthesis of N-methyl-N-(3-((6-(4-(4-methylpiperazin-1-yl)phenyl)-7H-pyrrolo[2,3-d]pyrimidin-4-yl)oxy)phenyl)acrylamide (compound 15)

N-methyl-N-(3-((6-(4-(4-methylpiperazin-1-yl)phenyl)-7-((2-(trimethylsilyl)ethoxy))methyl)-7H-pyrrolo[2,3-d]pyrimidin-4-yl)oxy)phenyl)acrylamide (260 mg, 0.43 mmol) was added to 25 mL of flask and added with DCM (3 mL) and TFA (3 mL). The reaction mixture was stirred at rt. overnight. The reaction mixture was concentrated under reduced pressure to dryness. The residues were added with methanol (3 mL) and aqueous ammonia (1 mL) and stirred at rt. for 1 h. After the completion of the reaction, the mixture was filtered and the filter cake was washed with water and dried to give 87 mg the title product as a pale yellow solid (yield: 42.7%, purity: 95.0%).

MS: m/z=469.3 [M+H]$^+$.

$^1$H NMR (300 MHz, DMSO): δ 12.57 (s, 1H), 8.26 (s, 1H), 7.82 (m, 2H), 7.73 (m, 1H), 7.58 (m, 1H), 7.38 (m, 1H), 6.99 (m, 3H), 6.79 (m, 1H), 6.40 (m, 1H), 6.27 (m, 1H), 5.75 (m, 1H), 3.35 (s, 3H), 3.26 (m, 4H), 2.45 (m, 4H), 2.32 (s, 3H).

Example 16: Preparation of N-methyl-N-(3-((6-(4-morpholinylphenyl)-7H-pyrrolo[2,3-d]pyrimidin-4-yl)oxy)phenyl)acrylamide

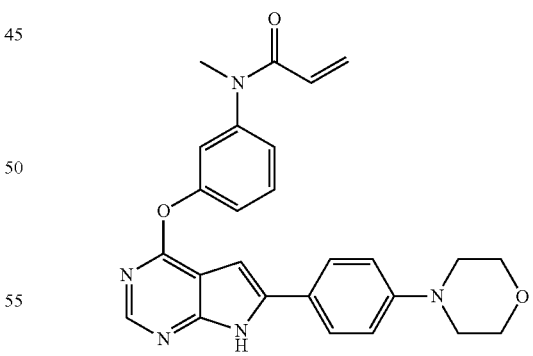

The preparation method was the same ad that of Example 16, except that (4-(4-methylpiperazin-1-yl)phenyl)boronic acid was replaced by (4-morpholinylphenyl)boronic acid to give the title compound.

MS: m/z=456.2 [M+H]$^+$.

$^1$H NMR (300 MHz, DMSO): δ 12.53 (s, 1H), 8.30 (m, 1H), 7.62 (m, 2H), 7.54 (m, 1H), 7.28 (m, 3H), 7.04 (m, 2H), 6.80 (m, 1H), 6.18 (m, 2H), 5.78 (m, 1H), 3.76 (m, 4H), 3.33 (m, 3H), 3.20 (m, 4H).

Example 17: Preparation of N-cyclopropyl-N-(3-((6-(4-(4-methylpiperazin-1-yl)phenyl)-7H-pyrrolo[2,3-d]pyrimidin-4-yl)oxy)phenyl)acrylamide

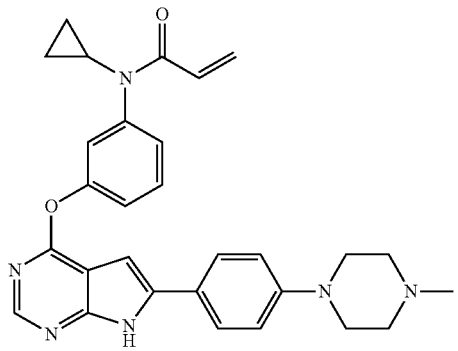 [SMILES: C=CC(=O)N(c1cccc(Oc2ncnc3[nH]c(-c4ccc(N5CCN(C)CC5)cc4)cc23)c1)C1CC1]

The preparation method was the same ad that of Example 16, except that methyl iodide was replaced by cyclopropyl bromide to give the title compound.

MS: m/z=495.6 [M+H]$^+$.

$^1$H NMR (300 MHz, DMSO): δ 12.39 (s, 1H), 8.35 (m, 1H), 7.73 (m, 3H), 7.50 (m, 1H), 7.31 (m, 1H), 7.08 (m, 3H), 6.79 (m, 1H), 6.31 (m, 2H), 5.73 (m, 1H), 3.83 (m, 1H), 3.77 (m, 4H), 2.90 (m, 4H), 2.38 (m, 3H), 1.23 (m, 2H), 0.99 (m, 2H).

Example 18: Preparation of N-(2-fluoro-5-((6-(4-(4-methylpiperazin-1-yl)phenyl)-7H-pyrrolo[2,3-d]pyrimidin-4-yl)oxy)phenyl)acrylamide

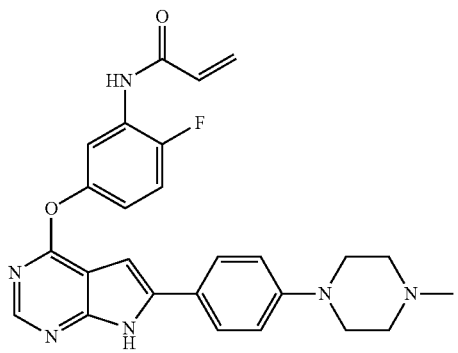 [SMILES: C=CC(=O)Nc1cc(Oc2ncnc3[nH]c(-c4ccc(N5CCN(C)CC5)cc4)cc23)ccc1F]

The preparation method was the same ad that of Example 12, except that m-aminophenol was replaced by 3-amino-4-fluorophenol to give the title compound.

MS: m/z=473.1 [M+H]$^+$.

$^1$H NMR (300 MHz, DMSO): δ 12.53 (s, 1H), 10.10 (s, 1H), 8.26 (m, 1H), 8.02 (m, 1H), 7.81 (m, 2H), 7.32 (m, 1H), 7.05 (m, 3H), 6.85 (m, 1H), 6.63 (m, 1H), 6.28 (m, 1H), 5.78 (m, 1H), 3.24 (m, 4H), 2.48 (m, 4H), 2.23 (m, 3H).

Example 19: Preparation of N-(2-Fluoro-5-((6-(4-morpholinylphenyl)-7H-pyrrolo[2,3-d]pyrimidin-4-yl)oxy)phenyl)acrylamide

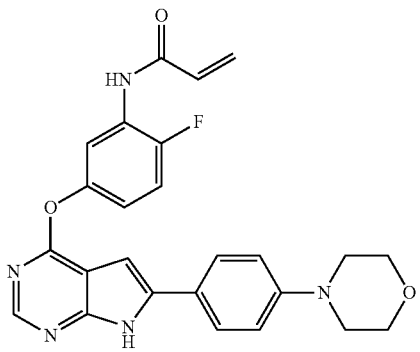

The preparation method was the same as that of Example 12, except that m-aminophenol was replaced by 3-amino-4-fluorophenol in step 1 and (4-(4-methylpiperazin-1-yl)phenyl)boronic acid was replaced by (4-morpholinylphenyl)boronic acid in step 2 to give the title compound.

MS: m/z=460.2 [M+H]$^+$.

$^1$H NMR (300 MHz, DMSO): δ 12.55 (s, 1H), 10.11 (s, 1H), 8.27 (m, 1H), 8.02 (m, 1H), 7.84 (m, 2H), 7.37 (m, 1H), 7.09 (m, 3H), 6.88 (m, 1H), 6.66 (m, 1H), 6.26 (m, 1H), 5.79 (m, 1H), 3.76 (m, 4H), 3.22 (m, 4H).

Example 20: Preparation of N-(4-((6-(4-morpholinyl)-7H-pyrrolo[2,3-d]pyrimidin-4-yl)oxy)pyridin-2-yl)acrylamide

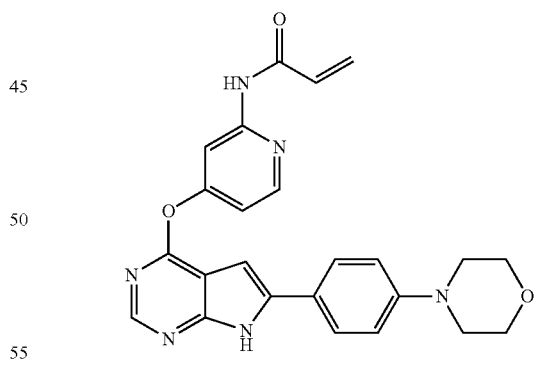

The preparation method was the same as that of Example 12, except that m-aminophenol was replaced by 3-aminopyridin-4-ol in step 1 and (4-(4-methylpiperazin-1-yl)phenyl)boronic acid was replaced by (4-morpholinylphenyl)boronic acid in step 2 to give the title compound.

MS: m/z=443.2 [M+H]$^+$.

$^1$H NMR (300 MHz, DMSO): δ 12.60 (s, 1H), 10.20 (s, 1H), 8.31 (m, 1H), 8.12 (m, 1H), 7.99 (m, 1H), 7.80 (m, 2H), 7.33 (m, 1H), 7.06 (m, 2H), 6.85 (m, 1H), 6.66 (m, 1H), 6.27 (m, 1H), 5.76 (m, 1H), 3.76 (m, 4H), 3.20 (m, 4H).

Example 21: Preparation of N-(2-methyl-5-((6-(4-morpholinylphenyl)-7H-pyrrolo[2,3-d]pyrimidin-4-yl)oxy)phenyl)acrylamide

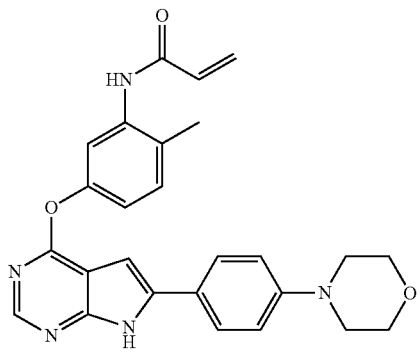 [SMILES: C=CC(=O)Nc1cc(Oc2ncnc3[nH]c(-c4ccc(N5CCOCC5)cc4)cc23)ccc1C]

The preparation method was the same as that of Example 12, except that m-aminophenol was replaced by 3-amino-4-methylphenol in step 1 and (4-(4-methylpiperazin-1-yl)phenyl)boronic acid was replaced by (4-morpholinylphenyl)boronic acid in step 2 to give the title compound.

MS: m/z=456.3 [M+H]$^+$.

$^1$H NMR (300 MHz, DMSO): δ 12.57 (s, 1H), 10.17 (s, 1H), 8.31 (m, 1H), 7.70 (m, 2H), 7.55 (m, 1H), 7.28 (m, 2H), 7.06 (m, 3H), 6.81 (m, 1H), 6.21 (m, 2H), 5.78 (m, 1H), 3.75 (m, 4H), 3.19 (m, 4H), 2.29 (s, 3H).

Example 22: Preparation of N-(2-Methoxy-5-((6-(4-(4-methylpiperazin-1-yl)phenyl)-7H-pyrrolo[2,3-d]pyrimidin-4-yl)oxy)phenyl)acrylamide

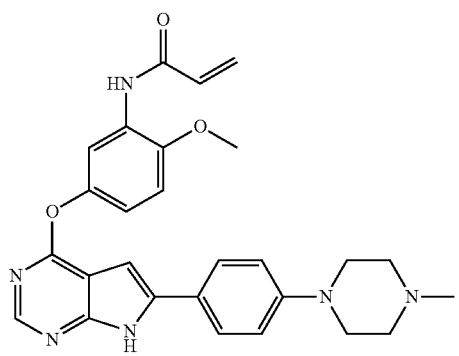 [SMILES: C=CC(=O)Nc1cc(Oc2ncnc3[nH]c(-c4ccc(N5CCN(C)CC5)cc4)cc23)ccc1OC]

The preparation method was the same as that of Example 12, except that m-aminophenol was replaced by 3-amino-4-methoxyphenol to give the title compound.

MS: m/z=485.4 [M+H]$^+$.

$^1$H NMR (300 MHz, DMSO): δ 12.51 (s, 1H), 10.19 (s, 1H), 8.27 (m, 1H), 7.63 (m, 2H), 7.58 (m, 1H), 7.21 (m, 2H), 7.03 (m, 2H), 6.75 (m, 1H), 6.25 (m, 2H), 5.69 (m, 1H), 3.86 (s, 3H), 3.69 (m, 4H), 2.85 (m, 4H), 2.33 (s, 3H).

Example 23: Preparation of N-(2-cyano-5-((6-(4-(4-methylpiperazin-1-yl)phenyl)-7H-pyrrolo[2,3-d]pyrimidin-4-yl)oxy)phenyl)acrylamide The preparation method was the same as that of Example 12, except that m-aminophenol was replaced by 3-amino-4-cyanophenol to give the title compound.

MS: m/z=480.5 [M+H]$^+$.

$^1$H NMR (300 MHz, DMSO): δ 12.63 (s, 1H), 10.15 (s, 1H), 8.30 (m, 1H), 7.61 (m, 2H), 7.51 (m, 1H), 7.23 (m, 2H), 6.99 (m, 2H), 6.81 (m, 1H), 6.29 (m, 2H), 5.70 (m, 1H), 3.72 (m, 4H), 2.88 (m, 4H), 2.33 (s, 3H).

Example 24: Preparation of N-(3-((6-(6-(4-methylpiperazin-1-yl)pyridin-3-yl)-7H-pyrrolo[2,3-d]pyrimidin-4-yl)oxy)phenyl)acrylamide The preparation method was the same as that of Example 12, except that (4-(4-methylpiperazin-1-yl)phenyl)boronic acid was replaced by (6-(4-methylpiperazin-1-yl)pyridin-3-yl)boronic acid to give the title compound.

MS: m/z=456.6 [M+H]$^+$.

$^1$H NMR (300 MHz, DMSO): δ 12.49 (s, 1H), 10.53 (s, 1H), 8.73 (m, 1H), 8.35 (m, 1H), 7.73 (m, 2H), 7.50 (m, 1H), 7.31 (m, 1H), 7.08 (m, 1H), 6.83 (m, 2H), 6.32 (m, 2H), 5.67 (m, 1H), 3.66 (m, 4H), 2.84 (m, 4H), 2.31 (s, 3H).

Example 25: Preparation of N-(3-((6-(3-fluoro-4-(4-methylpiperazin-1-yl)phenyl)-7H-pyrrolo[2,3-d]pyrimidin-4-yl)oxy)phenyl)acrylamide

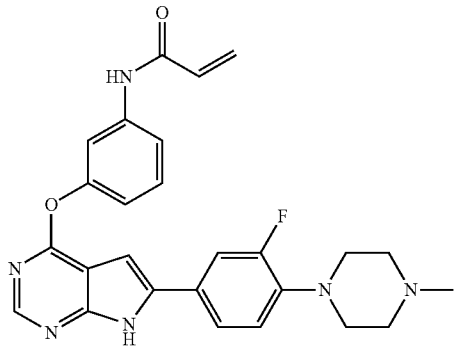

The preparation method was the same as that of Example 12, except that (4-(4-methylpiperazin-1-yl)phenyl)boronic acid was replaced by (3-fluoro-4-(4-methylpiperazin-1-yl)phenyl)boronic acid pinacol ester (prepared according to WO 2012167733) to give the title compound.

MS: m/z=473.4 [M+H]+.

1H NMR (300 MHz, DMSO): δ 12.48 (s, 1H), 10.41 (s, 1H), 8.27 (s, 1H), 7.79 (m, 1H), 7.59 (m, 2H), 7.39 (m, 2H), 6.97 (m, 2H), 6.80 (m, 1H), 6.40 (m, 1H), 6.22 (m, 1H), 5.72 (m, 1H), 3.39 (m, 4H), 2.94 (m, 4H), 2.27 (s, 3H).

Example 26: Preparation of N-(3-((6-(3-methoxy-4-(4-methylpiperazin-1-yl)phenyl)-7H-pyrrolo[2,3-d]pyrimidin-4-yl)oxy)phenyl)acrylamide

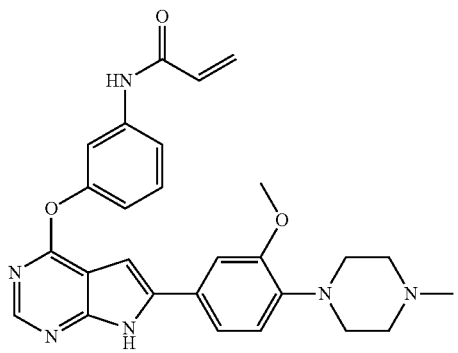 [SMILES: C=CC(=O)Nc1cccc(Oc2ncnc3[nH]c(-c4ccc(N5CCN(C)CC5)c(OC)c4)cc23)c1]

The preparation method was the same as that of Example 12, except that (4-(4-methylpiperazin-1-yl)phenyl)boronic acid was replaced by (3-methoxy-4-(4-methylpiperazin-1-yl)phenyl)boronic acid pinacol ester (prepared according to WO 2013053051) to give the title compound.

MS: m/z=485.5 [M+H]+.

1H NMR (300 MHz, DMSO): δ 12.39 (s, 1H), 10.17 (s, 1H), 8.29 (s, 1H), 7.69 (m, 3H), 7.40 (m, 2H), 7.09 (m, 2H), 6.83 (m, 1H), 6.33 (m, 1H), 6.25 (m, 1H), 5.73 (m, 1H), 3.95 (s, 3H), 3.56 (m, 4H), 2.71 (m, 4H), 2.38 (s, 3H), 2.21 (s, 3H).

Example 27: Preparation of N-(3-((6-(3-methyl-4-(4-methylpiperazin-1-yl)phenyl)-7H-pyrrolo[2,3-d]pyrimidin-4-yl)oxy)phenyl)acrylamide

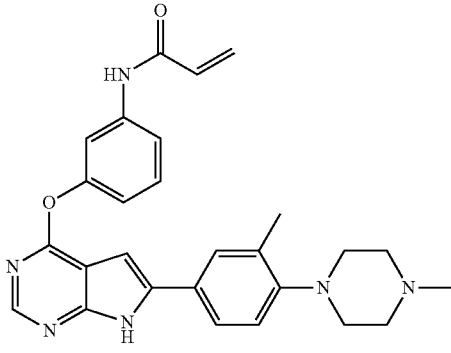 [SMILES: C=CC(=O)Nc1cccc(Oc2ncnc3[nH]c(-c4ccc(N5CCN(C)CC5)c(C)c4)cc23)c1]

The preparation method was the same as that of Example 12, except that (4-(4-methylpiperazin-1-yl)phenyl)boronic acid was replaced by (3-methyl-4-(4-methylpiperazin-1-yl)phenyl)boronic acid pinacol ester (prepared according to WO 2012048411) to give the title compound.

MS: m/z=469.3 [M+H]+.

1H NMR (300 MHz, DMSO): δ 12.50 (s, 1H), 10.31 (s, 1H), 8.24 (s, 1H), 7.79 (m, 2H), 7.65 (m, 1H), 7.37-7.47 (m, 2H), 6.95-7.01 (m, 2H), 6.80 (m, 1H), 6.40 (m, 1H), 6.22 (m, 1H), 5.73 (m, 1H), 3.56 (m, 4H), 2.99 (m, 4H), 2.38 (s, 3H), 2.21 (s, 3H).

Example 28: Preparation of N-(3-((6-(3-(Difluoromethoxy)-4-(4-methylpiperazin-1-yl)phenyl)-7H-pyrrolo[2,3-d]pyrimidine-4-yl)oxy)phenyl)acrylamide

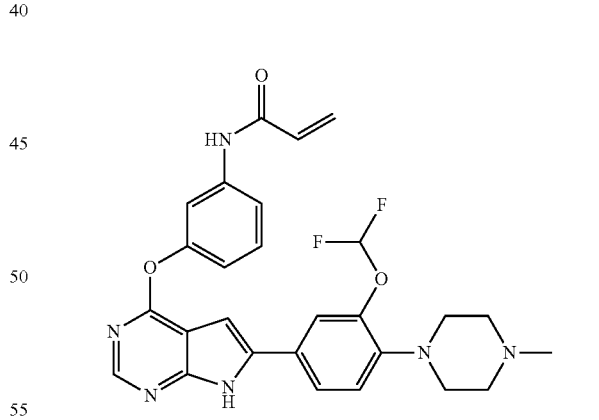

The preparation method was the same as that of Example 12, except that (4-(4-methylpiperazin-1-yl)phenyl)boronic acid was replaced by (3-(difluoromethoxy)-4-(4-methylpiperazin-1-yl)phenyl)boronic acid pinacol ester to give the title compound.

MS: m/z=520.3 [M+H]+.

1H NMR (300 MHz, DMSO): δ 12.39 (s, 1H), 10.33 (s, 1H), 8.27 (s, 1H), 7.80 (m, 1H), 7.63 (m, 2H), 7.40 (m, 3H), 6.98 (m, 2H), 6.80 (m, 1H), 6.38 (m, 1H), 6.26 (m, 1H), 5.69 (m, 1H), 3.56 (m, 4H), 2.96 (m, 4H), 2.28 (s, 3H).

Example 29: Preparation of N-(3-((6-(4-(dimethylamino)phenyl)-7H-pyrrolo[2,3-d]pyrimidin-4-yl)oxy)phenyl)acrylamide

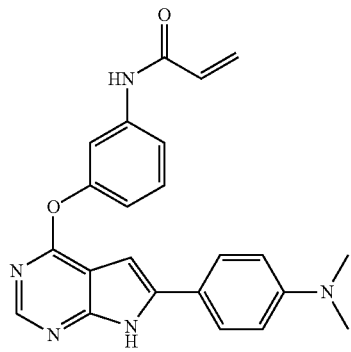 [SMILES: C=CC(=O)Nc1cccc(Oc2ncnc3[nH]c(-c4ccc(N(C)C)cc4)cc23)c1]

The preparation method was the same as that of Example 12, except that (4-(4-methylpiperazin-1-yl)phenyl)boronic acid was replaced by (4-(dimethylamino)phenyl)boronic acid to give the title compound.

MS: m/z=400.5 [M+H]$^+$.

$^1$H NMR (300 MHz, DMSO): δ 12.55 (s, 1H), 10.19 (s, 1H), 8.31 (m, 1H), 7.83 (m, 2H), 7.63 (m, 1H), 7.40 (m, 2H), 6.99 (m, 3H), 6.79 (m, 1H), 6.31 (m, 2H), 5.76 (m, 1H), 3.11 (s, 6H).

Example 30: Preparation of N-(3-((6-(4-((dimethylamino)methyl)phenyl)-7H-pyrrolo[2,3-d]pyrimidin-4-yl)oxy)phenyl)acrylamide

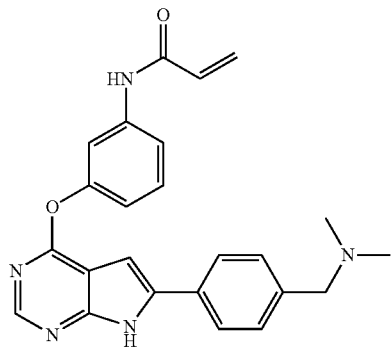 [SMILES: C=CC(=O)Nc1cccc(Oc2ncnc3[nH]c(-c4ccc(CN(C)C)cc4)cc23)c1]

The preparation method was the same as that of Example 12, except that (4-(4-methylpiperazin-1-yl)phenyl)boronic acid was replaced by (4-((dimethylamino)methyl)phenyl)boronic acid to give the title compound.

MS: m/z=414.4 [M+H]$^+$.

$^1$H NMR (300 MHz, DMSO): δ 12.59 (s, 1H), 10.11 (s, 1H), 8.29 (m, 1H), 7.79 (m, 2H), 7.60 (m, 1H), 7.41 (m, 2H), 7.00 (m, 3H), 6.80 (m, 1H), 6.26 (m, 2H), 5.76 (m, 1H), 3.57 (m, 2H), 2.30 (s, 6H).

Example 31: Preparation of N-(3-((6-(4-(2-methoxyethoxy)phenyl)-7H-pyrrolo[2,3-d]pyrimidin-4-yl)oxy)phenyl)acrylamide

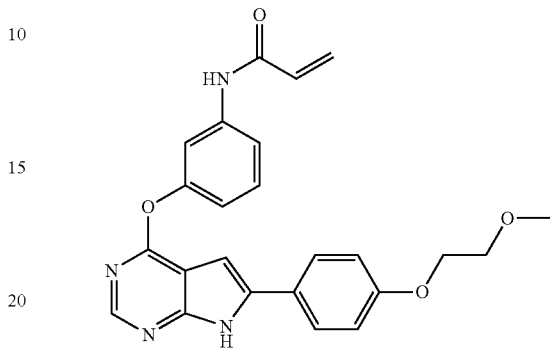

The preparation method was the same as that of Example 12, except that (4-(4-methylpiperazin-1-yl)phenyl)boronic acid was replaced by (4-(2-methoxyethoxy)phenyl)boronic acid to give the title compound.

MS: m/z=431.3 [M+H]$^+$.

$^1$H NMR (300 MHz, DMSO): δ 12.60 (s, 1H), 10.17 (s, 1H), 8.23 (m, 1H), 7.73 (m, 2H), 7.58 (m, 1H), 7.39 (m, 2H), 7.03 (m, 3H), 6.75 (m, 1H), 6.29 (m, 2H), 5.76 (m, 1H), 4.28 (m, 2H), 3.66 (m, 2H), 3.42 (s, 3H).

Example 32: Preparation of N-(3-((6-(4-morpholinylphenyl)-7H-pyrrolo[2,3-d]pyrimidin-4-yl)amino)phenyl) acrylamide

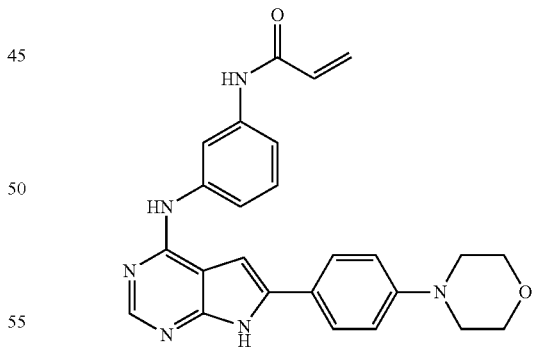

The preparation method was the same as that of Example 6, except that (4-(4-methylpiperazin-1-yl)phenyl)boronic acid was replaced by (4-morpholinylphenyl)boronic acid to give the title compound.

MS: m/z=441.2 [M+H]$^+$.

$^1$H NMR (300 MHz, DMSO): δ 12.14 (s, 1H), 10.21 (s, 1H), 9.37 (m, 1H), 8.27 (m, 2H), 7.70 (m, 3H), 7.30 (m, 2H), 7.06 (m, 3H), 6.50 (m, 1H), 6.30 (m, 1H), 6.24 (m, 1H), 5.75 (m, 1H), 3.76 (m, 4H), 3.16 (m, 4H).

Example 33: Preparation of N-(3-((6-(4-morpholinylphenyl)-7H-pyrrolo[2,3-d]pyrimidin-4-yl)oxy)phenyl)acrylamide

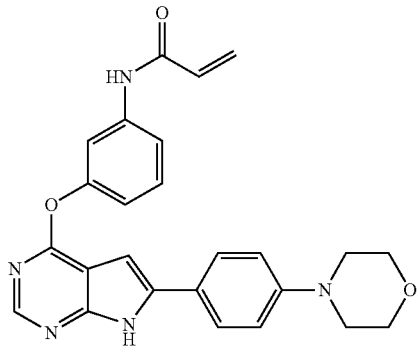 [SMILES: C=CC(=O)Nc1cccc(Oc2ncnc3[nH]c(-c4ccc(N5CCOCC5)cc4)cc23)c1]

The preparation method was the same as that of Example 12, except that (4-(4-methylpiperazin-1-yl)phenyl)boronic acid was replaced by (4-morpholinylphenyl)boronic acid to give the title compound.

MS: m/z=442.1 [M+H]$^+$.

$^1$H NMR (300 MHz, DMSO): δ 12.84 (s, 1H), 10.68 (s, 1H), 8.35 (m, 1H), 7.99 (m, 3H), 7.78 (m, 1H), 7.60 (m, 1H), 7.45 (m, 2H), 7.02 (m, 1H), 6.57 (m, 2H), 6.29 (m, 1H), 6.24 (m, 1H), 3.91 (m, 4H), 3.42 (m, 4H).

Example 34: Preparation of N-(3-((6-(4-(piperazin-1-yl)phenyl)-7H-pyrrolo[2,3-d]pyrimidin-4-yl)oxy)phenyl)acrylamide

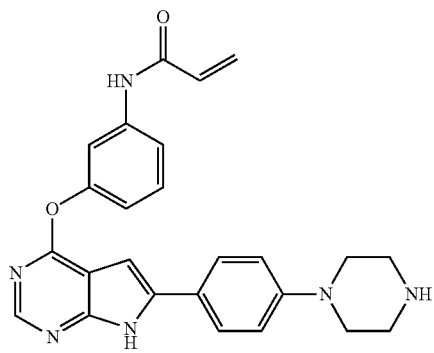 [SMILES: C=CC(=O)Nc1cccc(Oc2ncnc3[nH]c(-c4ccc(N5CCNCC5)cc4)cc23)c1]

The preparation method was the same as that of Example 12, except that (4-(4-methylpiperazin-1-yl)phenyl)boronic acid was replaced by 4-(4-Boc-1-piperazinyl)phenyl)boronic acid pinacol ester to give the title compound.

MS: m/z=441.2 [M+H]$^+$.

$^1$H NMR (600 MHz, DMSO): δ 12.55 (s, 1H), 10.29 (s, 1H), 8.78 (s, 2H), 8.26 (m, 1H), 7.85 (m, 2H), 7.68 (m, 1H), 7.37 (m, 2H), 6.71-7.17 (m, 6H), 6.21-6.38 (m, 2H), 5.73 (m, 1H), 3.43 (m, 4H), 3.23 (m, 4H).

Example 35: Preparation of N-(3-((6-(4-(1,1-dioxothiomorpholinyl)phenyl)-7H-pyrrolo[2,3-d]pyrimidin-4-yl)oxy)phenyl)acrylamide

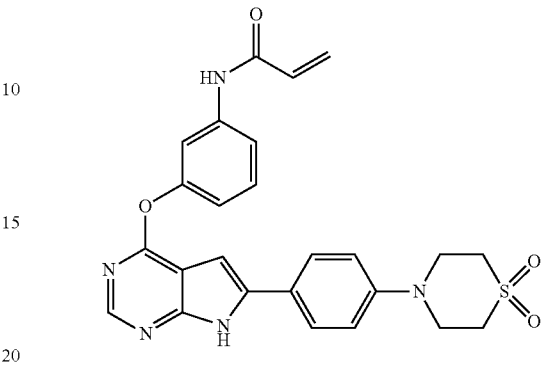

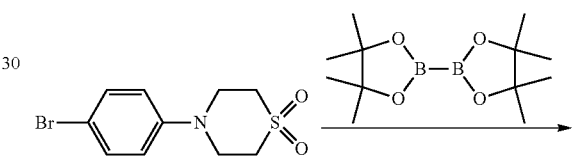

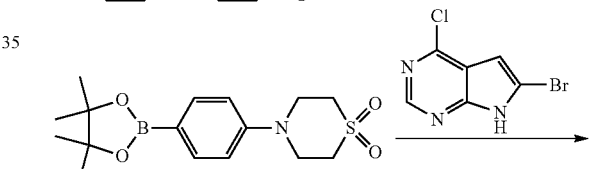

35A

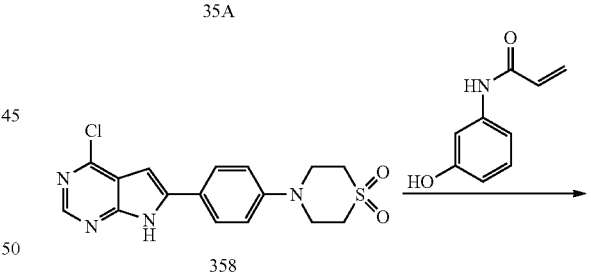

358

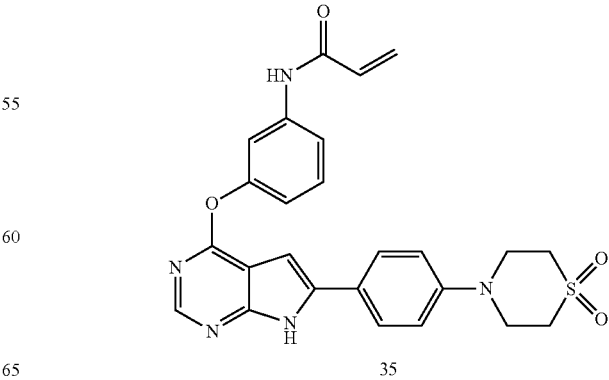

35

Step 1: synthesis of (4-(1,1-dioxothiomorpholinyl)phenyl)boronic acid pinacol ester (intermediate 35A)

4-(4-Bromophenyl)thiomorpholine-1,1-dioxide (2.0 g, 6.8 mmol) was added to a 100 mL of flask and added with potassium acetate (1.36 g, 14.0 mmol), dioxane (40 mL), Pd(dppf)Cl$_2$ (0.48 g, 0.6 mmol), and biborate pinacol ester (1.2 g, 4.8 mmol) successively. The reaction mixture was stirred at 80° C. under argon atmosphere for 16 hours. The reaction mixture was cooled to rt. and concentrated under reduced pressure to dryness. The residues were purified by column chromatography (eluent: PE:EtOAc, 3:1) to give 1.1 g of the title compound as pale yellow solid (yield of 48.2%).

Step 2: synthesis of 4-(4-(4-chloro-7H-pyrrolo[2,3-d]pyrimidin-6-yl)phenyl)thiomorpholine-1,1-dioxide (Intermediate 35B)

(4-(1,1-Dioxothiomorpholinyl)phenyl)boronic acid pinacol ester (1.1 g, 3.3 mmol) was added to a 100 mL of flask and added with 6-bromo-4-chloro-7-((2-(trimethylsilyl)ethoxy)methyl)-7H-pyrrolo[2,3-d]pyrimidine (440 mg 1.90 mmol), potassium carbonate (0.53 g, 3.8 mmol), dioxane (40 mL), Pd (dppf) Cl$_2$ (139 mg, 0.18 mmol), and water (4 mL) successively. The reaction mixture was stirred at 80° C. for 16 h under argon atmosphere. The reaction mixture was cooled to rt. and concentrated under reduced pressure to dryness. The residues were purified by column chromatography (eluent: PE:EtOAc, 3:1) to give 100 mg of the title compound as pale yellow solid (yield of 14.5%).

Step 3: Synthesis of N-(3-((6-(4-(1,1-dioxothiomorpholinyl)phenyl)-7H-pyrrolo[2,3-d]pyrimidin-4-yl)oxy)phenyl)acrylamide (compound 35)

4-(4-(4-Chloro-7H-pyrrolo[2,3-d]pyrimidin-6-yl)phenyl)thiomorpholine-1,1-dioxide (100 mg, 0.28 mmol), N-(3-hydroxyphenyl)acrylamide (50 mg, 0.31 mmol), potassium carbonate (75 mg, 0.54 mmol) and DMF (10 mL) were added to a single neck flask successively. The reaction mixture was stirred at 130° C. for 4 h. The reaction mixture was cooled to rt. and concentrated under reduced pressure to dryness. The residues were purified by column chromatography (eluent: DCM:MeOH, 40:1) to give 5 mg of the title compound as yellow solid (yield of 3.7%).
MS: m/z=490.3 [M+H]$^+$.
$^1$H NMR (300 MHz, DMSO): δ 12.67 (s, 1H), 10.38 (s, 1H), 8.29 (m, 1H), 7.88 (m, 2H), 7.65 (m, 1H), 7.45 (m, 4H), 7.02 (m, 2H), 6.27 (m, 2H), 5.79 (m, 1H), 3.21 (m, 4H), 2.98 (m, 4H).

Example 36: Preparation of N-(3-((6-(4-(4-(2,2,2-trifluoroethyl)piperazin-1-yl)phenyl)-7H-pyrrolo[2,3-d]pyrimidine-4-yl)oxy)phenyl)acrylamide

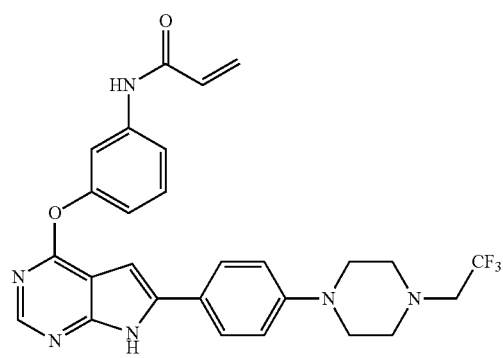

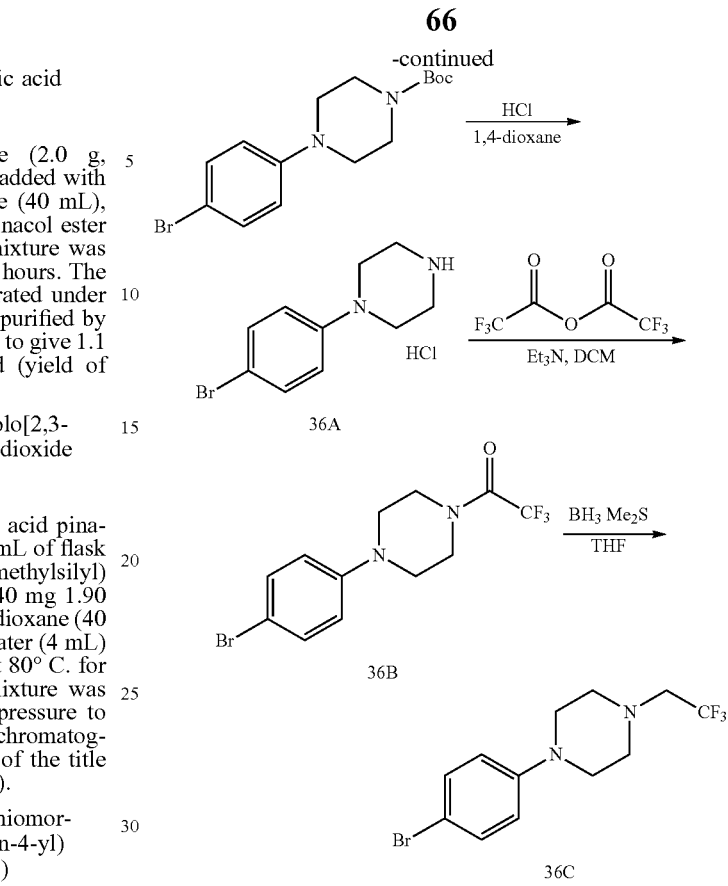

Step 1: Synthesis of 1-(4-bromophenyl)piperazine hydrochloride (Intermediate 36A)

Tert-butyl 4-(4-bromophenyl)piperazin-1-carboxylate (2.6 g, 7.65 mmol) was dissolved in 4M hydrochloric acid/dioxane (50 mL). The reaction mixture was stirred at rt. for 24 h and then concentrated under reduced pressure to give 2.5 g of the title compound as white solid (yield of 100%).

Step 2: Synthesis of 1-(4-(4-Bromophenyl)piperazin-1-yl)-2,2,2-trifluoroethyl-1-one (Intermediate 36B)

1-(4-Bromophenyl)piperazine hydrochloride (900 mg, 3.24 mmol) was dissolved in DCM (50 mL) and added with triethylamine (1.5 g, 15 mmol). The mixture was added with trifluoroacetic anhydride (900 mg, 4.29 mmol) dropwise. The mixture was stirred at room temperature for 16 hours. The reaction mixture was added with water (50 mL). The organic layer was washed with saturated brine (50 mL), dried over anhydrous sodium sulfate, and filtered. The filtrate was concentrated under reduced pressure. The residues were purified by column chromatography (eluent: DCM:MeOH, 50:1 to 20:1) to give 1000 mg of the title compound as yellow solid (yield of 92.6%).

Step 3: Synthesis of 1-(4-bromophenyl)-4-(2,2,2-trifluoroethyl) piperazine (Intermediate 36C)

1-(4-(4-Bromophenyl)piperazin-1-yl)-2,2,2-trifluoroethyl-1-one (1.00 g, 3.00 mmol) was dissolved in anhydrous THF (30 mL) and added with borane dimethyl sulfide (10 M, 1.5 mL). The reaction mixture was stirred under reflux for 6 h and then cooled to room temperature. The reaction mixture was added with MeOH dropwise and then concentrated to under pressure dryness. The residues were purified by column chromatography (eluent: DCM:MeOH, 50:1 to 20:1) to give 900 mg of the title compound as yellow solid (yield of 93.2%).

The following steps were the same as Example 35, except that 4-(4-bromophenyl)thiomorpholine-1,1-dioxide was replaced by 1-(4-bromophenyl)-4-(2,2,2-trifluoroethyl)piperazine to give the title compound.

MS: m/z=523.2 [M+H]$^+$.

$^1$H NMR (600 MHz, DMSO): δ 12.50 (s, 1H), 10.26 (s, 1H), 8.24 (s, 1H), 7.79 (m, 2H), 7.65 (m, 1H), 7.37-7.47 (m, 2H), 6.95-7.01 (m, 3H), 6.80 (m, 1H), 6.40 (m, 1H), 6.22 (m, 1H), 5.73 (m, 1H), 3.23 (m, 6H), 2.74 (m, 4H).

Example 37: Preparation of N-(3-((6-(4-(6-methyl-2,6-diazaspiro[3.3]heptan-2-yl)phenyl)-7H-pyrrolo[2,3-d]pyrimidin-4-yl)oxy)phenyl)acrylamide

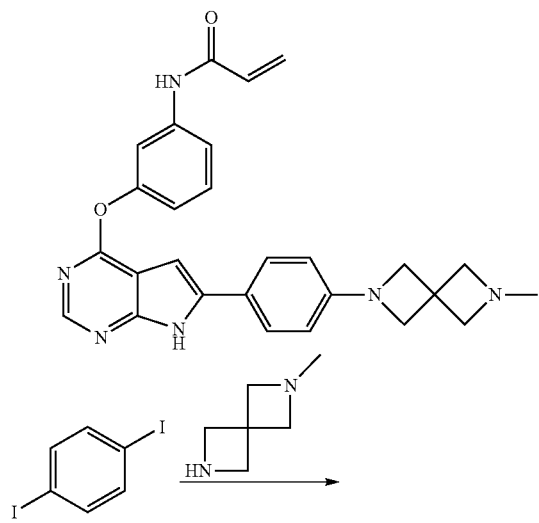

Step 1: Preparation of 2-(4-iodophenyl)-6-methyl-2,6-diazaspiro[3.3]heptane (intermediate 37A)

p-Diiodobenzene (3.30 g, 10 mmol). 6-methyl-2,6-diazaspiro[3.3]heptane oxalate (2.02 g, 10 mmol), potassium phosphate (4.24 g, 20 mmol), cuprous iodide (0.19 g, 1 mmol) and 1,1'-bi-2-naphthol (0.28 g, 1 mmol) was added in DMF (20 mL) successively under nitrogen atmosphere. The reaction mixture was stirred at rt. for 48 h, and then added with water (40 mL) and extracted with EtOAc (30 mL×3). The combined organic layer was dried over anhydrous sodium sulfate and filtered. The filtrate was concentrated under reduced pressure under reduced pressure. The residues were purified by column chromatography (eluent: DCM:MeOH, 50:1 to 20:1) to give 2.13 g of the title compound as yellow oil (yield of 67.8%).

The following steps were the same as Example 35, except that 4-(4-bromophenyl)thiomorpholine-1,1-dioxide was replaced by 2-(4-iodophenyl)-6-methyl-2,6-diazaspiro[3.3]heptane to give the title compound.

MS: m/z=467.3 [M+H]$^+$.

$^1$H NMR (300 MHz, DMSO): δ 12.62 (s, 1H), 10.30 (s, 1H), 8.22 (s, 1H), 7.80 (m, 2H), 7.65 (m, 1H), 7.40 (m, 2H), 6.98 (m, 3H), 6.35-6.75 (m, 2H), 6.23 (m, 1H), 5.71 (m, 1H), 3.58 (m, 4H), 3.20 (m, 4H), 2.30 (s, 3H).

Example 38: Preparation of N-(3-((6-(4-(2-thio-6-azaspiro[3.3]heptan-6-yl)phenyl)-7H-pyrrolo[2,3-d]pyrimidin-4-yl)oxy)phenyl)acrylamide

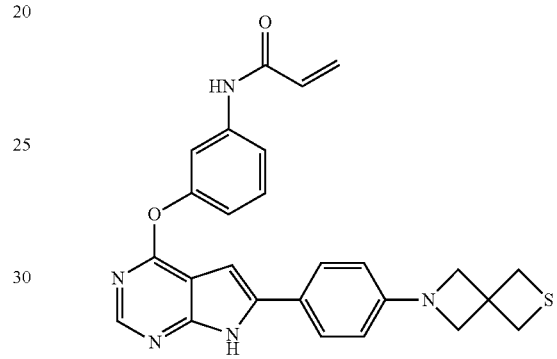

The preparation method was the same as that of Example 37, except that 6-methyl-2,6-diazaspiro[3.3]heptane oxalate was replaced by 2-thio-6-azaspiro[3.3]heptane oxalate to give the title compound.

MS: m/z=470.2 [M+H]$^+$.

$^1$H NMR (300 MHz, DMSO): δ 12.59 (s, 1H), 10.33 (s, 1H), 8.22 (s, 1H), 7.80 (m, 2H), 7.64 (m, 1H), 7.38 (m, 2H), 7.05 (m, 3H), 6.40 (m, 2H), 6.23 (m, 1H), 5.68 (m, 1H), 3.61 (m, 4H), 3.10 (m, 4H).

Example 39: Preparation of N-(3-((6-(4-(4-acetylpiperazin-1-yl)phenyl)-7H-pyrrolo[2,3-d]pyrimidin-4-yl)oxy)phenyl) acrylamide

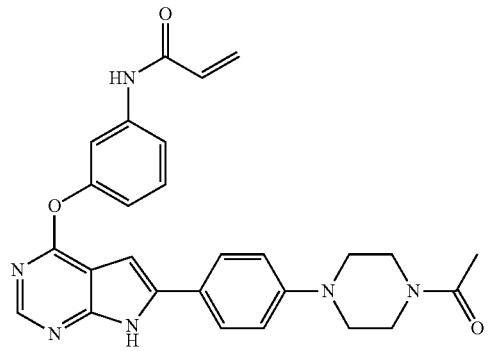 [SMILES: C=CC(=O)Nc1cccc(Oc2ncnc3[nH]c(-c4ccc(N5CCN(C(C)=O)CC5)cc4)cc23)c1]

The preparation method was the same as that of Example 12, except that (4-(4-methylpiperazin-1-yl)phenyl)boronic acid was replaced by 4-(4-acetylpiperazinyl)phenylboronic acid pinacol ester to give the title compound.

MS: m/z=483.3 [M+H]+.

1H NMR (300 MHz, DMSO): δ 12.56 (s, 1H), 10.32 (s, 1H), 8.28 (m, 1H), 7.83 (m, 2 H), 7.70 (m, 1H), 7.41 (m, 1H), 7.35 (m, 1H), 7.00 (m, 3H), 6.85 (m, 1H), 6.43 (m, 1H), 6.25 (m, 1H), 5.77 (m, 1H), 3.59 (m, 4H), 3.22 (m, 4H), 2.05 (s, 3H).

Example 40: Preparation of N-(3-((6-(4-(2,4-dimethylpiperazin-1-yl)phenyl)-7H-pyrrolo[2,3-d]pyrimidin-4-yl)oxy)phenyl)acrylamide

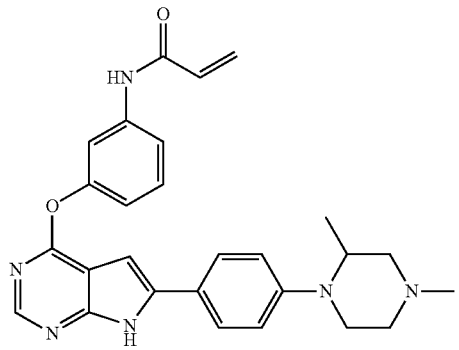 [SMILES: C=CC(=O)Nc1cccc(Oc2ncnc3[nH]c(-c4ccc(N5CCN(C)CC5C)cc4)cc23)c1]

The preparation method was the same as that of Example 12, except that (4-(4-methylpiperazin-1-yl)phenyl)boronic acid was replaced by (4-(2,4-dimethylpiperazin-1-yl)phenyl)boronic acid to give the title compound.

MS: m/z=469.4 [M+H]+.

1H NMR (300 MHz, DMSO): δ 12.59 (s, 1H), 10.38 (s, 1H), 8.26 (s, 1H), 7.82 (m, 2H), 7.66 (m, 1H), 7.37 (m, 2H), 6.99 (m, 3H), 6.83 (m, 1H), 6.43 (m, 1H), 6.20 (m, 1H), 5.69 (m, 1H), 3.44-2.78 (m, 6H), 2.32 (m, 1H), 2.29 (m, 3H), 1.21 (m, 3H).

Example 41: Preparation of 1-(4-(4-(3-acrylamidophenoxy)-7H-pyrrolo[2,3-d]pyrimidin-6-yl)phenyl)-4-methylpiperazin-2-carboxylate acid

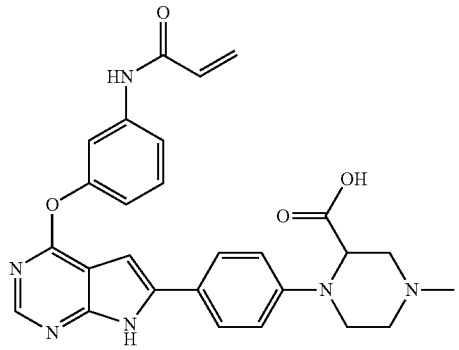 [SMILES: C=CC(=O)Nc1cccc(Oc2ncnc3[nH]c(-c4ccc(N5CCN(C)CC5C(=O)O)cc4)cc23)c1]

The preparation method was the same as that of Example 37, except that 6-methyl-2,6-diazaspiro[3.3]heptane oxalate was replaced by 4-methylpiperazin-2-carboxylic acid.

MS: m/z=499.4 [M+H]+.

1H NMR (300 MHz, DMSO): δ 12.50 (s, 1H), 10.31 (s, 1H), 8.28 (s, 1H), 7.82 (m, 2H), 7.65 (m, 1H), 7.31 (m, 2H), 7.01 (m, 3H), 6.85 (m, 1H), 6.44 (m, 1H), 6.20 (m, 1H), 5.65 (m, 1H), 4.32 (m, 1H), 3.50 (m, 2H), 3.18 (m, 4H), 2.33 (s, 3H).

Example 42: Preparation of N-(3-((6-(4-(4,4-difluoropiperidin-1-yl)phenyl)-7H-pyrrolo[2,3-d]pyrimidin-4-yl)oxy)phenyl) acrylamide

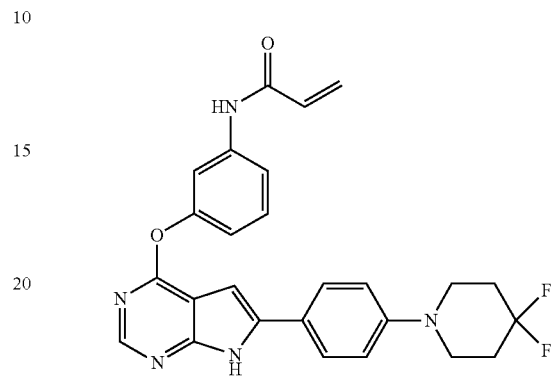

The preparation method was the same as that of Example 37, except that 6-methyl-2,6-diazaspiro[3.3]heptane oxalate was replaced by 4,4-difluoropiperidine to give the title compound.

MS: m/z=476.3 [M+H]+.

1H NMR (300 MHz, DMSO): δ 12.50 (s, 1H), 10.38 (s, 1H), 8.28 (s, 1H), 7.88 (m, 2H), 7.70 (m, 1H), 7.29 (m, 2H), 7.05 (m, 3H), 6.84 (m, 1H), 6.38 (m, 1H), 6.25 (m, 1H), 5.68 (m, 1H), 3.47 (m, 4H), 2.03 (m, 4H).

Example 43: Preparation of N-(3-((6-(4-(5-methylhexahydropyrrolo[3,4-c]pyrrol-2(1H)-yl)phenyl)-7H-pyrrolo[2,3-d]pyrimidin-4-yl)oxy)phenyl)acrylamide

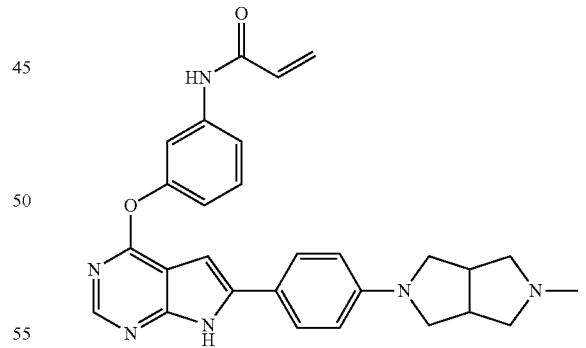

The preparation method was the same as that of Example 37, except that 6-methyl-2,6-diazaspiro[3.3]heptane oxalate was replaced by 2-methyloctahydropyrrolo[3,4-c]pyrrole to give the title compound.

MS: m/z=481.4 [M+H]+.

1H NMR (300 MHz, DMSO): δ 12.53 (s, 1H), 10.31 (s, 1H), 8.26 (s, 1H), 7.83 (m, 2H), 7.67 (m, 1H), 7.31 (m, 2H), 6.95 (m, 3H), 6.83 (m, 1H), 6.27 (m, 1H), 6.22 (m, 1H), 5.68 (m, 1H), 2.93-3.23 (m, 6H), 2.17-2.43 (m, 4H), 2.07 (m, 3H).

71

Example 44: Preparation of N-(3-((6-(4-((1,1-dioxothiomorpholinyl)methyl)phenyl)-7H-pyrrolo[2,3-d]pyrimidin-4-yl)oxy)phenyl)acrylamide

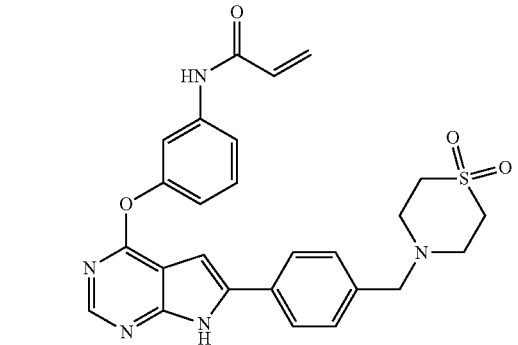

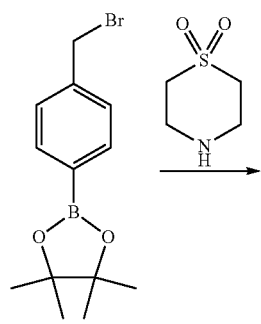

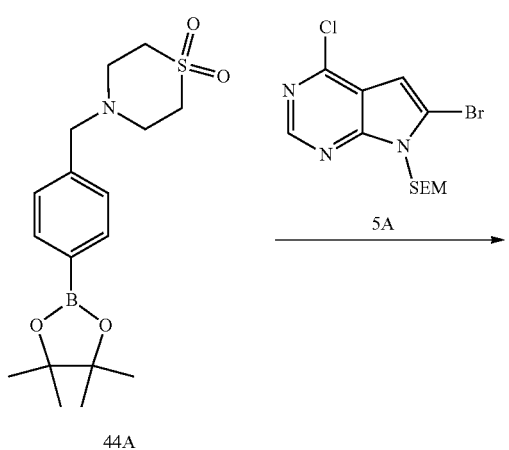

44B

72

-continued

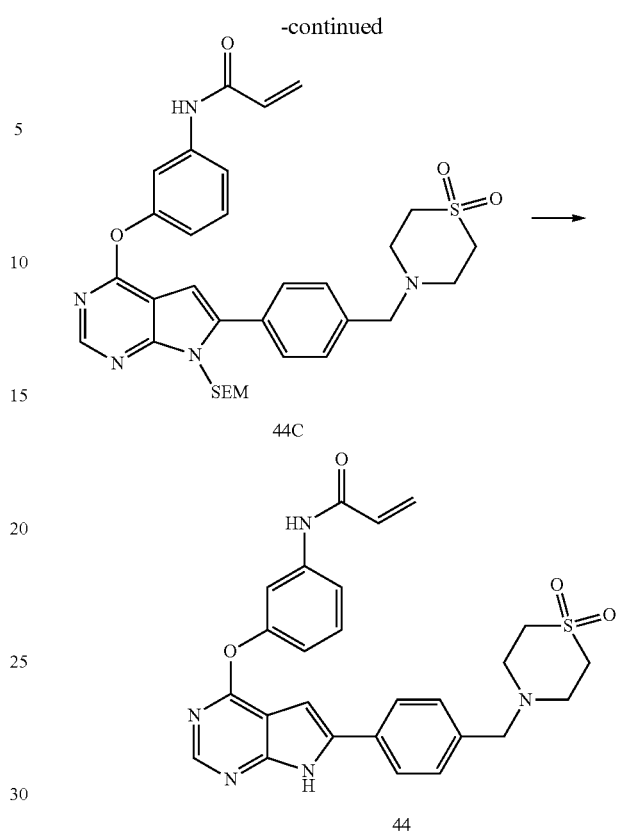

Step 1: Synthesis of (4-(1,1-dioxothiomorpholinyl)methyl)phenyl)boronic acid pinacol ester (Intermediate 44A)

4-Bromomethylbenzeneboronic acid pinacol ester (5.0 g, 1.68 mmol), 1,1-dioxide thiomorpholine 2.74 g (2.02 mmol), and potassium carbonate (2.79 g, 2.02 mmol) were added to a flask and added with DMF (25 mL). The mixture was stirred at 80° C. for 4 hours. The reaction mixture was cooled to rt., and poured into ice water (125 mL), and stirred for 30 min. The mixture was filtered to give 4.72 g of the title compound as white solid (yield of 79.7%).

Step 2: Synthesis of 4-(4-(4-chloro-7-((2-(trimethylsilyl)ethoxy)methyl)-7H-pyrrolo[2,3-d]pyrimidin-6-yl)benzyl)thiomorpholine-1,1-dioxide (intermediate 44B)

6-Bromo-4-chloro-7-((2-(trimethylsilyl)ethoxy)methyl)-7H-pyrrolo[2,3-d]pyrimidine (1.87 g, 5.16 mmol) was added to a 100 mL of flask, and added with (4-(1,1-dioxothiomorpholinyl)methyl)phenyl)boronic acid pinacol ester (1.64 g, 4.32 mmol), dioxane (20 mL), sodium carbonate (1.33 g, 12.55 mmol), water (4 mL), and Pd(dppf)Cl$_2$ (0.22 g, 0.30 mmol). The reaction mixture was stirred at 80° C. overnight under argon atmosphere. After completion of the reaction, the reaction mixture was cooled to rt. and concentrated under reduced pressure to dryness. The residues were purified by column chromatography (eluent: EtOAc:PE-EtOAc) to give 1.05 g of the title compound as pale pink solid (yield of 40.2%).

Step 3: Synthesis of N-(3-((6-(4-((1,1-dioxothiomorpholinyl)methyl)phenyl)boronic acid pinacol-7-((2-(trimethylsilyl))ethoxy))methyl)-7H-pyrrolo[2,3-d]pyrimidin-4-yl)oxy)phenyl)acrylamide (Intermediate 44C)

4-(4-(4-Chloro-7-((2-(trimethylsilyl)ethoxy)methyl)-7H-pyrrolo[2,3-d]pyrimidin-6-yl)benzyl)thiomorpholine-1,1-dioxide (0.46 g, 0.9 mmol) N-(3-hydroxyphenyl)acrylamide (0.32 g, 2.0 mmol), potassium carbonate (0.40 g, 2.9 mmol), DMF (10 mL) was added to a single neck flask. The reaction mixture was stirred at 100° C. for 4 h, and then cooled to rt. and concentrated under reduced pressure. The residues were purified by column chromatography (eluent: DCM:MeOH, 40:1) to give 0.46 g of the title compound as yellow solid (yield of 80.1%).

Step 4: Synthesis of N-(3-((6-(4-((1,1-dioxothiomorpholinyl)methyl)phenyl)-7H-pyrrolo[2,3-d]pyrimidin-4-yl)oxy)phenyl)acrylamide (compound 44)

N-(3-((6-(4-((1,1-dioxothiomorpholinyl)methyl)phenyl)-7-((2-(trimethylsilyl))ethoxy))methyl)-7H-pyrrolo[2,3-d]pyrimidin-4-yl)oxy)phenyl)acrylamide (0.46 g, 0.7 mmol) was added to a 50 mL of flask and added with DCM (5 mL) and TFA (5 mL). The reaction mixture was stirred at rt. overnight. The reaction mixture was concentrated under reduced pressure to dryness. The residues were added with methanol (20 mL) and aqueous ammonia (3 mL) and stirred at room temperature for 2 h. After completion of the reaction, the reaction mixture was added with saturated brine (10 mL), and extracted with DCM (20 mL). The organic layer was concentrated under reduced pressure. The residues were purified by column chromatography (eluent: DCM:MeOH, 10:1) to give 110 mg of the title compound as pale yellow solid (yield of 30.1%, purity of 95.3%).

MS: m/z=504.9 [M+H]$^+$.

$^1$H NMR (300 MHz, DMSO): δ 12.73 (s, 1H), 10.32 (s, 1H), 8.33 (m, 1H), 7.94 (m, 2H), 7.71 (m, 1H), 7.44 (m, 4H), 7.02 (m, 2H), 6.29 (m, 1H), 6.23 (m, 1H), 5.79 (m, 1H), 3.72 (m, 2H), 3.14 (m, 4H), 2.90 (m, 4H).

Example 45: Preparation of N-(3-((6-(4-((1,1-dioxothiomorpholinyl)methyl)phenyl)-7H-pyrrolo[2,3-d]pyrimidin-4-yl)amino)phenyl)acrylamide

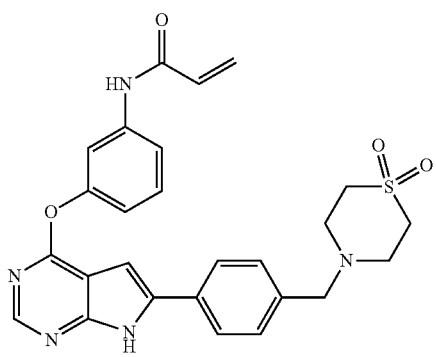 [SMILES: C=CC(=O)Nc1cccc(Oc2ncnc3[nH]c(-c4ccc(CN5CCS(=O)(=O)CC5)cc4)cc23)c1]

The preparation method was the same as that of Example 5, except that (4-(4-methylpiperazin-1-yl)phenyl) boric acid was replaced by (4-(1,1-dioxothiomorpholinyl)methyl)phenyl)boronic acid pinacol ester (intermediate 44A) to give the title compound.

MS: m/z=503.9 [M+H]$^+$.

$^1$H NMR (300 MHz, DMSO): δ 12.27 (s, 1H), 10.17 (s, 1H), 9.45 (s, 1H), 8.29 (m, 2H), 7.81 (m, 2H), 7.67 (m, 1H), 7.44 (m, 2H), 7.31 (m, 3H), 6.50 (m, 1H), 6.28 (m, 1 H), 5.76 (m, 1H), 3.71 (m, 2H), 3.13 (m, 4H), 2.91 (m, 4H).

Example 46: Preparation of N-(3-((6-(4-(morpholinomethyl)phenyl)-7H-pyrrolo[2,3-d]pyrimidin-4-yl)oxy)phenyl)acrylamide

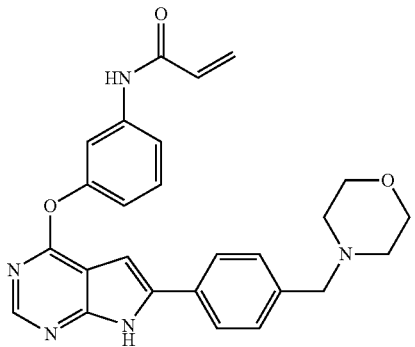 [SMILES: C=CC(=O)Nc1cccc(Oc2ncnc3[nH]c(-c4ccc(CN5CCCCC5)cc4)cc23)c1]

The preparation method was the same as that of Example 44, except that thiomorpholine-1,1-dioxide was replaced by morpholine to give the title compound.

MS: m/z=455.0 [M+H]$^+$.

$^1$H NMR (300 MHz, DMSO): δ 12.79 (s, 1H), 10.77 (s, 1H), 8.32 (m, 1H), 7.97 (m, 2H), 7.76 (m, 1H), 7.60 (m, 2H), 7.40 (m, 2H), 7.00 (m, 2H), 6.57 (m, 1H), 6.25 (m, 1H), 5.75 (m, 1H), 3.35 (s, 2H), 2.45 (m, 4H), 1.96 (m, 4H).

Example 47: Preparation of N-(3-((6-(4-((4,4-Difluoropiperidin-1-yl)methyl)phenyl)-7H-pyrrolo[2,3-d]pyrimidin-4-yl)oxy)phenyl)acrylamide

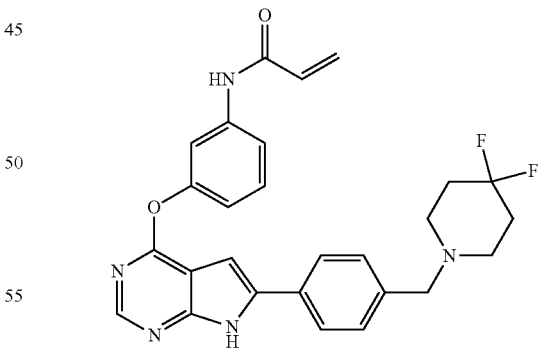

The preparation method was the same as that of Example 44, except that thiomorpholine-1,1-dioxide was replaced by 4,4-difluoropiperidine to give the title compound.

MS: m/z=490.3 [M+H]$^+$.

$^1$H NMR (300 MHz, DMSO): δ 12.72 (s, 1H), 10.31 (s, 1H), 8.33 (m, 1H), 7.93 (m, 2H), 7.71 (m, 1H), 7.49 (m, 1H), 7.42 (m, 3H), 7.04 (m, 2H), 6.43 (m, 1H), 6.29 (m, 1H), 5.78 (m, 1H), 3.59 (s, 2H), 2.49 (m, 4H), 1.97 (m, 4H).

Example 48: Preparation of N-(3-((6-(4-(piperidin-1-ylmethyl)phenyl)-7H-pyrrolo[2,3-d]pyrimidin-4-yl)oxy)phenyl)acrylamide

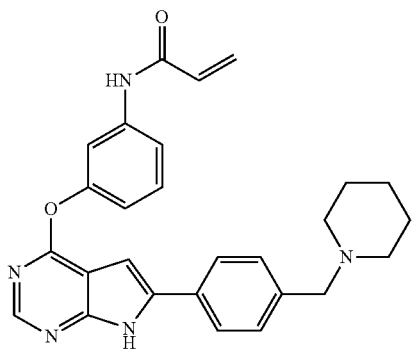

The preparation method was the same as that of Example 44, except that thiomorpholine-1,1-dioxide was replaced by piperidine to give the title compound.

MS: m/z=454.5 [M+H]⁺.

¹H NMR (300 MHz, DMSO): δ 12.52 (s, 1H), 10.33 (s, 1H), 8.33 (m, 1H), 7.94 (m, 2H), 7.72 (m, 1H), 7.50 (m, 1H), 7.42 (m, 3H), 7.05 (m, 1H), 7.00 (m, 1H), 6.43 (m, 1H), 6.26 (m, 1H), 5.76 (m, 1H), 3.60 (s, 2H), 2.50 (m, 4H), 1.55 (m, 4H), 1.43 (m, 2H).

Example 49: Preparation of N-(3-((6-(4-(Pyrrolidin-1-ylmethyl)phenyl)-7H-pyrrolo[2,3-d]pyrimidin-4-yl)oxy)phenyl)acrylamide

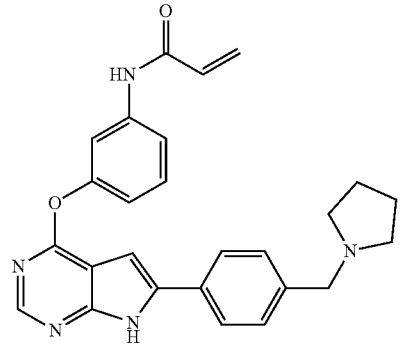 [SMILES: C=CC(=O)Nc1cccc(Oc2ncnc3[nH]c(-c4ccc(CN5CCCC5)cc4)cc23)c1]

The preparation method was the same as that of Example 44, except that thiomorpholine-1,1-dioxide was replaced by pyrrolidine to give the title compound.

MS: m/z=454.5 [M+H]⁺.

¹H NMR (300 MHz, DMSO): δ 12.52 (s, 1H), 10.33 (s, 1H), 8.33 (m, 1H), 7.94 (m, 2H), 7.72 (m, 1H), 7.50 (m, 1H), 7.42 (m, 3H), 7.05 (m, 1H), 7.00 (m, 1H), 6.43 (m, 1H), 6.26 (m, 1H), 5.76 (m, 1H), 3.60 (s, 2H), 2.50 (m, 4H), 1.55 (m, 4H), 1.43 (m, 2H).

Example 50: Preparation of N-(3-((6-(4-(4-6-methyl-2,6-diazaspiro[3.3]heptan-2-yl)methyl)phenyl)-7H-pyrrolo[2,3-d]pyrimidin-4-yl)oxy)phenyl)acrylamide

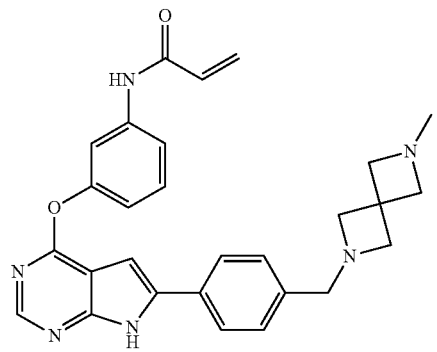 [SMILES: C=CC(=O)Nc1cccc(Oc2ncnc3[nH]c(-c4ccc(CN5CC6(CN(C)C6)C5)cc4)cc23)c1]

The preparation method was the same as that of Example 44, except that thiomorpholine-1,1-dioxide was replaced by 2-methyl-2,6-diazaspiro[3.3]heptane oxalate to give the title compound.

MS: m/z=481.5 [M+H]⁺.

¹H NMR (300 MHz, DMSO): δ 12.70 (s, 1H), 10.52 (s, 1H), 8.28 (s, 1H), 7.88 (m, 2H), 7.70 (m, 1H), 7.48 (m, 2H), 7.00-7.33 (m, 3H), 6.85 (m, 1H), 6.49 (m, 1H), 6.30 (m, 1H), 5.76 (m, 1H), 3.46 (m, 2H), 3.40-3.25 (m, 8H), 2.25 (s, 3H).

Example 51: Preparation of N-(3-((6-(4-((5-methyl-hexahydropyrrolo[3,4-c]pyrrol-2(1H)-yl)methyl)phenyl)-7H-pyrrolo[2,3-d]pyrimidin-4-yl)oxy)phenyl)acrylamide

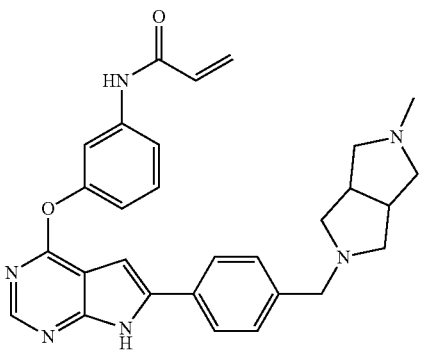 [SMILES: C=CC(=O)Nc1cccc(Oc2ncnc3[nH]c(-c4ccc(CN5CC6CN(C)CC6C5)cc4)cc23)c1]

The preparation method was the same as that of Example 44, except that thiomorpholine-1,1-dioxide was replaced by 2-methyloctahydropyrrolo[3,4-c]pyrrole to give the title compound.

MS: m/z=495.4 [M+H]⁺.

¹H NMR (300 MHz, DMSO): δ 12.68 (s, 1H), 10.37 (s, 1H), 8.31 (s, 1H), 7.79 (m, 2H), 7.71 (m, 1H), 7.58 (m, 2H), 7.42 (m, 2H), 6.91 (m, 2H), 6.51 (m, 1H), 6.27 (m, 1H), 5.78 (m, 1H), 3.39 (m, 2H), 3.19 (m, 2H), 2.56 (m, 4H), 2.19 (m, 4H), 2.08 (s, 3H).

Example 52: Preparation of N-(3-((6-(4-(3-methyl-3,8-diazabicyclo[3.2.1]octane-8-yl)methyl)phenyl)-7H-pyrrolo[2,3-d]pyrimidin-4-yl)oxy)phenyl)acrylamide

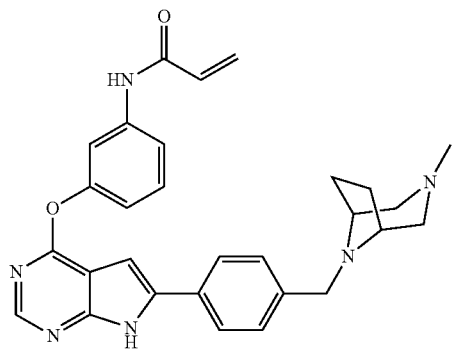 [SMILES: C=CC(=O)Nc1cccc(Oc2ncnc3[nH]c(-c4ccc(CN5C6CCC5CN(C)C6)cc4)cc23)c1]

The preparation method was the same as that of Example 44, except that thiomorpholine-1,1-dioxide was replaced by 3-methyl-3,8-diazabicyclo[3.2.1]octane dihydrochloride to give the title compound.

MS: m/z=495.3 [M+H]$^+$.

$^1$H NMR (300 MHz, DMSO): δ 12.71 (s, 1H), 10.31 (s, 1H), 8.27 (s, 1H), 7.80 (m, 2H), 7.69 (m, 1H), 7.60 (m, 2H), 7.40 (m, 2H), 6.99 (m, 2H), 6.53 (m, 1H), 6.31 (m, 1H), 5.76 (m, 1H), 3.66 (m, 2H), 2.89 (m, 2H), 2.52 (m, 2H), 2.27 (m, 2H), 2.20 (m, 5H), 1.45-1.66 (m, 4H).

Example 53: Preparation of N-(3-((6-(4-((1-methylpiperidin-4-yl)amino)phenyl)-7H-pyrrolo[2,3-d]pyrimidin-4-yl)oxy)phenyl)acrylamide

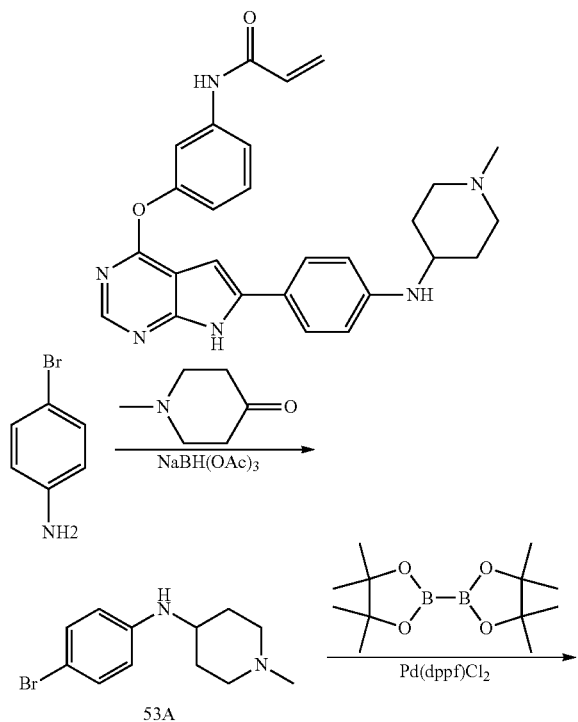

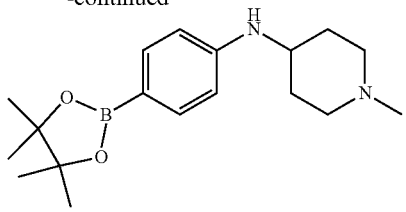

53B

Step 1: Synthesis of N-(4-bromophenyl)-1-methylpiperidin-4-amine (Intermediate 53A)

4-Bromoaniline (4.30 g, 25 mmol) and 1-methylpiperidin-4-one (2.83 g, 25 mmol) were dissolved in 100 mL anhydrous tetrahydrofuran and stirred at room temperature for 2 h. Then, sodium triacetoxyborohydride (10.6 g, 50 mmol) was added and the mixture was refluxed for 20 hours. The reaction mixture was cooled to rt. and filtered. The filtrate was concentrated under reduced pressure. The residues were purified by column chromatography (eluent: DCM:MeOH, 30:1 to 10:1) to give 4.28 g of the title compound as white solid (yield of 64.0%).

Step 2: Synthesis of (4-((1-methylpiperidin-4-yl)amino)phenyl)boronic acid pinacol ester (Intermediate 54B)

N-(4-bromophenyl)-1-methylpiperidin-4-amine (3.0 g, 11.2 mmol), biborate pinacol ester (4.24 g, 16.7 mmol), potassium acetate (2.19 g, 22.3 mmol), and Pd(dppf)Cl$_2$ (0.81 g, 1.1 mmol) were added to 80 mL of dioxane successively. The reaction mixture was stirred at 100° C. for 20 h under nitrogen atmosphere. The reaction mixture was cooled to rt. and concentrated to dryness under reduced pressure. The residues were purified by column chromatography (eluent: DCM:MeOH, 30:1 to 10:1) to give 1.66 g of the title compound as brown oil (yield of 47.0%).

The following steps were the same as steps 2, 3, and 4 of Example 12, except that (4-(4-methylpiperazin-1-yl)phenyl)boric acid was replaced by (4-((1-methylpiperidin-4-yl)amino)phenyl)boronic acid pinacol ester (intermediate 54B) to give the title compound.

MS: m/z=469.4[M+H]$^+$.

$^1$H NMR (600 MHz, DMSO): δ 12.36 (s, 1H), 10.26 (s, 1H), 8.21 (m, 1H), 7.81 (m, 3H), 7.45 (m, 1H), 7.36 (m, 1H), 6.97 (m, 1H), 6.64 (m, 3H), 6.39 (m, 1H), 6.21 (m, 1H), 5.75 (m, 2H), 3.23 (m, 1H), 2.78 (m, 2H), 2.17 (s, 3H), 2.06 (m, 2H), 1.87 (m, 2H), 1.40 (m, 2H).

Example 54: Preparation of N-(3-((6-(4-(morpholin-4-formyl)phenyl)-7H-pyrrolo[2,3-d]pyrimidin-4-yl)oxy)phenyl)acrylamide

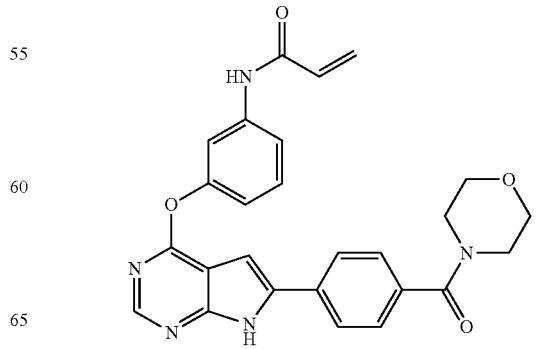

The preparation method was the same as that of Example 35, except that 4-(4-bromophenyl)thiomorpholine-1,1-dioxide was replaced by (4-bromophenyl)(morpholinyl)ketone (prepared according to Tetrahedron, 2010, 66, 1472) to give the title compound.

MS: m/z=470.4 [M+H]⁺.

¹H NMR (300 MHz, DMSO): δ 12.50 (s, 1H), 10.40 (s, 1H), 8.31 (s, 1H), 7.80 (m, 2H), 7.60 (m, 1H), 7.40 (m, 2H), 7.00 (m, 3H), 6.81 (m, 1H), 6.36 (m, 1H), 6.23 (m, 1H), 5.69 (m, 1H), 3.75-3.50 (m, 8H).

Example 55: Preparation of N-(3-((6-(4-((1-methylpiperidin-4-yl)oxy)phenyl)-7H-pyrrolo[2,3-d]pyrimidin-4-yl)oxy)phenyl)acrylamide

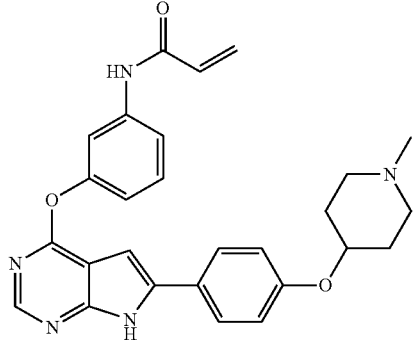 [SMILES: C=CC(=O)Nc1cccc(Oc2ncnc3[nH]c(-c4ccc(OC5CCN(C)CC5)cc4)cc23)c1]

The preparation method was the same as that of Example 35, except that 4-(4-bromophenyl)thiomorpholine-1,1-dioxide was replaced by 4-(4-bromophenoxy)-1-methylpiperidine (prepared according to WO 2011123946) to give the title compound.

MS: m/z=470.3 [M+H]⁺.

¹H NMR (300 MHz, DMSO): δ 12.66 (s, 1H), 10.29 (s, 1H), 8.29 (m, 1H), 7.89 (m, 2H), 7.71 (m, 1H), 7.33 (m, 4H), 6.98 (m, 2H), 6.39 (m, 1H), 6.22 (m, 1H), 5.69 (m, 1H), 4.10 (m, 1H), 2.75 (m, 2H), 2.40 (m, 2H), 2.11 (m, 2H), 1.95 (m, 2H).

Example 56: Preparation of N-(3-((6-(4-(methyl(1-methylpiperidin-4-yl)amino)phenyl)-7H-pyrrolo[2,3-d]pyrimidin-4-yl)oxy)phenyl)acrylamide

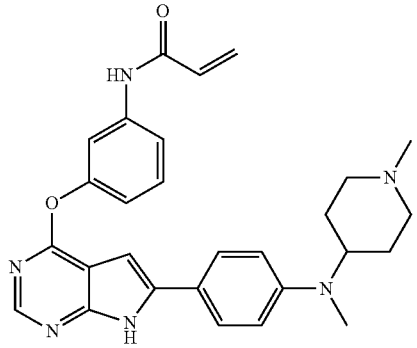 [SMILES: C=CC(=O)Nc1cccc(Oc2ncnc3[nH]c(-c4ccc(N(C)C5CCN(C)CC5)cc4)cc23)c1]

The preparation method was the same as that of Example 54, except that 4-bromoaniline was replaced by 4-bromo-N-methylaniline to give the title compound.

MS: m/z=483.5 [M+H]⁺.

¹H NMR (300 MHz, DMSO): δ 12.38 (s, 1H), 10.20 (s, 1H), 8.29 (m, 1H), 7.85 (m, 2H), 7.69 (m, 1H), 7.40 (m, 2H), 7.19 (m, 3H), 6.81 (m, 1H), 6.49 (m, 1H), 6.25 (m, 1H), 5.73 (m, 1H), 3.61 (m, 1H), 2.85 (s, 3H), 2.77-2.38 (m, 4H), 2.28 (s, 3H), 2.03-1.81 (m, 4H).

Example 57: Preparation of N-(3-((6-(4-((4-methylpiperazin-1-yl)sulfonyl)phenyl)-7H-pyrrolo[2,3-d]pyrimidin-4-yl)oxy)phenyl)acrylamide

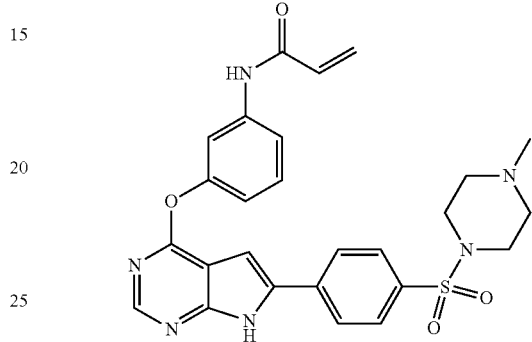

The preparation method was the same as that of Example 35, except that 4-(4-bromophenyl)thiomorpholine-1,1-dioxide was replaced by 1-((4-bromophenyl)sulfonyl)-4-methylpiperazine to give the title compound.

MS: m/z=519.2 [M+H]⁺.

¹H NMR (300 MHz, DMSO): δ 12.51 (s, 1H), 10.38 (s, 1H), 8.29 (s, 1H), 7.87 (m, 2H), 7.67 (m, 1H), 7.48 (m, 2H), 7.09 (m, 3H), 6.88 (m, 1H), 6.53 (m, 1H), 6.28 (m, 1H), 5.71 (m, 1H), 3.28 (m, 4H), 2.51 (m, 4H).

Example 58: Preparation of N-(3-((6-(4-((1-methylpiperidin-4-yl)oxy)methyl)phenyl)-7H-pyrrolo[2,3-d]pyrimidin-4-yl)oxy)phenyl)acrylamide

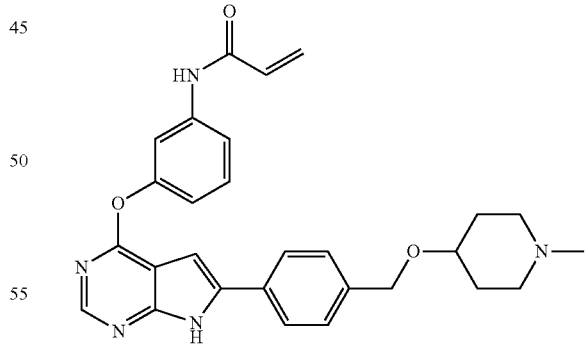

The preparation method was the same as that of Example 44, except that thiomorpholine-1,1-dioxide was replaced by 1-methyl-piperidin-4-ol to give the title compound.

MS: m/z=484.4 [M+H]⁺.

¹H NMR (300 MHz, DMSO): δ 12.69 (s, 1H), 10.50 (s, 1H), 8.33 (s, 1H), 7.81 (m, 2H), 7.60 (m, 1H), 7.51 (m, 2H), 6.99 (m, 3H), 6.82 (m, 1H), 6.55 (m, 1H), 6.27 (m, 1H), 5.66 (m, 1H), 4.80 (s, 2H), 3.89 (m, 1H), 2.58 (m, 4H), 2.26 (s, 3H), 1.88 (m, 4H).

Example 59: Preparation of N-(3-((6-(4-(((1-methylpiperidin-4-yl)amino)methyl)phenyl))-7H-pyrrolo[2,3-d]pyrimidin-4-yl)oxy)phenyl)acrylamide

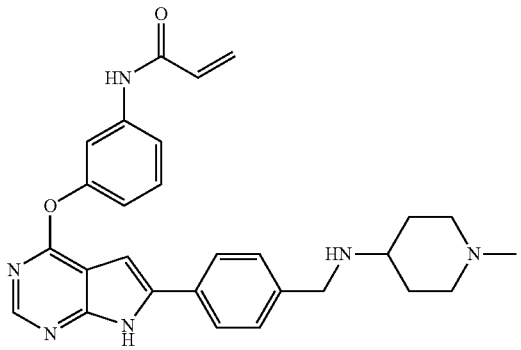 [SMILES: C=CC(=O)Nc1cccc(Oc2ncnc3[nH]c(-c4ccc(CNC5CCN(C)CC5)cc4)cc23)c1]

The preparation method was the same as that of Example 44, except that thiomorpholine-1,1-dioxide was replaced by 1-methylpiperidin-4-amine to give the title compound.

MS: m/z=483.3 [M+H]+.

1H NMR (300 MHz, DMSO): δ 12.71 (s, 1H), 10.39 (s, 1H), 8.28 (s, 1H), 7.79 (m, 2H), 7.57 (m, 1H), 7.51 (m, 2H), 6.99 (m, 3H), 6.83 (m, 1H), 6.57 (m, 1H), 6.29 (m, 1H), 5.73 (m, 1H), 3.98 (s, 2H), 2.78 (m, 1H), 2.55 (m, 4H), 2.28 (s, 3H), 1.88 (m, 2H), 1.49 (m, 2H).

Example 60: Preparation of N-(3-((6-(4-((methyl(1-methylpiperidin-4-yl)amino)methyl))phenyl)-7H-pyrrolo[2,3-d]pyrimidin-4-yl)oxy)phenyl) acrylamide

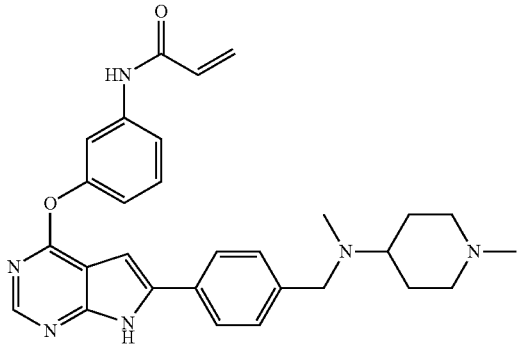 [SMILES: C=CC(=O)Nc1cccc(Oc2ncnc3[nH]c(-c4ccc(CN(C)C5CCN(C)CC5)cc4)cc23)c1]

The preparation method was the same as that of Example 12, except that morpholine-1,1-dioxide was replaced by N,1-dimethylpiperidin-4-amine to give the title compound.

MS: m/z=497.3 [M+H]+.

1H NMR (300 MHz, DMSO): δ 12.70 (s, 1H), 10.69 (s, 1H), 8.35 (m, 1H), 7.90 (m, 2H), 7.73 (m, 1H), 7.55 (m, 2H), 7.39 (m, 2H), 7.00 (m, 2H), 6.57 (m, 1H), 6.25 (m, 1H), 5.75 (m, 1H), 4.07 (m, 1H), 3.69 (m, 1H), 2.57 (m, 4H), 2.40 (m, 1H), 2.32 (s, 3H), 2.26 (s, 3H), 1.95 (m, 2H), 1.55 (m, 2H).

Example 61: Preparation of N-(4-(4-(3-acrylamidophenoxy)-7H-pyrrolo[2,3-d]pyrimidin-6-yl)phenyl)-1-methylpiperidin-4-yl-carboxamide

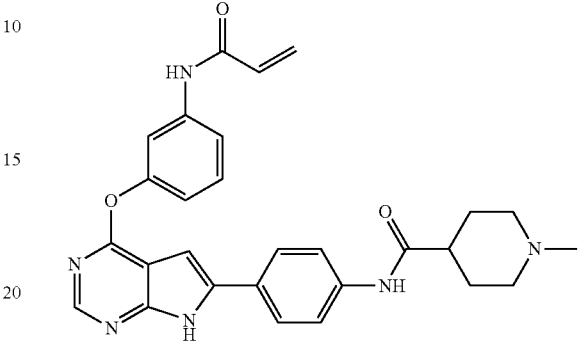

The preparation method was the same as that of Example 35, except that 4-(4-bromophenyl)thiomorpholine-1,1-dioxide was replaced by N-(4-bromophenyl)-1-methylpiperidine-4-carboxamide (prepared according to WO 2010054279) to give the title compound.

MS: m/z=496.4 [M+H]+.

1H NMR (300 MHz, DMSO): δ 12.55 (s, 1H), 10.41 (s, 1H), 9.38 (s, 1H), 8.33 (s, 1H), 7.87 (m, 2H), 7.69 (m, 1H), 7.48 (m, 2H), 7.19 (m, 3H), 6.85 (m, 1H), 6.53 (m, 1H), 6.27 (m, 1H), 5.67 (m, 1H), 2.75-2.40 (m, 5H), 2.33 (m, 2H), 1.73 (m, 2H).

Example 62: Preparation of N-(3-((6-(4-(4-(ethylsulfonyl)piperazin-1-yl)phenyl)-7H-pyrrolo[2,3-d]pyrimidin-4-yl)oxy)phenyl)acrylamide

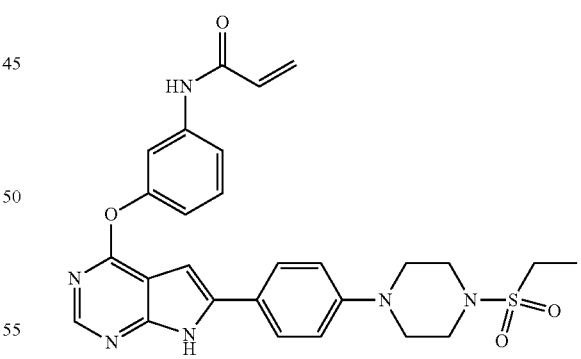

The preparation method was the same as that of Example 35, except that 4-(4-bromophenyl)thiomorpholine-1,1-dioxide was replaced by 1-(4-bromophenyl)-4-(ethylsulfonyl)piperazine to give the title compound.

MS: m/z=533.2 [M+H]+.

1H NMR (600 MHz, DMSO): δ 12.55 (s, 1H), 10.38 (s, 1H), 8.25 (m, 1H), 7.81 (m, 2H), 7.49 (m, 3H), 6.96 (m, 4H), 6.47 (m, 2H), 6.21 (m, 1H), 5.73 (m, 1H), 3.35 (m, 8H), 3.08 (m, 2H), 1.21 (m, 3H).

Example 63: Preparation of N-(3-((6-(4-((4,4-difluoropiperidin-1-yl)methyl)phenyl)-7H-pyrrolo[2,3-d]pyrimidin-4-yl)oxy)phenyl)but-2-ynylamide

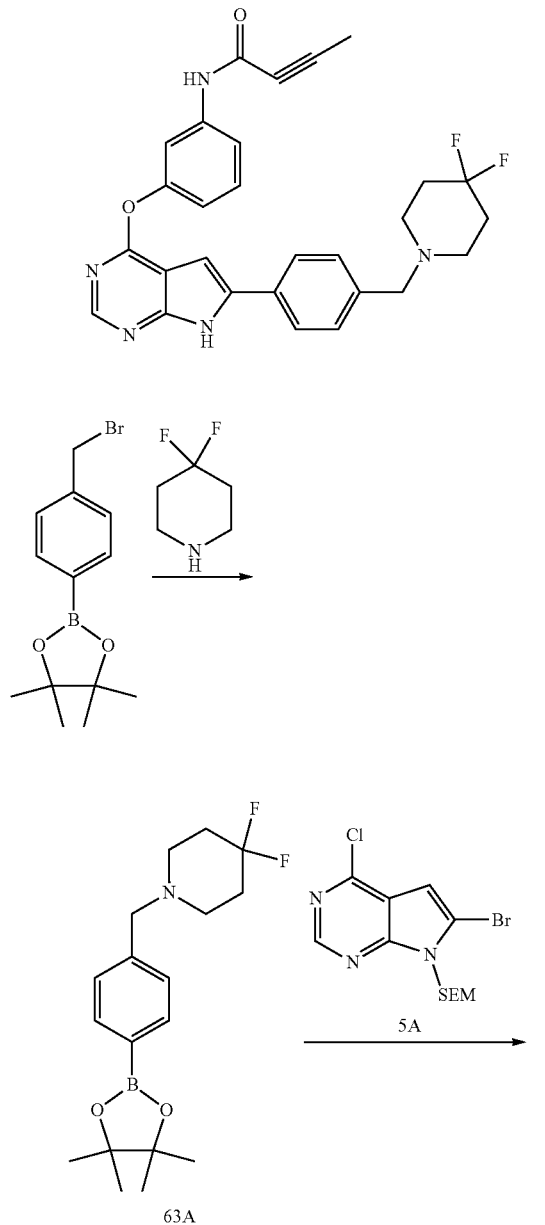

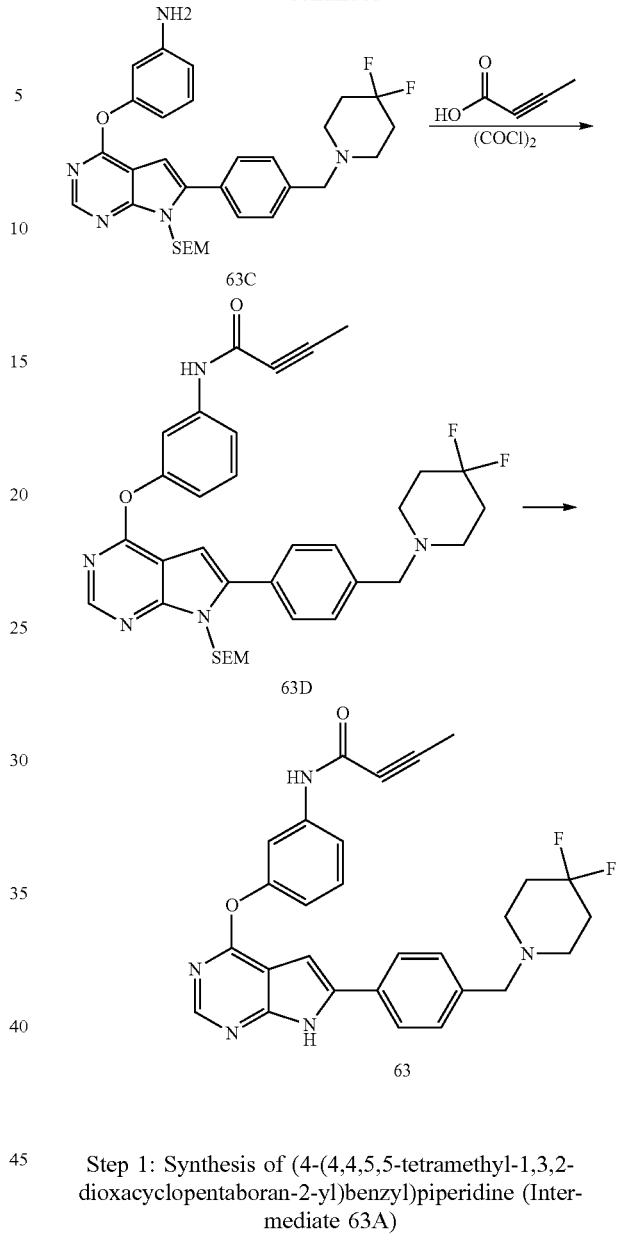

Step 1: Synthesis of (4-(4,4,5,5-tetramethyl-1,3,2-dioxacyclopentaboran-2-yl)benzyl)piperidine (Intermediate 63A)

4-Bromomethylbenzeneboronic acid pinacol ester (5.0 g, 1.68 mmol), 4,4-difluoropiperidine (2.44 g, 2.02 mmol) and K$_2$CO$_3$ (2.79 g, 2.02 mmol) were dissolved in DMF (25 mL) and was stirred at 80° C. for 4 hours. The reaction mixture was cooled to rt., and then poured into ice water (125 mL) and stirred for 30 min. The mixture was filtered to give 5.06 g of the title compound as white solid (yield of 88.8%).

Step 2: Synthesis of 4-chloro-6-(4-((4,4-difluoropiperidin-1-yl)methyl)phenyl)-7-((2-(trimethylsilyl)ethoxy)methyl)-7H-pyrrolo[2,3-d]pyrimidine (Intermediate 63B)

6-Bromo-4-chloro-7-((2-(trimethylsilyl)ethoxy)methyl)-7H-pyrrolo[2,3-d]pyrimidine (1.87 g, 5.16 mmol) was added to a 100 mL of flask and added with (4-(4,4,5,5-tetramethyl-1,3,2-dioxacyclopentaboran-2-yl)benzyl)piperidine (1.46 g, 4.32 mmol), dioxane (20 mL), sodium carbonate (1.33 g, 12.55 mmol), water 4 mL, and Pd(dppf)Cl$_2$ (0.22 g, 0.30 mmol) successively. The reaction mixture was stirred at 80° C. overnight under argon atmosphere. After completion of the reaction, the reaction mixture was cooled to rt. and concentrated to dryness under reduced pressure. The residues were purified by column chromatography (eluent: PE:EtOAc, 5:1) to give 1.22 g of the title compound as a pale yellow solid (yield of 47.9%).

Step 3: Synthesis of 3-((6-(4-((4,4-Difluoropiperi-din-1-yl)methyl)phenyl)-7-((2-(trimethylsilyl) ethoxy)methyl)-7H-pyrrolo[2,3-d]pyrimidin-4-yl) oxy)aniline (Intermediate 63C)

4-Chloro-6-(4-((4,4-difluoropiperidin-1-yl)methyl)phenyl)-7-((2-(trimethylsilyl)ethoxy)methyl)-7H-pyrrolo[2,3-d]pyrimidine (1.20 g, 2.44 mmol) was added to a 50 mL of flask and added with m-aminophenol (0.32 g, 2.93 mmol), potassium carbonate (0.67 g, 4.88 mmol) and DMF (15 mL). The reaction mixture was stirred at 100° C. overnight. After completion of the reaction, the reaction mixture was cooled to rt. and concentrated to dryness under reduced pressure. The residues were purified by column chromatography (eluent: PE:EtOAc, 1:2) to give 0.40 g of the title compound as pale yellow oil (yield of 29.0%, purity of 97.0%).

Step 4: Synthesis of N-(3-((6-(4-((4,4-difluoropiperidin-1-yl)methyl)phenyl)-7-((2-(trimethylsilyl)) ethoxy)methyl)-7H-pyrrolo[2,3d]pyrimidin-4-yl) oxy)phenyl)but-2-ynylamide (Intermediate 63D)

Preparation of but-2-ynonic acid chloride

2-Butynoic acid (1.0 g, 11.9 mmol) was added to a 50 mL of flask and added with THF (20 mL). The mixture was stirred at room temperature and added with oxalyl chloride (1.2 mL) dropwise. Then, the mixture was added three drops of DMF and stirred at rt. for 1 h. After completion of the reaction, the reaction mixture was concentrated under reduced pressure.

3-((6-(4-((4,4-Difluoropiperidin-1-yl)methyl)phenyl)-7-((2-(trimethylsilyl)ethoxy)methyl)-7H-pyrrolo[2,3-d]pyrimidin-4-yl)oxy)aniline (0.4 g, 1.22 mmol) was added to a 50 mL of reaction flask and added with sodium bicarbonate (0.12 g, 1.46 mmol), THF (20 mL), and water (4 mL). The mixture was stirred under ice bath and added with a solution of but-2-ynonic acid chloride prepared above in THF (10 mL) dropwise. After addition, the reaction mixture was stirred at rt. for 1 h. After completion of the reaction, the reaction mixture was quenched with a saturated aqueous solution of ammonium chloride (50 mL), and extracted with DCM (50 mL). The organic layer was dried over anhydrous Na$_2$SO$_4$, and filtered. The filtrate was concentrated under reduced pressure. The residues were purified by column chromatography (eluent: ethyl acetate:petroleum ether, 2:1)) to give 170 mg of the title compound as pale yellow oil (yield of 38.0%, purity of 96.4%).

Step 5: Synthesis of N-(3-((6-(4-((4,4-difluoropiperidin-1-yl)methyl)phenyl)-7H-pyrrolo[2,3-d]pyrimidin-4-yl)oxy)phenyl)but-2-ynylamide (compound 63)

N-(3-((6-(4-((4,4-difluoropiperidin-1-yl)methyl)phenyl)-7-((2-(trimethylsilyl))ethoxy)methyl)-7H-pyrrolo[2,3d]pyrimidin-4-yl)oxy)phenyl)but-2-ynylamide (170 mg, 0.27 mmol) was added to a 50 mL of flask, and added with DCM (2 mL) and TFA (2 mL). The reaction mixture was stirred at rt. overnight and then concentrated under reduced pressure. The residues were added with methanol (3 mL) and aqueous ammonia (1 mL) and stirred at rt. for 1 h. After the completion of the reaction, the mixture was filtered and the filter cake was washed with water (5 mL) and dried to give 20 mg the title product as pale yellow solid (yield: 14.8%, purity: 95.0%).

MS: m/z=502.2 [M+H]$^+$.

$^1$H NMR (300 MHz, DMSO): δ 12.40 (s, 1H), 9.81 (s, 1H), 8.20 (m, 1H), 7.93 (m, 2H), 7.70 (m, 1H), 7.47 (m, 1H), 7.40 (m, 3H), 7.00 (m, 2H), 3.49 (s, 2H), 2.40 (m, 4H), 2.19 (m, 3H), 1.97 (m, 4H).

Example 64: Preparation of N-(3-((6-(4-piperidin-1-ylmethyl)phenyl)-7H-pyrrolo[2,3-d]pyrimidin-4-yl) oxy)phenyl)but-2-ynylamide

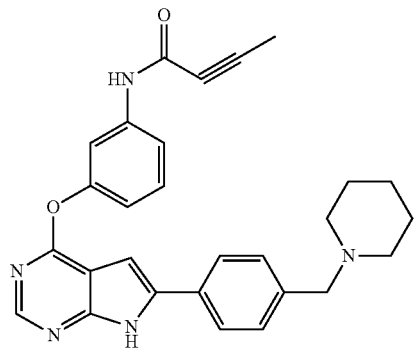 [SMILES: CC#CC(=O)Nc1cccc(Oc2ncnc3[nH]c(-c4ccc(CN5CCCCC5)cc4)cc23)c1]

The preparation method was the same as that of Example 63, except that 4,4-difluoropiperidine was replaced by piperidine to give the title compound.

MS: m/z=497.3 [M+H]$^+$.

1H NMR (300 MHz, DMSO): δ 12.43 (s, 1H), 9.81 (s, 1H), 8.15 (m, 1H), 7.93 (m, 2H), 7.71 (m, 1H), 7.49 (m, 1H), 7.43 (m, 3H), 7.02 (m, 2H), 3.48 (s, 2H), 2.37 (m, 4H), 2.19 (m, 3H), 1.57 (m, 4H), 1.43 (m, 2H).

Example 65: Preparation of N-(3-((6-(5-(4-methylpiperazin-1-yl)pyridin-2-yl)-7H-pyrrolo[2,3-d] pyrimidin-4-yl)oxy)phenyl)acrylamide

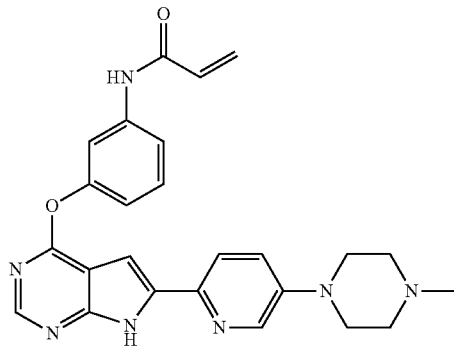 [SMILES: C=CC(=O)Nc1cccc(Oc2ncnc3[nH]c(-c4ccc(N5CCN(C)CC5)cn4)cc23)c1]

The preparation method was the same as that of Example 12, except that (4-(4-methylpiperazin-1-yl)phenyl)boronic acid was replaced by (5-(4-methylpiperazin-1-yl)pyridin-2-yl)boronic acid to give the title compound.

MS: m/z=456.5 [M+H]⁺.

$^1$H NMR (300 MHz, DMSO): δ 12.48 (s, 1H), 10.23 (s, 1H), 8.76 (m, 1H), 8.40 (m, 1H), 7.75 (m, 2H), 7.45 (m, 1H), 7.29 (m, 1H), 7.08 (m, 1H), 6.86 (m, 2H), 6.30 (m, 2H), 5.67 (m, 1H), 3.58 (m, 4H), 2.86 (m, 4H), 2.29 (s, 3H).

Example 66: Preparation of N-(3-((6-(5-((4,4-difluoropiperidin-1-yl)methyl)pyridine-2-yl)-7H-pyrrolo[2,3-d]pyrimidin-4-yl)oxy)phenyl)acrylamide

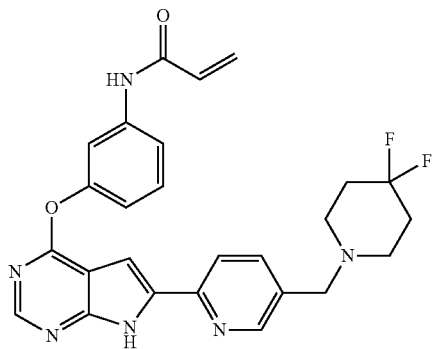 [SMILES: C=CC(=O)Nc1cccc(Oc2ncnc3[nH]c(-c4ccc(CN5CCC(F)(F)CC5)cn4)cc23)c1]

The preparation method was the same as that of Example 44, except that thiomorpholine-1,1-dioxide was replaced by 4,4-difluoropiperidine and 4-bromomethylbenzeneboronic acid pinacol ester was replaced by (5-(bromomethyl)pyridin-2-yl)boronic acid pinacol ester to give the title compound.

MS: m/z=491.3 [M+H]⁺.

$^1$H NMR (300 MHz, DMSO): δ 12.68 (s, 1H), 10.31 (s, 1H), 8.73 (m, 1H), 8.38 (m, 1H), 7.80 (m, 2H), 7.49 (m, 1H), 7.27 (m, 1H), 7.04 (m, 1H), 6.43 (m, 1H), 6.29 (m, 1H), 5.75 (m, 1H), 3.61 (s, 2H), 2.50 (m, 4H), 1.95 (m, 4H).

Example 67: Preparation of N-(3-((6-(2-fluoro-4-(4-methylpiperazin-1-yl)phenyl)-7H-pyrrolo[2,3-d]pyrimidin-4-yl)oxy)phenyl)acrylamide

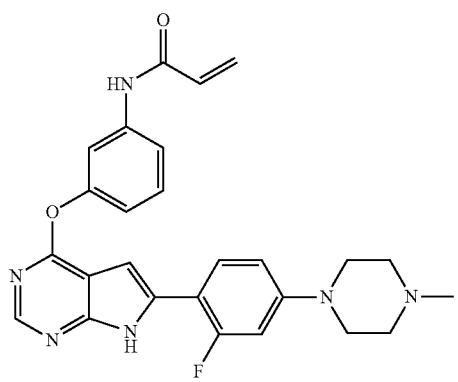 [SMILES: C=CC(=O)Nc1cccc(Oc2ncnc3[nH]c(-c4ccc(N5CCN(C)CC5)cc4F)cc23)c1]

The preparation method was the same as that of Example 12, except that (4-(4-methylpiperazin-1-yl)phenyl)boronic acid was replaced by (2-fluoro-4-(4-methylpiperazin-1-yl)phenyl)boronic acid pinacol ester to give the title compound.

MS: m/z=473.3 [M+H]⁺.

$^1$H NMR (300 MHz, DMSO): δ 12.47 (s, 1H), 10.43 (s, 1H), 8.26 (s, 1H), 7.83 (m, 1H), 7.66 (m, 2H), 7.41 (m, 2H), 6.95 (m, 2H), 6.80 (m, 1H), 6.40 (m, 1H), 6.27 (m, 1H), 5.70 (m, 1H), 3.34 (m, 4H), 2.90 (m, 4H), 2.27 (s, 3H).

Biological Evaluation of the Present Compounds

Test Example 1: Determination of BTK Inhibitory Activity

To a 384 reaction plate (6008280, PerkinElmer), 2 μL/well of BTK solution (purchased from Promega) was added. The test compound (10 mM stock solution) was diluted 100-fold to 100 μM with 100% DMSO. In a 384 dilution plate (3657, coming), a 1:3 dilution was made, and the gradient concentrations of the test compounds were 100, 33.3, 11.1, 3.7, 1.24, 0.41, 0.14, 0.046, 0.015, 0.0051, 0 μM. 2 μL of the test compound was transferred to a 384-dilution plate containing 38 μL of 1× Kinase Reaction Buffer, homogenized and centrifuged at 1000 rpm. 1 μL of the test compound was transferred to the 384 reaction plate, centrifuged at 1000 rpm, and incubated at 25° C. for 15 minutes. 2 μL of substrate mixture (ATP: 10 mM, 4 μL; Poly E4Y 1:1 mg/mL, 20 μL; Kinase Reaction Buffer: 776 μL) was transferred to a 384 reaction plate, centrifuged at 1000 rpm and incubated at 25° C. for 60 minutes. The final concentration of the test compound in the reaction system was the gradients of 1000, 333.3, 111.1, 37.03, 12.35, 4.14, 1.37, 0.46, 0.15, 0.051, 0 nM. The final concentration of DMSO was 1%. 5 μL of ADP-Glo solution (purchased from Promega) was transferred to a 384 reaction plate, centrifuged at 1000 rpm and incubated at 25° C. for 40 minutes. 10 μL of Detection solution was transferred to a 384 reaction plate, centrifuged at 1000 rpm and incubated for 40 minutes at 25° C. The RLU (Relative luminescence unit) signal was read using an Envision multi-function reader (Perkin Elmer), and the signal intensity was used to characterize the activity of BTK kinase. The IC$_{50}$ values was calculated and analyzed by Microsoft Excel software. The test results are shown in Table 1.

In Table 1, A means IC50<100 nM; B means IC$_{50}$=100 nM to 500 nM; C means IC$_{50}$=500 nM to 1,000 nM; and D means IC$_{50}$>1,000 nM.

TABLE 1

| BTK inhibitory activity | |
|---|---|
| Example | BTK inhibitory activity |
| 1 | A |
| 2 | A |
| 5 | A |
| 6 | A |
| 12 | A |
| 16 | A |
| 18 | A |
| 19 | A |
| 25 | A |
| 32 | A |
| 44 | A |
| 45 | A |
| 46 | A |
| 47 | A |
| 53 | A |
| 63 | A |
| 64 | A |

Conclusion: As shown in the table above, the compounds of the present invention all show excellent inhibitory activity on BTK.

Test Example 2: Type 2 Collagen Induced DBA/1J Mouse Arthritis Model (CIA)

The CIA model is an animal model widely used to study the drug activity on human rheumatoid arthritis.

Animals: DBA/1 mice, sex: male, number: 30, weight: 14-16 g, age of weeks: 6-7 weeks old, purchased from Beijing Weitong Lihua Experimental Animal Technology Co., Ltd., SPF, animal production license number: SCXK (Beijing) 2012-0001, the issue unit: Beijing Science and Technology Commission.

Group: model control group, administration (30 mg/Kg) group (compound of example 33).

An appropriate amount of Bovine Type II Collage (purchased from Chondrex. Inc.) was dissolved in 0.05 M acetic acid (4 mg collagen/mL) and stored in a refrigerator at 4° C. overnight. Then it was fully emulsified with an equal amount of complete Freund's adjuvant in an ice bath environment. Each DBA/1J mouse was injected subcutaneously at 1.5 cm from the base of the tail with 0.1 mL emulsion (200 μg of collagen). Clinical symptom observation and arthritis score were started 4 weeks after modeling. The scores of all symptomatic animals were ranked and randomly grouped into two groups, which were model control group (the same amount of 0.5% CMC was administered orally) and administration group (30 mg/kg of the compound of Example 33 was administered orally) respectively. The administration was continued for 21 days withonce a day. Arthritis scores and body weight changes were measured every 3 days after administration.

Arthritis Index Score: The arthritis index score is based on Wood's arthritis score as follows:
0 points: normal
1 points: redness involving 1 knuckle
2 points: redness involving more than 2 knuckles or mild redness involving entire foot
3 points: the feet are red and swollen
4 points: the feet are severely red and swollen, and the joints are stiff and inelastic.

The damage of each of the 4 paws was graded as 0-4 points and the total score of the limbs was calculated. The scores at different times were compared (arthritis index).

have a significant improving effect on arthritis symptoms in CIA mice.

What is claimed is:

1. A compound or a mesomer, racemate, enantiomer, diastereomer thereof or a pharmaceutically acceptable salt thereof, wherein the compound is N-(3-((6-(4-((4,4-difluoropiperidin-1-yl)methyl)phenyl)-7H-pyrrolo[2,3-d]pyrimidin-4-yl)oxy)phenyl)acrylamide

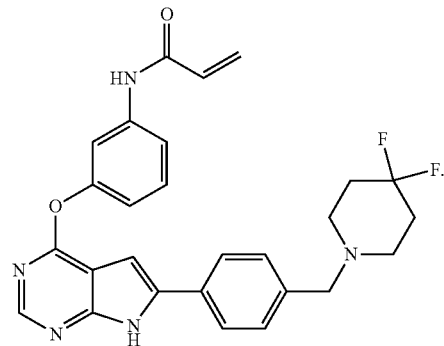 [SMILES: C=CC(=O)Nc1cccc(Oc2ncnc3[nH]c(-c4ccc(CN5CCC(F)(F)CC5)cc4)cc23)c1]

2. A pharmaceutical composition comprising the compound or a mesomer, racemate, enantiomer, diastereomer thereof or a pharmaceutically acceptable salt thereof according to claim 1, and a pharmaceutically acceptable carrier.

3. A method for inhibiting BTK kinase activity, comprising administering to a subject in need thereof an amount of the compound or a mesomer, racemate, enantiomer, diastereomer thereof or a pharmaceutically acceptable salt thereof according to claim 1 sufficient to inhibit BTK kinase activity in the subject.

4. The method according to claim 3, wherein the subject in need thereof has a disease selected from inflammation, autoimmune disease, or cancer.

5. A method for inhibiting BTK kinase activity, comprising administering to a subject in need thereof an amount of the composition of claim 2 sufficient to inhibit BTK kinase activity in the subject.

TABLE 2

Effect of the compound of Example 33 of the present invention on the arthritis score of CIA model animals

| | Arthritis score at different observation time points | | | | | | |
|---|---|---|---|---|---|---|---|
| Groups | Before administration | 3 day after administration | 7 day after administration | 10 day after administration | 14 day after administration | 17 day after administration | 21 day after administration |
| Model control (n = 9) | 4.11 ± 3.18 | 6.22 ± 5.02 | 6.89 ± 4.17 | 8.78 ± 4.41 | 9.33 ± 4.06 | 9.22 ± 4.71 | 8.33 ± 3.57 |
| BTK030 (n = 9) | 4.11 ± 3.26 | 5.00 ± 3.16 | 5.78 ± 2.91 | 6.13 ± 3.23 | 5.13 ± 3.60* | 4.63 ± 3.11* | 3.63 ± 1.92** |

Note:
Compared with model control group
*$P < 0.05$,
**$P < 0.01$

Conclusion: The compounds of the present invention significantly reduce the arthritic score of CIA model animals, indicating that the compounds of the present invention 6. The method according to claim 5, wherein the subject in need thereof has a disease selected from inflammation, autoimmune disease, or cancer.

7. The method according to claim 4, wherein the inflammation is arthritis, psoriatic arthritis, inflammatory bowel disease, or uveitis.

8. The method according to claim 4, wherein the autoimmune disease is multiple sclerosis, lupus, psoriasis, or sarcoidosis.

9. The method according to claim 4, wherein the cancer is breast cancer, cervical cancer, colon cancer, lung cancer, stomach cancer, rectal cancer, pancreatic cancer, brain cancer, skin cancer, oral cancer, prostate cancer, bone cancer, kidney cancer, ovarian cancer, bladder cancer, liver cancer, fallopian tube tumor, ovarian tumor, peritoneal tumor, melanoma, solid tumor, glioma, glioblastoma, hepatocellular carcinoma, mastoid renal tumor, head and neck tumor, leukemia, lymphoma, myeloma, or non-small cell lung cancer.

10. The method according to claim 6, wherein the inflammation is arthritis, psoriatic arthritis, inflammatory bowel disease, or uveitis.

11. The method according to claim 6, wherein the autoimmune disease is multiple sclerosis, lupus, psoriasis, or sarcoidosis.

12. The method according to claim 6, wherein the cancer is breast cancer, cervical cancer, colon cancer, lung cancer, stomach cancer, rectal cancer, pancreatic cancer, brain cancer, skin cancer, oral cancer, prostate cancer, bone cancer, kidney cancer, ovarian cancer, bladder cancer, liver cancer, fallopian tube tumor, ovarian tumor, peritoneal tumor, melanoma, solid tumor, glioma, glioblastoma, hepatocellular carcinoma, mastoid renal tumor, head and neck tumor, leukemia, lymphoma, myeloma, or non-small cell lung cancer.

13. A method of treating a disease, comprising administering to a subject in need thereof an amount of the compound according to claim 1 or a mesomer, racemate, enantiomer, diastereomer thereof or a pharmaceutically acceptable salt thereof, wherein the disease is selected from the group consisting of rheumatoid arthritis, chronic lymphocytic leukemia (CLL), B-cell lymphomas, and mantle cell lymphoma.

14. A method of treating a disease, comprising administering to a subject in need thereof an amount of the composition of claim 2, wherein the disease is selected from the group consisting of rheumatoid arthritis, chronic lymphocytic leukemia (CLL), B-cell lymphomas, and mantle cell lymphoma.

* * * * *